United States Patent
Nagpal et al.

(10) Patent No.: US 10,364,461 B2
(45) Date of Patent: Jul. 30, 2019

(54) QUANTUM MOLECULAR SEQUENCING (QM-SEQ): IDENTIFICATION OF UNIQUE NANOELECTRONIC TUNNELING SPECTROSCOPY FINGERPRINTS FOR DNA, RNA, AND SINGLE NUCLEOTIDE MODIFICATIONS

(71) Applicant: THE REGENTS OF THE UNIVERSITY OF COLORADO, Denver, CO (US)

(72) Inventors: Prashant Nagpal, Lafayette, CO (US); Anushree Chatterjee, Lafayette, CO (US); Josep Casamada Ribot, Boulder, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 15/531,317

(22) PCT Filed: Dec. 7, 2015

(86) PCT No.: PCT/US2015/064248
§ 371 (c)(1),
(2) Date: May 26, 2017

(87) PCT Pub. No.: WO2016/094294
PCT Pub. Date: Jun. 16, 2016

(65) Prior Publication Data
US 2018/0087102 A1  Mar. 29, 2018

Related U.S. Application Data

(60) Provisional application No. 62/089,063, filed on Dec. 8, 2014.

(51) Int. Cl.
*G01Q 60/12* (2010.01)
*C12Q 1/6869* (2018.01)
(Continued)

(52) U.S. Cl.
CPC ........ *C12Q 1/6869* (2013.01); *C12Q 1/6874* (2013.01); *G01N 33/48721* (2013.01); *G01Q 60/12* (2013.01)

(58) Field of Classification Search
CPC ...... C12Q 1/6869; G01Q 60/04; G01Q 60/10; G01Q 60/12; G01Q 70/00; G01Q 70/02;
(Continued)

(56) References Cited

U.S. PATENT DOCUMENTS 5,106,729 A    4/1992  Lindsay et al.
5,270,214 A    12/1993 Sessler et al.
(Continued)

FOREIGN PATENT DOCUMENTS

WO  WO 2003-083437 A2  10/2003
WO  WO 2006-070946 A1  7/2006
WO  WO 2015-038972 A1  3/2015

OTHER PUBLICATIONS

Blow "DNA sequencing: generation next-next." *Nature Methods*, 5(3): 267-274 (2008).
(Continued)

*Primary Examiner* — Jason L McCormack
(74) *Attorney, Agent, or Firm* — Berg Hill Greenleaf Ruscitti LLP

(57) ABSTRACT

Techniques, methods, devices, and compositions are disclosed that are useful in identifying and sequencing natural and synthetic, and modified and unmodified DNA, RNA, PNA, DNA/RNA nucleotides. The disclosed techniques, methods, devices, and compositions are useful in identifying various modifications, DNA/RNA damage, and nucleotide
(Continued)

structure, using nanoelectronic quantum tunneling spectroscopy, which may be referred to as QM-Seq. The methods and compositions can include the use of a charged, smooth substrate for deposition of single stranded nucleotides and polynucleotide macromolecules, scanning the modified or unmodified DNA/RNA/PNA, comparing the electronic signatures of an unknown nucleobase against a database of electronic fingerprints of known nucleobases, including natural and synthetic, modified and unmodified nucleobases, and secondary/tertiary structure, obtained under the same or similar conditions, for example where the nucleobase is in an acidic environment.

16 Claims, 64 Drawing Sheets
Specification includes a Sequence Listing.

(51) Int. Cl.
*C12Q 1/6874* (2018.01)
*G01N 33/487* (2006.01)

(58) Field of Classification Search
CPC ........ G01Q 70/06; G01Q 70/08; G01Q 70/10; G01Q 70/14; G01Q 70/16
USPC ........ 850/23, 26, 27, 52, 53, 55, 56, 57, 58, 850/59, 60, 61
See application file for complete search history.

(56) References Cited

U.S. PATENT DOCUMENTS

| | | | |
|---|---|---|---|
| 5,601,982 A | 2/1997 | Sargent et al. | |
| 5,751,683 A * | 5/1998 | Kley | G01B 7/31 369/101 |
| 6,955,078 B2 * | 10/2005 | Mancevski | G01Q 40/00 73/105 |
| 2007/0082459 A1 * | 4/2007 | Faris | C12Q 1/6825 438/455 |
| 2008/0215252 A1 | 9/2008 | Kawai et al. | |
| 2009/0121133 A1 | 5/2009 | Amirparviz | |
| 2009/0155917 A1 * | 6/2009 | Umezawa | C12Q 1/6816 436/94 |
| 2011/0155574 A1 | 6/2011 | Golovchenko et al. | |
| 2012/0183970 A1 * | 7/2012 | Sappenfield | C12Q 1/6869 435/6.12 |
| 2013/0176563 A1 * | 7/2013 | Ozawa | B82Y 5/00 356/301 |
| 2015/0309073 A1 * | 10/2015 | Mirkin | B82Y 40/00 850/55 |
| 2016/0222445 A1 | 8/2016 | Nagpal et al. | |

OTHER PUBLICATIONS

Chang et al. "Electronic Signatures of all Four DNA Nucleotides in a Tunneling Gap." *NANO Letters*, 10: 1070-1075 (2010).
Cricenti et al. "Molecular Structure of DNA by Scanning Tunneling Microscopy." *Science*, 245: 1226-1227 (1989).
Cricenti et al. "Imaging of Single-Stranded DNA." *AIP Conf. Proc.*, 241: 159-165 (1992).
Driscoll et al. "Atomic-scale imaging of DNA using scanning tunneling microscopy." *Nature*, 346: 294-296 (1990).
Dunlap and Bustamante "Images of single-stranded nucleic acids by scanning tunneling microscopy." *Letters to Nature*, 342: 204-206 (1989).
International Preliminary Report on Patentability, dated Mar. 24, 2016 for Application No. PCT/US2014/055512, 8 pages.
International Search Report and Written Opinion dated Feb. 25, 2016 for Application No. PCT/US2015/064248, 14 pages.
Kilina et al. "Electronic Properties of DNA Base Molecules Adsorbed on a Metallic Surface." *Journal of Physical Chemistry C*, 111(39): 14541-14551 (2007).
Lindsay and Philipp "Can the Scanning Tunneling Microscope Sequence DNA." *Genetic Analysis: Biomolecular Engineering*, 8(1): 8-13 (1991).
Lund et al. "Using Electron Tunneling for Direct Sequencing of DNA." *Technical Proceedings of the 2007 NSTI Nanotechnology Conference and Trade Show*, 2: 780-783 (2007).
Mehta et al. "Molecular Combining for Stretching Single-Stranded Phage Genomes on Conductive Graphite Surfaces." *Proceedings of the $2^{nd}$ IEEE International Conference on Nano/Mocro Engineered and Molecular Systems*, Jan. 16-19 Bangkok, Thailand, pp. 943-946 (2007).
Nagpal et al. (Ultrasmooth Patterned Metals for Plasmonics and Metaaterials Science, 325: 594-597 (2009).
Ribot et al. "Quantum-Sequencing: Biophysics of quantum tunneling through nucleic acids" APS March Meeting Abstracts, p. 1 (2013).
Ribot et al. "Quantum-Sequencing: Fast electronic single DNA molecule sequencing." APS Meeting Abstracts, p. 1 (2013).
Tanaka and Kawai "Partial sequencing of a single DNA molecule with a scanning tunneling microscope." *Nature Nanotechnology*, 4: 518-522 (2009).
Woolley and Kelly "Deposition and Characterization of Extended Single-Stranded DNA Molecules on Surfaces." *NANO Letters*, 1(7): 345-348 (2001).
Yarotski "Electronic fingerprints of DNA nucleotides for DNA sequencing with scanning tunneling spectroscopy." CECAM— Centre European de Calcul Atomique et Moleculaire, URL:http://www.cecam.org/workshop-4-822.html, pp. 1-3 (2012).
Youngquist et al. "Scanning tunneling microscopy of DNA: Atom-resolved imaging, general observations and possible contrast mechanism." *Journal of Vacuum Science and Technology B*, 9(2): 1304-1308 (1991).
Zwolak and Di Ventra "Electronic Signature of DNA Nucleotides via Transverse Transport." *NANO Letters*, 5(3): 421-424 (2005).

* cited by examiner

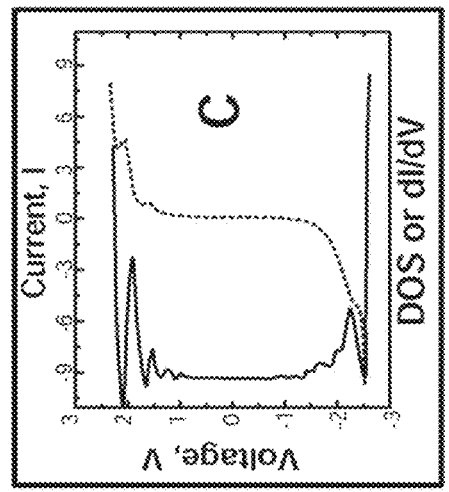
FIG. 1E
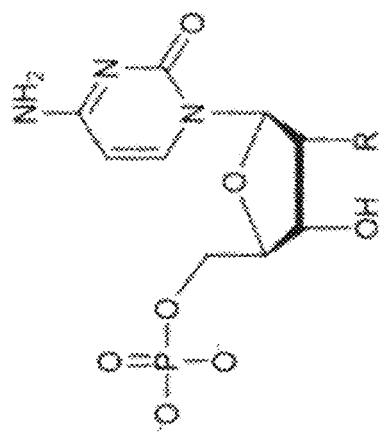
FIG. 1F
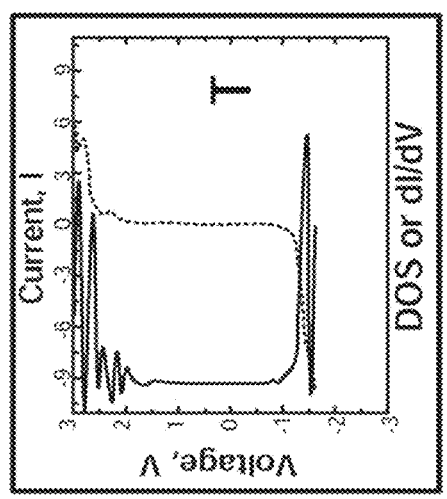
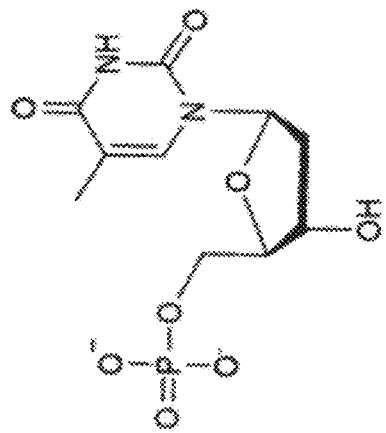

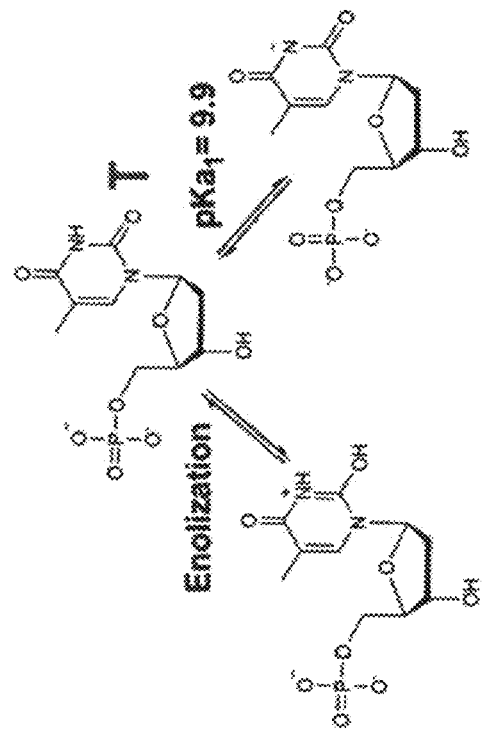
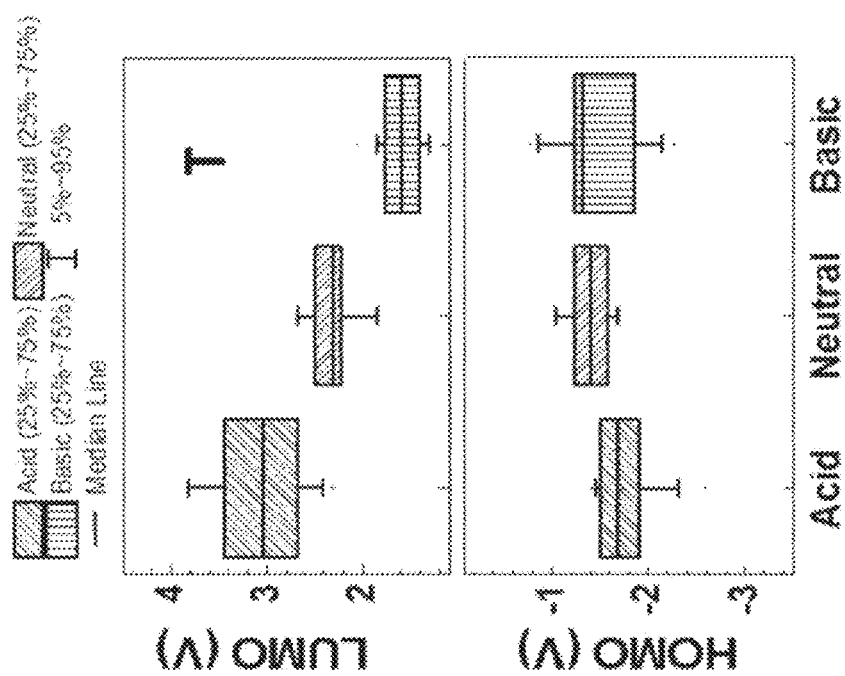
FIG. 5D
FIG. 5C

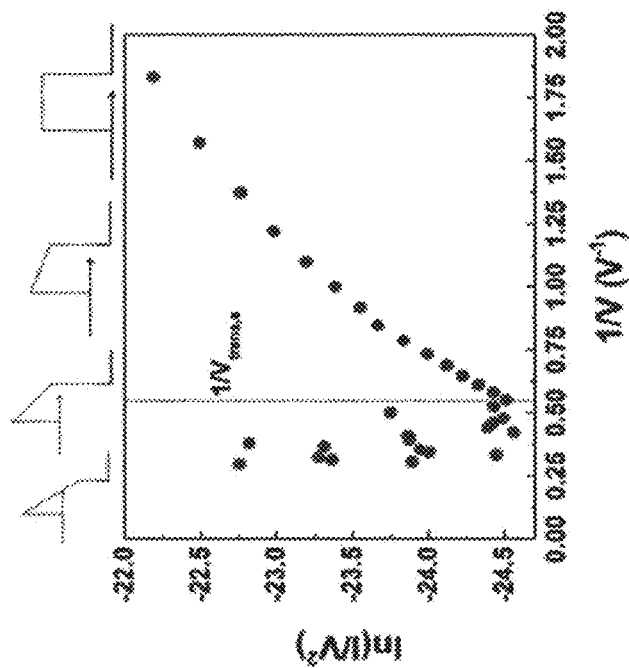
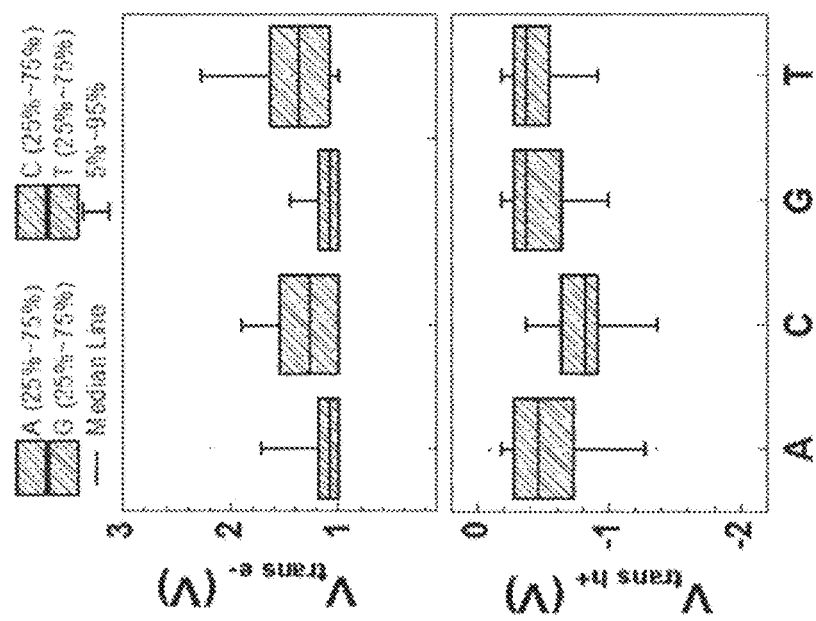
FIG. 5F
FIG. 5E

FIG. 6D (SEQ ID NO: 3)

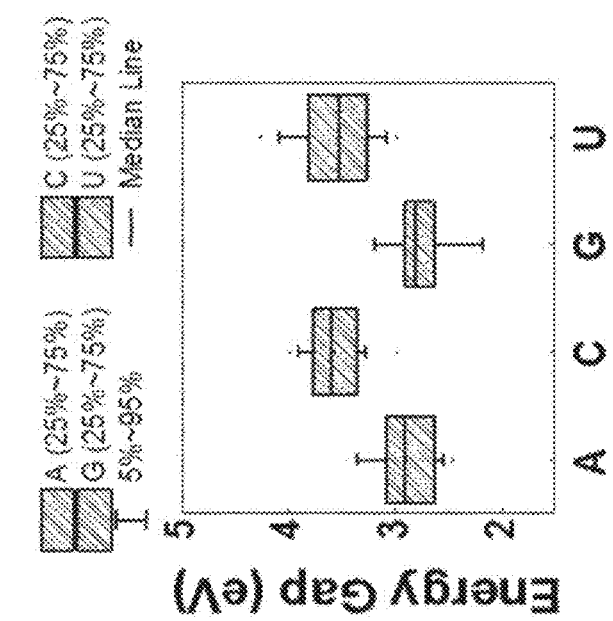
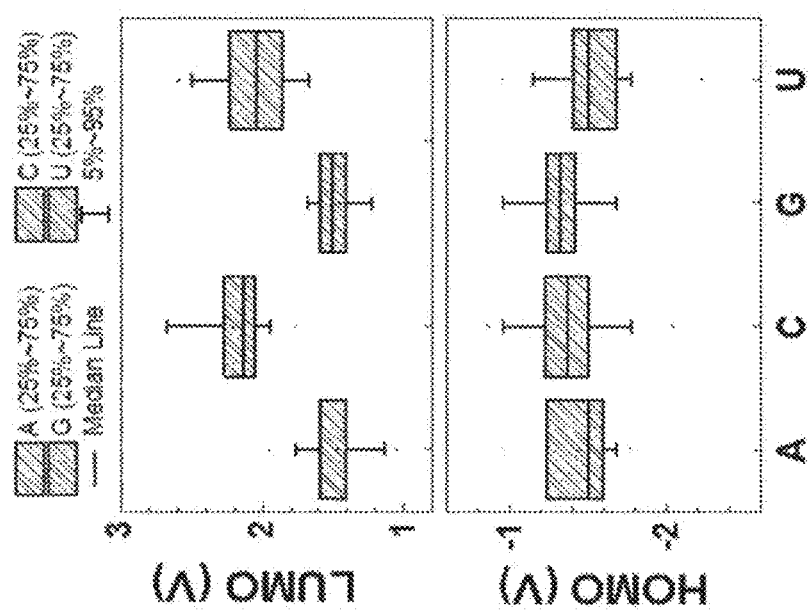
FIG. 7B
FIG. 7A

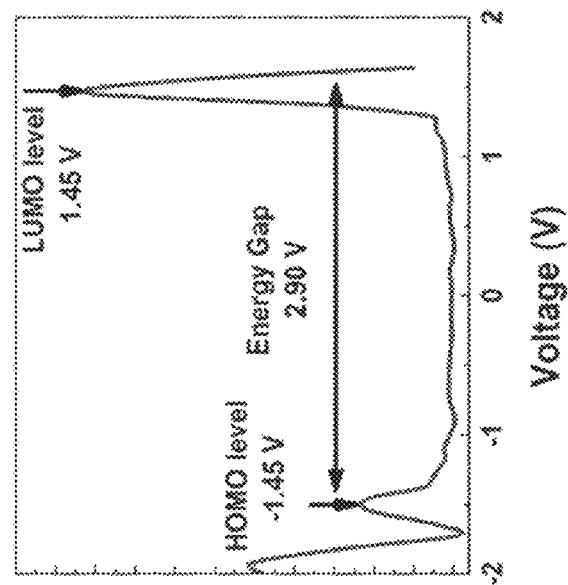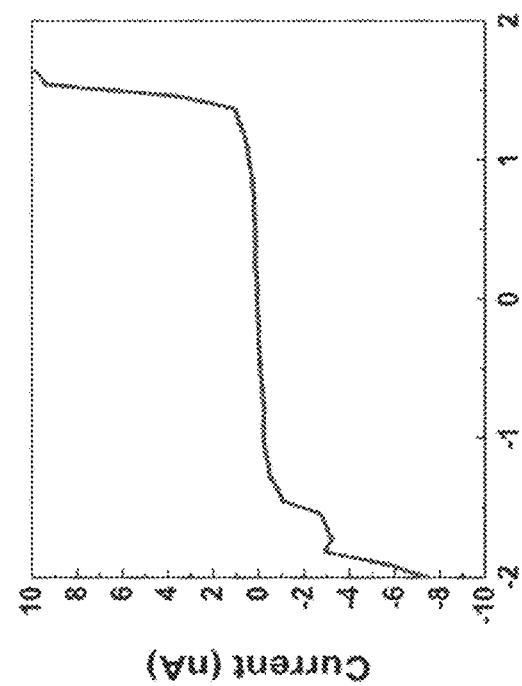
FIG. 10A
FIG. 10B

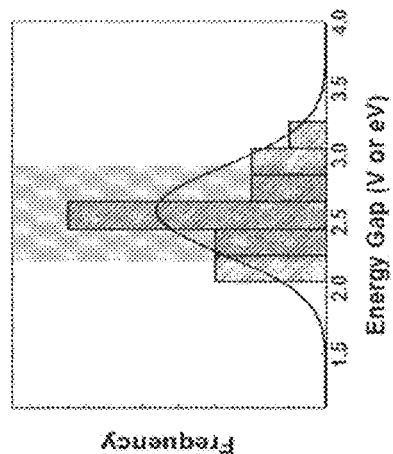
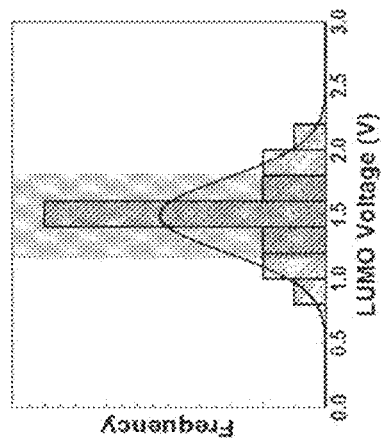
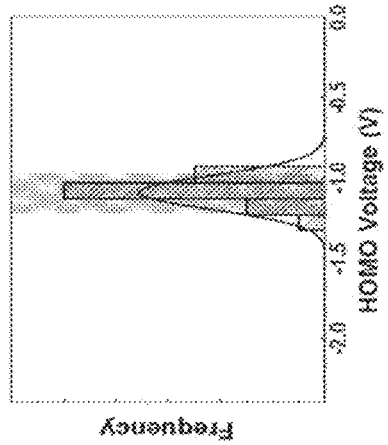
FIG. 13E
FIG. 13D
FIG. 13C

QUANTUM MOLECULAR SEQUENCING (QM-SEQ): IDENTIFICATION OF UNIQUE NANOELECTRONIC TUNNELING SPECTROSCOPY FINGERPRINTS FOR DNA, RNA, AND SINGLE NUCLEOTIDE MODIFICATIONS

CROSS-REFERENCE TO RELATED APPLICATIONS

The present application is a national stage entry pursuant to 35 U.S.C. § 371 of International Application No. PCT/US2015/064248, filed Dec. 7, 2015, which claims the benefit of priority of U.S. Provisional Application No. 62/089,063, filed Dec. 8, 2014, each of which is incorporated by reference herein in its entirety for any purpose.

SEQUENCE LISTING

The present application is filed with a Sequence Listing in electronic format. The Sequence Listing is provided as a file entitled "2015-12-04_01144-0001-00PCT_Seq_List_ST25.txt" created on Dec. 4, 2015, which is 1,155 bytes in size. The information in the electronic format of the sequence listing is incorporated herein by reference in its entirety.

FIELD

The disclosed methods, devices, compositions, and systems are directed to identifying and sequencing of nucleic acids.

BACKGROUND

New diagnostic tools for personalized medicine and the rapidly evolving field of genetics requires inexpensive, fast, reliable, enzyme-free, and high-throughput sequencing techniques. While several DNA sequencing techniques developed recently have tried to reduce the sequencing costs and time, the reported nucleic acid sequences are statistically significant ensemble averages. While these ensemble averages can be used to derive some correlation between nucleotide sequences and physiological behavior, trace levels of genetic variations or mutations can dominate the biological functions. This is exemplified by the rapid emergence of multi-drug resistant strains of bacteria, or superbugs, and fast mutating pathogens which nominally exist in trace quantities before drug treatments. Recent studies involving fast identification of drug-resistance encoding DNA sequences, such as β-lactamases, which cause resistance against penicillin-based antibiotics, have shown that these techniques are essential for providing timely, targeted medical intervention, thus underscoring the need for reliable single molecule sequencing tools for rapid and high-throughput sequencing. Current second generation sequencing technologies are capable of detecting single nucleotide polymorphisms (SNP) using deep and ultra-deep (about 100 reads per polynucleotide) sequencing methods, and single copy PCR (polymerase chain reaction) amplification. However, these methods are expensive and technically complex, making them difficult to apply in clinical settings. While recent studies have outlined the potential use of single-cell genomics for medicine and non-invasive clinical applications, these studies involve enzymatic amplification of DNA from single molecules, and DNA sequencing using traditional sequencing tools (optical markers). Thus, the present techniques for identification of DNA rely on enzyme based DNA amplification which can introduce sequence bias and can potentially lead to errors in DNA sequence detection for trace or single-cell samples. Other new techniques have tried to improve the sequencing errors in de novo sequencing, with the use of nucleic acid markers and specific enzymes that allow sequencing of DNA molecules only.

Electronic identification of DNA sequences is a candidate for next-generation sequencing technology, as it may offer an enzyme-free technique without DNA amplification. This method may offer the possibility of reducing processing time and errors associated with other techniques. Several groups have been exploring using nanopore conductance of DNA nucleotides based on either ionic current change along the pore, or tunneling current decay when a base is traversing the pore. In these experiments, DNA is made to travel through a very small hole, where its structure is probed. However, this method lacks single molecule resolution capability and suffers from insufficient change in conductance due to nucleotide modifications, thus limiting its potential use for diagnostics and epigenomics identifications. Other studies have explored scanning tunneling microscopy for single molecule detection and identification. Although imaging of single DNA molecules, using scanning tunneling microscopy has been accomplished, none have offered a reliable method or device for accurate, reproducible, and efficient identification and discrimination of individual nucleotides, nucleosides, and nucleobases or the ability to sequence nucleotides, nucleosides, and nucleobases in a molecule with multiple nucleotides, nucleosides, nucleobases, and combinations thereof.

RNA sequencing presents unique challenges. In the recent years, massively parallel RNA sequencing, has allowed high-throughput quantification of gene expression and identification of rare transcripts, including small RNA characterization, transcription start site identification among others. However, most RNA sequencing methods rely on cDNA synthesis as well as a number of manipulations which introduce bias at multiple levels including priming with random hexamers, ligation, amplification and sequencing. Moreover, a number of common natural (5-methylcytosine, pseudouridine) and chemical modifications (N7-methylguanine) do not stop reverse transcriptase during cDNA synthesis and therefore are not detected using high throughput DNA sequencing methods. Commonly used reverse transcriptases are also known to introduce artifacts into the cDNA, e.g. tendency to delete nucleotides in regions of RNA secondary structure. This leads to a "blurring" of the sequencing pattern in the resultant cDNA. Further, DNA methylation, which is not detected by present sequencing techniques, has been found to be a dominant marker for cancer cells, and can been used to distinguish the somatic changes that occur between cancerous cells and non-cancerous cells.

SUMMARY

Techniques, methods, devices, and compositions disclosed herein may be used to determine the identity of an unknown nucleotide, nucleoside, or nucleobase wherein the method comprises, analyzing the unknown nucleotide, nucleoside, and nucleobase by quantum tunneling, determining one or more electronic parameters for the unknown nucleotide, nucleoside, and nucleobase, using the electronic parameters to determine a signature for the nucleotide, nucleoside, and nucleobase, comparing the electronic signature of the unknown base to electronic fingerprints for one or more known nucleotides, nucleosides, and nucleobases, matching the unknown nucleotides', nucleosides', and nucleobases' electronic signature to an electronic fingerprint of a known base (for example, modified and unmodified DNA nucleotides Adenine, A, Thymine, T, Guanine, G, Cytosine, C, RNA nucleotides A, G, C, Uracyl, U, Peptide Nucleic Acids (PNA) and other artificial nucleic acid macromolecules, nucleotide modifications like methylation, 5-carboxy, 5-formyl, 5-hydroxymethyl, 5-methyl deoxy, 5-methyl, 5-hydroxymethyl, N6-methyl-deoxyadenosine, and other modifications used to determine RNA secondary/tertiary structure like N-methyl isatoic anhydride (NMIA) or dimethyl sulfate (DMS)), and thereby identifying the unknown nucleobase, nucleobase modifications or nucleic acid macromolecule secondary/tertiary structure. In many embodiments, the electronic signature of the unknown nucleobase may be determined while the nucleobase is in a specific biochemical condition or environment, for example a pH environment selected from acidic, neutral, or basic pH. In many embodiments, a nucleobase's electronic signature is altered by the biochemical condition, e.g., the pH environment. In some embodiments, the unknown nucleobase's identity is determined in an acidic environment, where the various modified and unmodified nucleobases can be differentiated. In many embodiments, the disclosed method of identifying an unknown nucleobase may involve a computing device that comprises one or more standard electronic fingerprints and matches an electronic signature of an unknown nucleobase to the one or more standard electronic fingerprints.

The disclosed technique can be used to determine the 3'→5' order of a polynucleotide (or other macromolecule having one or more nucleotide, nucleoside, nucleobase or combinations thereof) by tagging the 5' end of the polynucleotide. In many cases, polynucleotide refers to a macromolecule comprising one or more nucleotides, nucleosides, nucleobases, or combinations thereof. This is achieved, in some embodiments, by ligation of a specific 5' or 3' end specific primer tag (in some cases by using T4 ligase) to create templates with 5'- and 3'-ends of known sequences. Using the disclosed methods, devices, and compositions, the sequence of the polynucleotides (or other polymeric molecule comprising one or more nucleotide, nucleoside, nucleobase, or combinations thereof) will be identified which will reveal the directionality of the unknown DNA/RNA/PNA sample.

Microfluidic devices described here can be used to change the pH for simultaneous or near simultaneous determination of an electronic signature of a nucleobase in two or more different environmental conditions. Using the microfluidic channels can feed DNA (for example single stranded DNA) from single DNA wells, as shown in FIG. 26, wherein channels are coated with different polyelectrolytes (polyanions and polycations) to alter and maintain the pH of an environment to desired value. Then a single metal tip, or a plurality of tips (e.g. as described below for parallel sequencing), can be used to sequence nucleobases in different pH environments and other biochemical conditions.

Also disclosed, is a method that may be used to identify multiple unknown nucleotides/nucleobases using the unique electronic fingerprints described herein, wherein the electronic fingerprints comprise one or more biophysical electronic parameters such as values for HOMO level, LUMO level, bandgap, Fowler-Nordheim transition voltage for electrons and holes, slope of the tunneling curve, tunneling barrier height for electron and holes, the difference in barrier heights for electrons and holes, effective masses of electrons and holes, ratio of effective masses of electron and holes in different biochemical conditions, etc. These biophysical electronic parameters may be used in various combinations in order to identify the unknown, modified or unmodified nucleotides/nucleobases. In many cases, the identity of the unknown nucleotide/nucleobase may be determined with a high-degree of confidence. The disclosed methods may include the use of a clustering method wherein one or more biophysical electronic parameters for a number of known nucleobase/nucleotides are used to create electronic fingerprints, which can be compared to an electronic signature determined for an unknown nucleobase/nucleotide. In many cases, the electronic parameters are stored as electronic data in a computer program which can be used to select the electronic parameters determined for the unknown nucleobase/nucleotide and compare with a similarly configured fingerprint (comprising values for the same parameters as were selected for the electronic signature) of a known nucleotide/nucleobase. The disclosed methods can be used for automated sequencing and calling the nucleobases for a robust sequencing technique and software analysis.

Compositions useful in determining the identity of unknown nucleobases are also disclosed. In some embodiments, a substrate for determining the identity of a nucleobase is disclosed wherein the substrate may be a smooth highly ordered gold substrate, for example Au(111). In some embodiments, the substrate is charged and treated with a solution comprising one or more ionic molecules, for example poly-L-lysine, wherein the ionic molecule may aid in linking a negatively charged polymer, such as single stranded DNA, to the gold substrate.

Chemical modifications of the nucleotide/nucleobases are also determined using the disclosed methods. In some cases, chemical modifications may be useful in determining the secondary/tertiary nucleic acid macromolecular structure of a polynucleotide or other polymeric molecule comprising one or more nucleotides, nucleosides, nucleobases, or combinations thereof. In some cases, polynucleotides may be modified using N-methyl isatoic anhydride (NMIA), dimethyl sulfate (DMS) and the like. Chemical modifications of DNA/RNA/PNA may also be useful in determining epigenetic markers and nucleic acid damage. In some cases the chemical modification may be 5-carboxy, 5-formyl, 5-hydroxymethyl, 5-methyl deoxy, 5-methyl, 5-hydroxymethyl, N6-methyl-deoxyadenosine, and the like. The chemical modification may be determined simultaneously with unmodified DNA/RNA/PNA nucleotides using the disclosed electronic fingerprints.

In some embodiments, a sequencer is provided, wherein the sequencer comprises:
  a processor;
  a read head having a plurality of quantum tunneling tips;
  a substrate capable of supporting at least one polynucleotide that comprises one or more nucleobases;
  a bias voltage coupled to the processor and providing a voltage between the read head and the substrate;
  a current sensor coupled between the bias voltage and the read head, the current sensor providing a current to the processor,
  wherein the processor executes instructions to acquire electronic signature data at a set of positions across the sample and store the electronic signature data according to position, and
wherein individual nucleobases can be identified based on the electronic signature data.

In some embodiments, the read head of the sequencer comprises at least 100, at least 500, at least 1000, at least 5000, at least 10,000, at least 50,000, at least 100,000, at least 200,000, at least 500,000, at least 1,000,000, or at least 2,000,000 quantum tunneling tips. In some embodiments, the read head does not comprise an array of 1,000 by 1,000 quantum tunneling tips. In some embodiments, each quantum tunneling tip comprises a metal-insulator-semiconductor (MIS) structure. In some embodiments, each quantum tunneling tip comprises a metal-insulator-metal (MIM) structure. In some embodiments, the plurality of quantum tunneling tips are arranged so that currents from individual tips can be independently read. In some embodiments, the currents from the individual tips are simultaneously read.

In some embodiments, the substrate is a conductive substrate. In some embodiments, the conductive substrate is an ultrasmooth metal substrate. In some embodiments, the conductive substrate is an ultrasmooth Au(111) substrate. In some embodiments, the substrate comprises channels into which a sample may be flowed to deposit at least one polynucleotide onto the substrate. In some embodiments, each channel comprises a bottom surface and two walls, wherein the bottom surface is the conductive substrate and the walls are composed of a hydrophobic polymer. In some embodiments, the substrate comprises a polycationic surface. In some embodiments, the polycationic surface comprises a polycationic polymer and/or a positively charged polyelectrolyte. In some embodiments, the polycationic surface comprises polylysine.

In some embodiments, the plurality of quantum tunneling tips form a rectangular array, wherein the rectangular array comprises a length and a width, wherein the length is no more than 2×, or no more than 1.5×, the width. In some embodiments, the array is square. In some embodiments, two adjacent quantum tunneling tips are between 10 nm and 100 µm, or between 10 nm and 10 µm, or between 10 nm and 1 µm, or between 10 nm and 100 nm apart. In some embodiments, each quantum tunneling tip is between 10 nm and 100 µm, or between 10 nm and 10 µm, or between 10 nm and 1 µm, or between 10 nm and 100 nm away from its nearest neighbor quantum tunneling tip.

In some embodiments, the sequencer comprises at least one polynucleotide associated with the substrate. In some embodiments, the at least one polynucleotide is associated with the substrate through ionic bonds. In some embodiments, the polynucleotide is single-stranded. In some embodiments, the polynucleotide is selected from DNA, RNA, modified DNA, modified RNA, peptide nucleic acid (PNA), and aptamers, including modified aptamers.

In some embodiments, the processor executes instructions to
  (a) position the read head relative to the substrate at a starting position;
  (b) scan the voltage and measure the current to acquire electronic signature data;
  (c) store the electronic signature data relative to a position between the read head and the substrate;
  (d) reposition the read head relative to the substrate according to a scan pattern; and
  (e) repeat steps (b) through (e) until the scan pattern is complete.

In some embodiments, the processor further executes instructions to
  identify locations of the nucleobases based on the electronic signature data;
  calculate parameter fingerprints at the identified locations from the electronic signature data; and
  identify the nucleobases based on the parameter fingerprints.

In some embodiments, the electronic signature data is provided to a separate computing system that executes instructions to
  identify locations of the nucleobases based on the electronic signature data;
  calculate parameter fingerprints at the identified locations from the electronic signature data; and
  identify the nucleobases based on the parameter fingerprints.

In some embodiments, locations of the nucleobases are identified by
  calculating dI/dV, HOMO and LUMO parameters from the electronic signature data;
  comparing the parameters with those of the substrate; and
  identifying where the tip is positioned over only the substrate and where the tip is positioned over nucleobases based on the comparison.

In some embodiments, calculating parameter fingerprints includes calculating from the electronic signature data at least three, at least four, at least five, at least six, at least seven, at least eight or at least nine of the parameters selected from the group LUMO, HOMO, Bandgap, $V_{trans+}$ (V), $V_{trans-}$ (V), $\phi_{e-}$ (eV), $\phi_{h+}$ (eV), $m_{e-}/m_{h+}$ and $\Delta\phi$ (eV). In some embodiments, identifying the nucleobases based on the parameter fingerprints includes comparing the parameter fingerprints with known fingerprints stored in a fingerprint database. In some embodiments, comparing the parameter fingerprints includes determining a probability that the parameter fingerprint is within a group of known fingerprints stored in the fingerprint databases.

In some embodiments, methods of identifying unknown nucleobases are provided. In some such embodiments, the method comprises determining the sequence of a polynucleotide. In some embodiments, a method of identifying a first unknown nucleobase comprises:
  determining an electronic signature for the first unknown nucleobase using a sequencer described herein to collect tunneling current data;
  comparing the electronic signature of the first unknown nucleobase to an electronic fingerprint for one or more known nucleobases;
  matching the first unknown nucleobase's electronic signature to an electronic fingerprint of a known nucleobase; and thereby
  identifying the first unknown nucleobase.

In some embodiments, the electronic signature of the first unknown nucleobase and the electronic fingerprint of the known nucleobases comprise at least three, at least four, at least five, at least six, at least seven, at least eight, or at least nine values selected from the values of LUMO, HOMO, Bandgap, $V_{trans+}$ (V), $V_{trans-}$ (V), $\phi_{e-}$ (eV), $\phi_{h+}$ (eV), $m_{e-}/m_{h+}$ and $\Delta\phi$ (eV).

In some embodiments, the method comprises identifying a second unknown nucleobase. In some embodiments, the first and second unknown nucleobases are comprised on the same polynucleotide molecule. In some embodiments, the first and second unknown nucleobases are comprised on different polynucleotide molecules. In some embodiments, the first unknown nucleobase is selected from the group consisting of modified and unmodified adenine, guanine, cytosine, thymine and uracil.

In some embodiments, the electronic signature of the first unknown nucleobase is determined in one or more pH environments selected from acidic, neutral, and basic, and compared to the electronic fingerprint of the one or more known bases collected in the same pH environment. In some embodiments, the pH environment is basic. In some such embodiments, the pH is greater than 9. In some embodiments, the pH environment is acidic. In some such embodiments, the pH is less than 3. In some embodiments, a second pH environment is basic. In some embodiments, the second pH is greater than 9. In some embodiments, the first unknown nucleobase is a methylated nucleobase.

In some embodiments, the polynucleotide is deposited on the substrate by a process comprising a translational motion. In some embodiments, the polynucleotide is single-stranded. In some embodiments, the method comprises melting at least one double-stranded polynucleotide to form single-stranded polynucleotides prior to depositing the polynucleotides on the substrate.

In some embodiments, a method of identifying a first unknown nucleotide is provided, comprising:

performing scanning tunneling spectroscopy on an unknown nucleotide positioned on a poly lysine coated ultrasmooth oriented gold (111) surface using a sequencer described herein;

collecting scanning tunneling data for the unknown nucleotide at acidic pH;

processing the scanning tunneling data to produce values for three or more parameters selected from LUMO, HOMO, Bandgap, $V_{trans+}$ (V), $V_{trans-}$ (V), $\phi_{e-}$ (eV), $\phi_{h+}$ (eV), $m_e/m_{h+}$ and $\Delta\phi$ (eV);

identifying the nucleotide as adenine if
the HOMO value is between −1.09 and −1.69;
the LUMO value is between about 1.66 and 1.18;
the Bandgap value is between about 3.22 and 2.40;
the $V_{trans+}$ value is between about 1.34 and 0.96;
the $V_{trans-}$ value is between about −0.19 and −0.83;
the $\phi_{e-}$ value is between about 2.02 and 0.88;
the $\phi_{h+}$ value is between about 1.64 and 0.42;
the $m_e/m_{h+}$ value is between about 0.52 and 0.06; and/or
the $\Delta\phi$ value is between about 3.46 and 1.5; or identifying the nucleotide as guanine if
the HOMO value is between −1.17 and −1.55;
the LUMO value is between 1.72 and 1.24;
the Bandgap value is between 3.11 and 2.57;
the $V_{trans+}$ value is between 1.26 and 1;
the $V_{trans-}$ value is between −0.19 and −0.77;
the $\phi_{e-}$ value is between 1.63 and 1.03;
the $\phi_{h+}$ value is between 1.29 and 0.29;
$m_e/m_{h+}$ value is between 0.57 and 0.07;
the $\Delta\phi$ value is between 2.77 and 1.47; or identifying the nucleotide as cytosine if
the HOMO value is between −1.47 and −2.15;
the LUMO value is between 2.79 and 1.99;
the Bandgap value is between 4.69 and 3.71;
the $V_{trans+}$ value is between 1.65 and 1.03;
the $V_{trans-}$ value is between −0.54 and −1.06;
the $\phi_{e-}$ value is between 3.51 and 1.73;
the $\phi_{h+}$ value is between 2.2 and 0.94;
$m_e/m_{h+}$ value is between 0.95 and 0.33;
the $\Delta\phi$ value is between 5.36 and 3.02; or identifying the nucleotide as thymine if
the HOMO value is between −1.19 and −1.57;
the LUMO value is between 2.98 and 2.38;
the Bandgap value is between 4.38 and 3.74;
the $V_{trans+}$ value is between 1.8 and 1.06;
the $V_{trans-}$ value is between −0.25 and −0.63;
the $\phi_{e-}$ value is between 3.44 and 2.06;
the $\phi_{h+}$ value is between 1.25 and 0.45;
$m_e/m_{h+}$ value is between 0.5 and 0.16;
the $\Delta\phi$ value is between 4.34 and 2.88.

While multiple embodiments are disclosed, still other embodiments of the present invention will become apparent to those skilled in the art from the following detailed description. As will be apparent, the invention may be practiced through modifications of various described aspects, all without departing from the spirit and scope of the present invention. Accordingly, the detailed description is to be regarded as illustrative in nature and not restrictive.

BRIEF DESCRIPTION OF THE DRAWINGS

FIGS. 1A-G: Sequencing nucleic acid macromolecules like DNA, RNA, PNA, using Quantum Molecular Sequencing (QM-Seq). (a) Illustration of QM-Seq showing single stranded (ss) DNA deposited on clean Au (111) surface. A three-step extrusion deposition scheme is used to reproducibly obtain stretched, linearized DNA and RNA molecules, with reduced configurational entropy. The metal tip used to obtain QM-Seq electronic spectra (tunneling data) acts as a "read head". (b) QM-Seq utilizes nanoelectronic tunneling of electrons and holes through nucleotides to provide unique electronic fingerprints. Schematic of frontier band structure, HOMO and LUMO molecular orbitals is shown for purines and pyrimidines at acidic conditions where significant differences can be observed between both nucleobases (not drawn to scale). Different degrees of conjugation and chemically distinct nucleobases (adenine and thymine here) lead to different electronic states and energy gaps. (c-g) Representative QM-Seq spectra (tunneling data) for each (deoxy) ribonucleotide with its corresponding chemical structures. R- can be either H or OH for deoxyribonucleotides (DNA) and ribonucleotides (RNA) respectively. Spectral data was measured at acidic conditions. Spectra shown here correspond to DNA nucleotides (A,C,G,T) and RNA nucleotide (U). Structures shown are (c) (deoxy)adenosine 5'-monophosphate, (d) (deoxy)guanosine 5'-monophosphate, (e) (deoxy)cytidine 5'-monophosphate, (f) thymidine 5'-monophosphate and (g) uridine 5'-monophosphate. A, G, C, T/U nucleotides are always denoted with green, black, blue and red colors, respectively.

FIGS. 5A-F: Electronic fingerprints for DNA nucleotides. (a) Boxplot of measured HOMO (negative) and LUMO (positive) levels for A, G, C and T, under acidic conditions poly-L-lysine-modified surface (washed with 0.1 M HCl). Boxplot contains second and third quartiles (25-75%) while whiskers show the data from 5-95%. A clear separation of LUMO levels (positive voltage peaks) was used to identify pyrimidines (C, T) from purines (A, G), and differences in HOMO levels was used to separate pyrimidines (C from T), in protonated molecules. (b) Energy gap between LUMO and HOMO energy levels under acidic conditions. This energy gap can be different from a neutral molecule. (c) HOMO/LUMO levels of Thymine at acidic (HCl), neutral (H$_2$O) and basic (NaOH) pH conditions. (d) Biochemical structures of Thymine at different pH conditions including keto-enol tautomerization at acidic conditions, and acid-base behavior between neutral and basic conditions. (e) Distribution of transition voltage for electron ($V_{trans,e-}$) and hole ($V_{trans,h-}$) at acidic conditions for all four nucleotides. $V_{trans,e-}$–$V_{trans,h-}$. show the same behavior as HOMO-LUMO levels and their energy bandgap, respectively. (f) Electron Fowler-Nordheim plot of Thymine at acidic conditions, characterized by its transition voltage ($V_{trans,e-}$) and the slope of triangular tunneling (proportional to the tunneling energy barrier). The schematic shows transition from direct tunneling at low voltages to triangular tunneling at high bias voltage. At very low voltages (zero-bias limit), the barrier becomes rectangular and the tunneling current shows a logarithmic slope with applied bias voltage.

FIG. 6A-D: Sequencing of beta-lactamase gene ampR using STM-STS. (a) Characterization of Adenine at acidic conditions on poly-L-lysine modified gold. Solid green line shows dI/dV or density of states, dashed grey line is the I-V data, and dotted green line shows the distribution of the HOMO and LUMO energy levels. (b) STM image of single ssDNA molecule of 1091 nt ampR gene. Image shows DNA is linearized on top of poly-L-Lysine modified gold substrate, allowing easy STS identification. (c) Identification of DNA nucleotides in the highlighted region shown in (b), using electronic fingerprint of A, G, C and T under acidic conditions, measured using STM-STS. Identified nucleotides are color coded (black: A or G, blue: C and red: T). (d) Identified ampR sequence based on primary (highlighted) and secondary identifications using STS data from (c).

FIGS. 7A-D: Electronic fingerprints for RNA nucleotides and comparison to DNA: (a) Boxplot of HOMO and LUMO energy of the ensemble of single molecule measurements of RNA nucleotides at acidic conditions, box comprises 25-75% while whiskers show the 5% to 95% of the values. (b) Boxplot of measured energy band gap of RNA nucleotides at acidic conditions showing two distinct energy levels for purines and pyrimidines. (c-d) Comparison of distribution of HOMO/LUMO energy levels for same nucleobases on DNA and RNA, (c) deoxyadenosine and adenosine comparison, (d) deoxycytidine and cytidine comparison.

FIGS. 10A-B: Measurement of I-V and density of electronic states (dI/dV) spectra. (a) STS Current (I)-Voltage (V) curve for Cytosine at neutral pH, (b) its derivative showing the peaks positions (HOMO and LUMO energy levels) and its energy gap. The tunneling signatures shown in other figures are probability density functions representing ensembles of at least 20 independent spectroscopy data, measured for the respective nucleobases. For each the independent measurement of I-V spectra, the derivative dI/dV was used to identify the HOMO and LUMO levels, and the energy band gap. These were then used to generate the probability density functions which represents the normal distributions from the energy positions of both HOMO and LUMO levels, and the energy band gap. The polydispersity of electronic signatures is likely caused by the configurational entropy, or charge tunneling through different molecular conformations aided by the thermal energy at room temperature.

FIGS. 13A-E: Raw data and statistics of guanine: (a) Raw current-voltage (I-V) curves for Guanine at acidic conditions. (b) Raw spectra or dI/dV of (a), arrows indicate identified HOMO/LUMO levels as the first significant negative/positive peak on each spectra. (c-e). Histograms of the positions of HOMO (c), LUMO (d) and Energy Gap (e) for guanine, superimposed by a normal probability density function (indicated by curve, also shown in FIG. 4a,b) fitted to the data set. The shaded box in each of 13C, 13D, and 13E indicates the area of the curve comprising the mean±standard deviation.

DETAILED DESCRIPTION

Figure 1A:
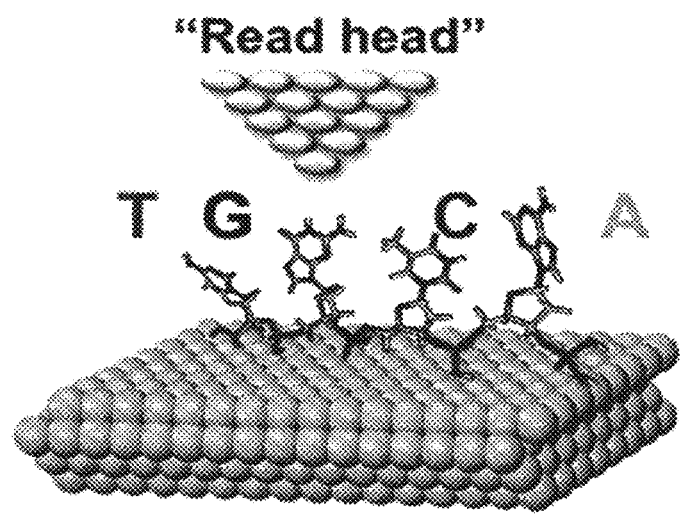
Figure 1B:
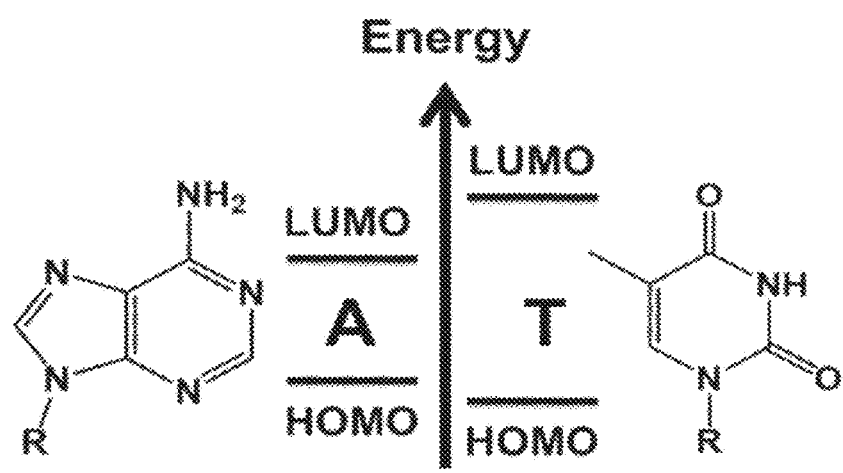
Figure 1C:
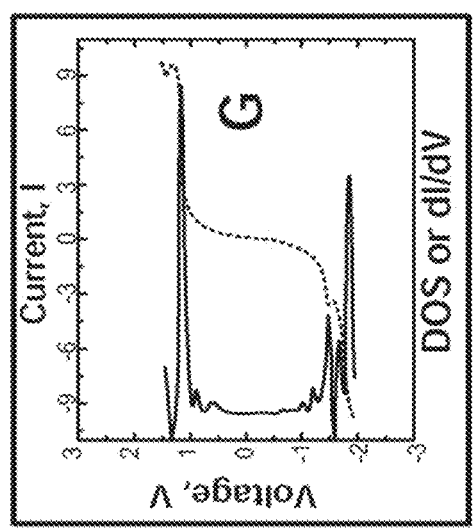
Figure 1C:
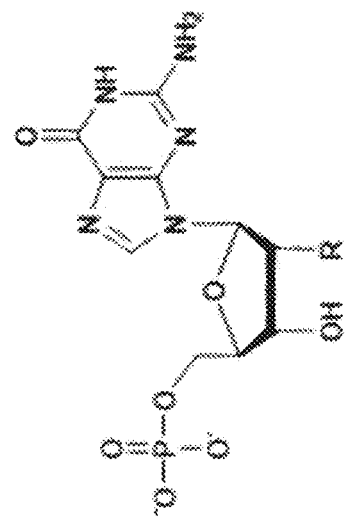
Figure 1D:
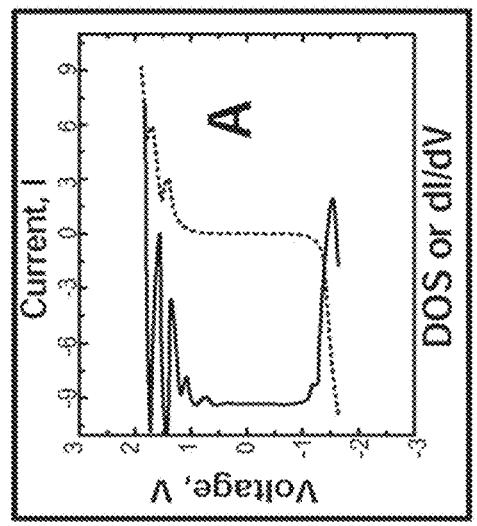
Figure 1D:
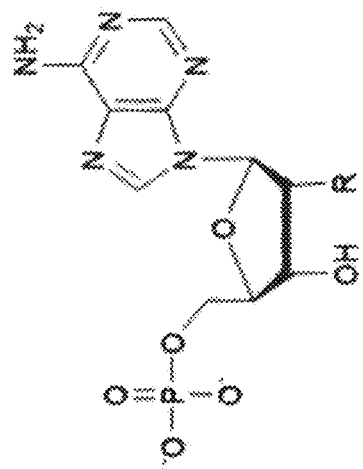
Figure 1G:
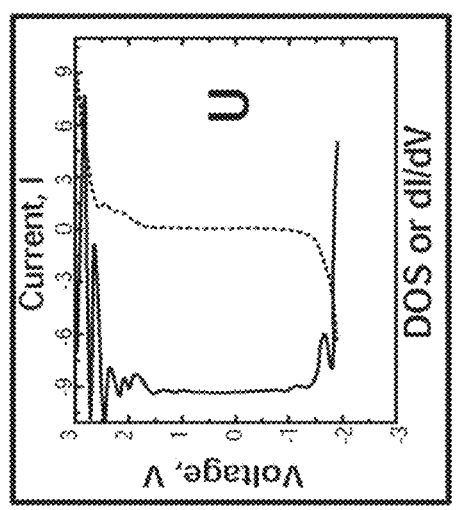
Figure 1G:
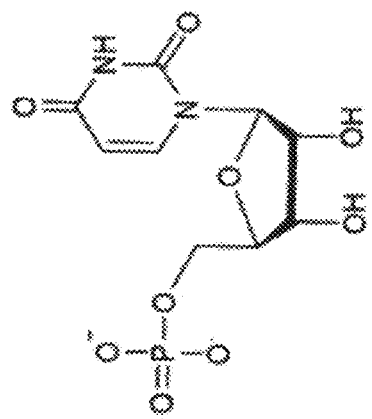

Before the present disclosure, the challenge for DNA sequencing using tunneling spectroscopy has been to identify a unique tunneling spectrum for each nucleotide. Quantum tunneling spectroscopy of DNA nucleotides represents the electronic density of states of the individual nucleobase, nucleoside, and nucleotide. Disclosed herein are methods, devices, and compositions that are used to determine unique fingerprints for modified and unmodified DNA and RNA nucleobases, nucleosides, and nucleotides for use in comparison with electronic signatures of a nucleotide whose identity is unknown (an unknown nucleoside, nucleotide or nucleobase) to aid in identification of the unknown nucleotide. Previous attempts to identify nucleotides from both single stranded (ss) DNA ("ssDNA") and double stranded (ds) DNA ("dsDNA") have been generally unsuccessful in determining unique tunneling spectra for the four DNA nucleobases, nucleosides, and nucleotides.

The disclosed methods, devices, and compositions also aid in alleviating limitations of existing methods of sequencing RNA. The disclosed methods, devices, and compositions may be used in the direct sequencing of RNA, with non-amplified templates at a single molecule level. In many cases, the present disclosure may aid in determining the identity and abundance of RNA molecules obtained from a cell or tissue. Further, the present disclosure's identification of unique electronic tunneling spectra (tunneling data) for nucleotide (DNA/RNA) modifications of single molecules can provide a useful epigenomics technique for early detection of diseases. Epigenomic studies can provide insights into dynamic states of genomes, especially their role in determining disease states and developmental biology.

The disclosed methods, devices, and compositions provide for collection of tunneling data or I-V data that is highly reproducible with little noise. Previous methods suffered from a lack of reproducibility and low signal to noise ratios. The presently disclosed methods, devices, and compositions provide for enhanced data collection in various ways. For example, the disclosed methods, devices, and compositions use an ultrasmooth charged surface that is coated with an ionic polymer. In one embodiment, an Au(111) charged surface may be coated with poly-lysine. The use of an ionic polymer may aid in orienting the nucleic acid backbone, which may provide for tunneling data with greater reproducibility and higher signal to noise ratios than previous methods. In addition, the disclosed methods, devices, and compositions may use a defined environment to collect fingerprint data. For example, the disclosed methods, devices, and compositions may perform quantum tunneling in a high or low pH environment to aid in differentiating various modified and unmodified nucleobases, nucleotides, and nucleosides. The use of a defined environment may also aid in enhancing the tunneling data obtained.

Nanoelectronic tunneling is a quantum-physical process that occurs at the nanoscale. Nanoelectronic tunneling takes advantage of the tendency of the wavefunctions of separate atoms or molecules to overlap. If a voltage bias, or bias, is applied (by increasing or decreasing a potential of a metal tip positioned near the atoms of a substrate in contact with the atoms), tunneling of either electrons or holes between the tip and the atom/molecule can occur, even over a potential barrier. While classical charge conduction nominally occurs from a region of high potential to a region of low potential, where the two regions are separated by downstream potential bias (current flows from high to low potential), quantum tunneling occurs without physical contact (and hence the density of molecular states is unperturbed by measurement) over a potential barrier height, and where the tunneling probability is reduced with increase in barrier height. Electrons can be injected (electron tunneling) or extracted (hole tunneling) to/from one of the molecules due to the wavefunction overlap.

Tunneling current spectra of a nucleotide represents the electronic density of states. Disclosed herein is the use of tunneling current data to create unique fingerprints for use in nucleotide identification. Several attempts have been made by modeling and by experiments to identify and differentiate different nucleotides from both single stranded (ss) DNA and double stranded (ds) DNA, RNA, PNA, other nucleic acid macromolecules, DNA/RNA/PNA nucleotide modifications, nucleic acid structures. However, until the present disclosure, only guanine (G) bases had been partially successfully identified using tunneling microscopy on ssDNA; efforts to identify all four nucleobases were unsuccessful.

Presented herein is a first demonstration of determining unique electronic fingerprints of nucleotides, nucleosides, and nucleobases A, G, T, C and U performed using single-molecule DNA/RNA/PNA sequencing. In addition, unique fingerprints of modified nucleotides/nucleobases are also disclosed. Nucleobase may refer to cytosine (abbreviated as "C"), guanine (abbreviated as "G"), adenine (abbreviated as "A"), thymine (abbreviated as "T"), and uracil (abbreviated as "U"). C, G, A, and T may be found in deoxyribonucleic acid (DNA) and C, G, A, and U may be found in ribonucleic acid (RNA). FIG. 1 shows electronic fingerprints determined by quantum tunneling spectroscopy for nucleotides A, G, C, T and U. The terms nucleoside, nucleotide, and nucleobase, as well as nucleobase/nucleotide and nucleotide/nucleobase, are used interchangeably and refer to natural and synthetic, and modified and unmodified nucleosides, nucleotides, and nucleobases or any combination thereof.

The terms "polynucleotide" and "nucleic acid" are used interchangeably herein.

The disclosed technique uses quantum tunneling data to create an electronic signature for unknown nucleotides, nucleosides, and nucleobases to aid in determining their identity, and may be performed at room temperature (i.e. about 20-25° C.), or at cryogenic temperatures between 1K to 300K. In some cases, the electronic state of the nucleotides, nucleosides, and nucleobases may shift depending on the biophysical condition, or environment, for example the pH at which the nucleotide, nucleoside, or nucleobase is analyzed. In some cases, distinct states of the nucleotide, nucleoside, or nucleobase may be identified at acidic pH (i.e. pH less than about 7). In many embodiments, the pH of the environment used to determine the electronic parameters is less than about 3.

Fingerprints of modified and unmodified nucleotides, nucleosides, and nucleobases may be determined in various biophysical conditions or environments, which may shift their electronic state. This may aid in differentiating nucleobases that may have similar or overlapping parameter values under some biophysical conditions. This may aid in identifying the nucleobase by comparing it to signatures of known nucleobases determined in the same environment. As described above, the fingerprint of a nucleobase may be determined at a given pH and compared to fingerprints of known nucleobases obtained in the same pH. In other environments, the fingerprint may be determined in an environment having specific characteristics other than pH, for example molarity, polarity, hydrophobicity, etc. In various embodiments, the nucleobase may be determined in an environment comprising a given amount of an alcohol, salt, or non-polar solvent or solute.

As disclosed herein, "tunneling current data" or "current data" or "I-V data" refers to current and voltage (bias voltage) data measured in quantum tunneling at various bias voltages. Tunneling current data may refer to I-V, dI/dV and/or I/V$^2$ data acquired from the tunneling current measurement. In most cases, various parameters or values are derived from tunneling current data. Parameters may include values for LUMO, HOMO, Bandgap, $V_{trans+}$ (V), $V_{trans-}$ (V), $\phi_{e-}$ (eV), $\phi_{h+}$ (eV), $m_{e-}/m_{h+}$ and $\Delta\phi$(eV) (described below).

As disclosed herein, "signature" or "electronic signature" refers to three or more values for parameters derived from I-V data collected for a nucleotide of unknown identity. Parameters for use in creating a signature include LUMO, HOMO, Bandgap, $V_{trans+}$ (V), $V_{trans-}$ (V), $\phi_{e-}$ (eV), $\phi_{h+}$ (eV), $m_{e-}/m_{h+}$ and $\Delta\phi$(eV), any three or more of which may be used to create the signature. For example, in some embodiments, an electronic signature of an unknown nucleotide may comprise values for LUMO, HOMO, and Bandgap. In other embodiments, an electronic signature may comprise values for three or more of LUMO, HOMO, Bandgap, $V_{trans+}$ (V), $V_{trans-}$ (V), $\phi_{e-}$ (eV), $\phi_{h+}$ (eV), $m_{e-}/m_{h+}$ and $\Delta\phi$ (eV).

As disclosed herein, "fingerprint" or "electronic fingerprint" refers to three or more values for parameters derived from I-V data collected for a nucleotide of known identity. The parameters selected for creating a fingerprint for a known nucleotide are the same as those selected for creating a signature for the unknown nucleotide, to which the known nucleotide is being compared. Values for a given parameter used in creating an electronic signature may be represented as a value+/−a standard deviation, or as a range of values. Parameters for use in creating a fingerprint include LUMO, HOMO, Bandgap, $V_{trans+}$ (V), $V_{trans-}$ (V), $\phi_{e-}$ (eV), $\phi_{h+}$ (eV), $m_{e-}/m_{h+}$ and $\Delta\phi$ (eV). In some embodiments, an electronic signature for an unknown nucleobase may comprise values for LUMO, HOMO, and Bandgap, and this signature may be compared to electronic fingerprints of known nucleobases, wherein the fingerprints comprise values for the same parameters—LUMO, HOMO, and Bandgap. In other embodiments, the signature may comprise values for three or more of LUMO, HOMO, Bandgap, $V_{trans+}$ (V), $V_{trans-}$ (V), $\phi_{e-}$ (eV), $\phi_{h+}$ (eV), $m_{e-}/m_{h+}$ and $\Delta\phi$ (eV), and may be compared to a fingerprint comprising values for three or more of LUMO, HOMO, Bandgap, $V_{trans+}$ (V), $V_{trans-}$ (V), $\phi$e−(eV), $\phi$h+(eV), me−/mh+ and $\Delta\phi$ (eV).

The disclosed techniques may be used to sequence polynucleic acids, polynucleotides, and other polymeric molecules comprising one or more nucleotide, nucleoside, or nucleobase.

In many cases, a flame-annealed flat, template-stripped ultrasmooth gold (111) ("Au(111)") crystal facet substrate may be used. Designation (111) here indicates the crystal structure of the exposed top surface of the gold atoms. Other orientations can also be used for this purpose (e.g. 100). Ultrasmooth substrates have very low surface roughness, for example less than about 1.0 nm variation from a planar surface. Described herein are methods for obtaining ultrasmooth substrates using a flame annealing and template stripping process as described below. In some embodiments, other substrates may be used. In some embodiments, other conductive substrates may be used, for example graphene, highly ordered pyrolytic graphite (HOPG), atomically-flat freshly cleaved mica with gold (or other metal) coating, other ultrasmooth metals like copper (111), silver etc. In many cases, the substrate should be conductive for the purposes of scanning and quantum tunneling spectroscopy, and smooth for easy identification of single molecules.

In some embodiments, a polynucleotide may be linearized DNA and the polynucleotides may be drawn-out on the disclosed ultrasmooth substrate. This may aid in separating individual nucleotides and reducing their configurational entropy for scanning. This may aid in the study of charge tunneling through the nucleobases, instead of the sugar backbone. In some cases, the substrate may be a charged substrate. For example, where the substrate is gold, a positively charged gold (111) surface may be prepared.

In some embodiments, a positively charged gold substrate is produced for use with an extrusion deposition technique. First, freshly prepared ultrasmooth gold (111) surface is treated in a plasma cleaner (e.g. ozone plasma cleaner), to prepare a uniformly negatively charged surface. In many embodiments the gold may then be treated with an ionic solution, for example a positively charged molecule such as poly-L-lysine, to produce a uniformly coated positively charged gold surface. In some embodiments, the extrusion-deposition technique involves a three step process to disperse elongated linear ssDNA on a gold substrate. In a first step, a gold (111) surface may be charged by treating it with a chemical solution. In some cases, the gold surface may be positively charged by coating it with poly-L-lysine, for example 10 ppm poly-L-lysine solution. Other molecules for use in coating an ultrasmooth surface can include any polycationic polymer, for example polyallylamine hydrochloride, catecholamine polymer, amino silane like aminopropylethoxysilane, or epoxide modified silanes like 3' glycidoxy propyltrimethoxysilane. In other embodiments, electrostatic fixing of the negative charge of the sugar-backbone can be performed by applying a voltage to electrically bond the backbone to the substrate. In some cases, the chemical solution may aid in linking the negatively charged phosphate backbone via electrostatic interaction to a substrate that is positively charged. In some embodiments, the ultrasmooth surface is coated with a positively charged polyelectrolyte. In some embodiments, a positively charged polyelectrolyte comprises positive charges at similar spacing intervals as the phosphates in a nucleic acid molecule (e.g., 0.6-0.8 nm spacing). In some such embodiments, by coating a surface with a positively charged polyelectrolyte with similar spacing of positive charges as phosphate spacing n a nucleic acid, certain advantages may be conferred, including, but not limited to, stronger bonding of deposited nucleic acid, improved order of deposited nucleic acid, improved nucleic acid linearization, and/or reduced entropy of deposited nucleic acid. See, e.g., Rojas et al., 2002, *Langmuir* 18: 1604-1612. In some embodiments, the spatial charge density of copolymerized uncharged acrylamide and positively charged [3-(2-methylpropionamido)propyl] trimethylammonium chloride may be adjusted by changing their co-polymerization ratio. In some embodiments used to sequence a polynucleotide, acidic conditions may aid in de-convoluting nucleotides, for example pyrimidines C or T, and purines G or A.

A second step in the extrusion-deposition technique may involve melting single-stranded DNA (ssDNA). For example, ssDNA may be melted by heating the ssDNA, for example at 95° C. for 5 min. In most embodiments the melted ssDNA is rapidly cooled, which may aid in preventing the formation or re-formation of secondary and/or tertiary structure in the ssDNA. In some embodiments, rapid cooling may involve flash cooling on ice for 5 min. In many embodiments, dsDNA and short mononucleotide ssDNA may not contain tertiary structures; ssDNA longer than about 1 kb may form secondary structures. In many cases, a positively charged surface may help to disrupt or prevent formation of secondary structures.

A third step in the extrusion-deposition process may include extruding the ssDNA onto the gold substrate. In some cases, a translational motion may be used to deposit and draw out a linearized DNA chain on the charged substrate from a DNA dispensing device, for example a pipette.

In some embodiments, a chemically-etched tip may be used for nanoelectronic tunneling. In some embodiments, a platinum-iridium tip (80:20 Pt—Ir) may be used. In other embodiments, other suitable STM tips can also be used. Some other commonly used tips that may be used are tungsten, gold, carbon and platinum metal. Other tips commonly used are Pt, I, W, Au, Ag, Cu, Carbon nanotubes and combinations thereof.

Known and unknown nucleotides are studied by tunneling electrons and holes through the nucleotides. In some cases, the nucleotides studied are linearized, single stranded polynucleotides, as depicted in FIGS. 1A and B.

The tunneling current spectroscopy (current (I)-voltage (V)) may be a direct measure of the local electronic density of states (dI/dV spectra, FIG. 10 and described in more detail below) of the molecule, and may serve to provide a unique electronic fingerprint based on the nucleotide's biochemical structure (FIG. 1).

An electronic signature is obtained for a nucleotide using quantum tunneling, at molecular resolution (FIG. 10A). In some cases, an electronic density of states (DOS) may be obtained from a first derivative of the current-voltage (I-V) spectrum, and a first significant positive and a first significant negative peak assigned as a Lowest Unoccupied Molecular Orbital (LUMO) energy level and a Highest Occupied Molecular Orbital (HOMO) energy level, respectively. In many cases, a first significant peak is a peak that is at least about 30% of the maximum dI/dV, or the first derivative of the current-voltage spectrum (wherein the first derivative represents the density of states for the biomolecule for electron and hole tunneling and greater than about ±1.0 V. In some cases, a peak that occurs at less than about ±1.0V (between 0 and +1.0 V or 0 and −1.0 V) may indicate a conductive substrate or a minor contamination from the environment. The difference between these first peaks may be assigned (designated) as the LUMO/HOMO energy gap or "band gap" (FIG. 10B). The electron tunneling peak (on application of positive bias voltage here) corresponds to the LUMO levels, and the hole tunneling peak (on application of negative bias voltage here) corresponds to the HOMO levels of the molecule. The difference between the LUMO and HOMO levels is the energy bandgap of the molecule.

Additional biophysical parameters which are intrinsic to each nucleobase can also be calculated using the two distinct tunneling regimes (direct tunneling and Fowler-Nordheim tunneling) separated by a transition voltage ($V_{trans}$) at the inflection point. Two main models for quantum tunneling were developed based on the WKB approximation applied to the Schrödinger equation. Simmons model for tunneling between electrodes separated by an insulator (eq. 1) describes the tunneling current at both regimes, its dependence on the applied bias voltage and the effect of the original tunneling barrier.

$$I = \frac{qA}{4\pi^2 \hbar \bar{d}} \left[ \bar{\phi} e^{-\left(\frac{2\bar{d}\sqrt{2m^*\bar{\phi}}}{\hbar}\right)} - (\bar{\phi} + qV) e^{-\left(\frac{2\bar{d}\sqrt{2m^*\bar{\phi}+qV}}{\hbar}\right)} \right] \quad \text{(eq. 1)}$$

Where $\bar{\phi}$ is the average barrier height which is proportional to the applied voltage as the shape of the tunneling barrier changes from rectangular to trapezoidal and triangular, $m^*$ is the effective electron mass, h the reduced Plank's constant, $\bar{d}$ is the mean tunneling distance, A is the effective tunneling area, q is the elementary charge and V is the applied bias voltage. The model is generic for any shape of tunneling barrier as only the average barrier height is required ($\bar{\phi}$).

The other analytical approach used for quantum tunneling is based on Stratton model (eq. 2), also derived from WKB approximation. While both Simmons and Stratton model starts from the same current density description, they took different approximations for solving the tunneling probability integral which yields to different equation sets. Stratton equation for describing quantum tunneling is:

$$I = \frac{4mqA}{\hbar^3 c^2(V)} \left[ \frac{\pi c(V) kT}{\sin(\pi c(V) kT)} \right] [1 - e^{-c(V)qV}] e^{-b(V)} \quad \text{(eq. 2)}$$

Where m is the electron mass, k is the Boltzmann constant, T is the temperature and b(V) and c(V) are two parameters resultant from the Taylor expansion of the tunneling probability and defined as:

$$b = \alpha \int_{x_1}^{x_2} (\phi - \xi)^{\frac{1}{2}} dx \text{ and } c = \frac{1}{2} \int_{x_1}^{x_2} (\phi - \xi)^{-\frac{1}{2}} dx$$

Where $\alpha = 2\sqrt{2m^*}/h$ and $x_1$ and $x_2$ are the positions where $\phi - \xi = 0$ for each side of the tunneling gap, $\xi$ is the Fermi energy of the electrode and $\phi$ is the energy barrier (x and V dependent).

While these parameters can be fitted experimentally with temperature dependence of tunneling current, the model was simplified to the form of $1 \propto \sin h(qV\tau/h)$, as it describes the sequencing conditions used here. Using this relationship, we derived the minimum ($V_{trans}$) on the $\ln(I/V^2)$ vs. $V^{-1}$ plot as the following equation within a few percent error:

$$V_{trans} \approx \frac{2\hbar}{q\sqrt{m^*}} \frac{\sqrt{2\phi}}{d} \quad \text{(eq. 3)}$$

Using Simmons model, a simplified Fowler-Nordheim equation is derived for high bias voltages ($qV > \phi_0$). This takes the following form:

$$\ln\left(\frac{I}{V^2}\right) \propto -\frac{4d\sqrt{2m^*\phi_0^3}}{3\hbar q} \left(\frac{1}{V}\right) \quad \text{(eq. 4)}$$

Combining both models, one can derive expressions for the direct calculation of the original barrier height ($\phi_0$) and the "effective" tunneling distance ($d\sqrt{m^*}$) using experimental data extracted directly from the FN plot:

$$\phi_0 = \sqrt{\frac{V_{trans} \cdot 3 \cdot S}{16}} \quad d\sqrt{m^*} = \frac{3 \cdot S \cdot \hbar q}{16\sqrt{2m_0 \cdot \phi_0^3}}$$

Where S is the slope of the $\ln(I/V^2)$ vs. $V^{-1}$ corresponding at high bias voltages ($qV > \phi_0$). Note that both Stratton and Simmons use the same approximation of the Schrödinger (WKB) and the only difference come on the treatment of tunneling probability integrals. Hartman made a comparison of both models against the exact solution of WKB approximations and both Stratton and Simmons model are within a few percentage of error from the exact solution. With this approximation, using both models, experimental spectroscopic data can be fit on either model that would be impossible otherwise due to intractability of the non-linearity of both models.

This method allows the quantitative comparison of nucleotides by examining up to 9 parameters (HOMO Voltage, LUMO Voltage, Energy Bandgap, $V_{trans, e-}$, $V_{trans, h+}$, $\phi_{0,e-}$, $\phi_{0,h+}$, $\Delta\phi$ and $m_{eff\ e-}/m_{eff\ h+}$). In many embodiments, the signatures may be determined by analyzing values for at least three parameters. In most embodiments, more than three parameters are used to determine a signature. For example, four, five, six, seven, eight, or nine parameter values may be used to determine a signature for comparison to a fingerprint comprising the same parameter values.

Nucleotide fingerprints and signatures are determined by submitting the nucleotide to quantum tunneling and then collecting and analyzing the tunneling current data. In many cases, in order to create a quantum tunneling nucleotide fingerprint, tunneling current data is collected from about 15 to about 50 points on an individual nucleotide molecule (for example a single molecule of adenine). In addition, quantum tunneling data is collected for about 20 different individual molecules, which may aid in creating a statistically accurate fingerprint of the nucleotide.

Probability density curves (Voltage, V, or Energy, eV, versus probability density function (dI/dV)) of DNA several known nucleotides have been determined. Several probability density curves are shown in FIGS. 4a, 4b, 4c, 4f, 8d, 8e, 12, 14, 16, 21, 22, and 24b. These curves are statistical distributions of independent measurements, which have been fitted to a normalized sum of Gaussian curves (equation S1, below. Ni: normalization constant, V: applied bias voltage, μi: mean, σi: standard deviation).

$$P(V) = \Sigma_i \left\{ N_i \exp\left[ \frac{-(V - \mu_i)^2}{2\sigma_i^2} \right] \right\} \quad \text{Equation S1}$$

These parameters may be used to create an electronic fingerprint for a given nucleotide consisting of HOMO level, LUMO level, and energy gap (Band Gap). In many embodiments, nucleobase fingerprints of known nucleobases may be used to analyze the quantum tunneling signature collected from an unknown nucleotide or polynucleotide DNA molecule to determine the nucleotide's identity and the polynucleotide's sequence.

Nucleic acids biochemistry may be defined by the environment where the nucleic acid is found. In some cases, the surrounding pH may affect the structure of a nucleic acid, for example a nucleobase/nucleotide. In some embodiments altering the pH may result in the nucleobase having different structures. This effect may occur above and/or below a nucleobase's $pK_a$, as shown in FIG. 11. Additionally, besides acid-base behavior, other biochemical changes can occur at extreme pH (either acidic or basic). For instance, thymine can form tautomers at acidic pH where enolized-T is predominant over the keto form.

Figure 12:
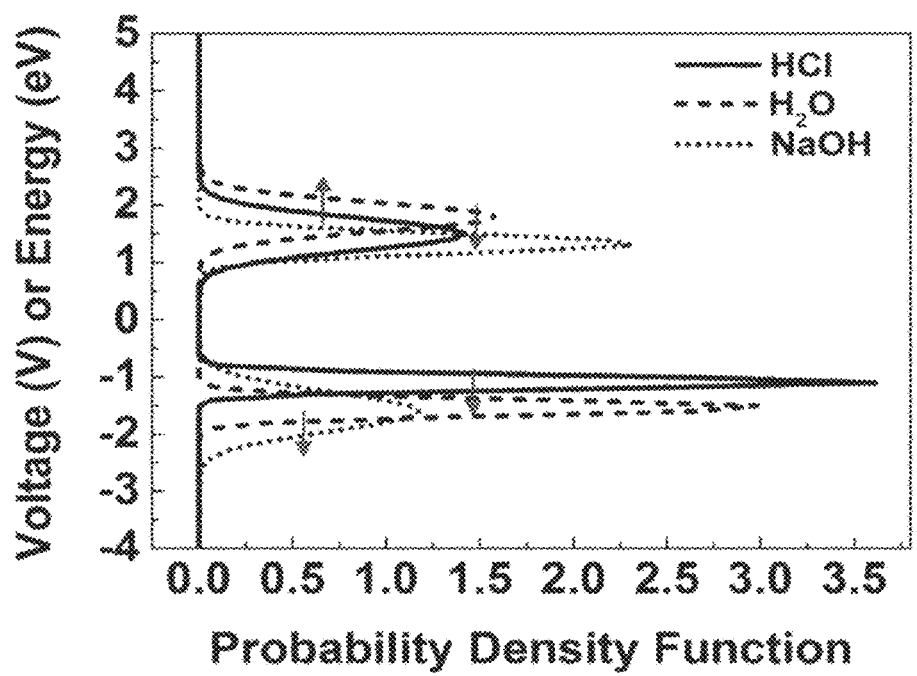
FIG. 12: Effect of pH on guanine LUMO/HOMO levels. Distribution of LUMO (positive peak) and HOMO (negative peak) levels for Guanine deposited on Au (111) surface, at acidic (washed with 0.1 M HCl), neutral ($H_2O$) and basic (0.1 M NaOH) pH. Arrows indicate the shift of LUMO and HOMO levels between acidic, neutral and basic conditions. Guanine exhibits three biochemical structures at acidic (pH is below first pKa~3.2-3.3), neutral and basic conditions (above its second pKa~9.2-9.6). Likely hole trapping in isomers results in a steady increase of the HOMO level (harder to tunnel holes) as the pH increases (from acidic, to neutral to basic condition). However, multiple resonance structures at the acidic and basic conditions (FIG. 11) results in easier electron tunneling (and lower LUMO levels), compared to neutral condition. Moreover, further electrostatic repulsion at basic condition (due to pKa2) improves electron tunneling probability, and results in a further decrease of LUMO level for basic pH.
Figure 13B:
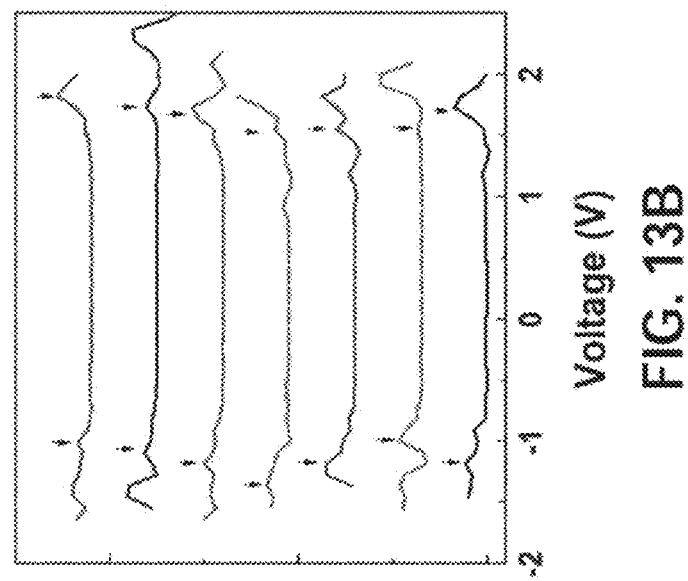
Figure 13A:
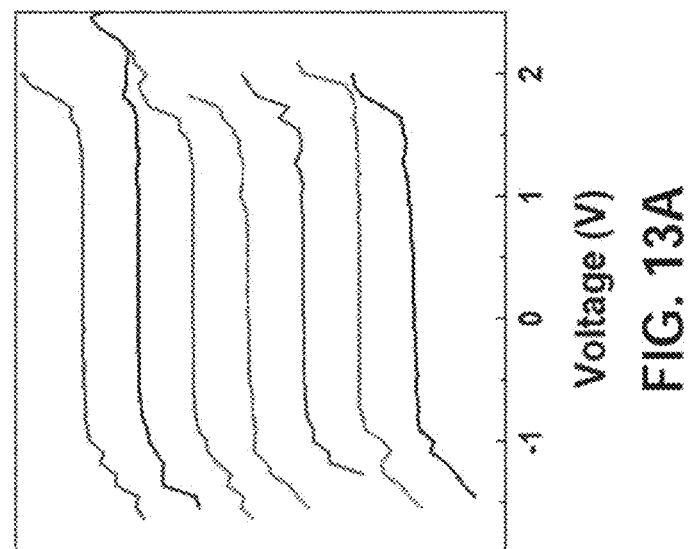
Figure 14:
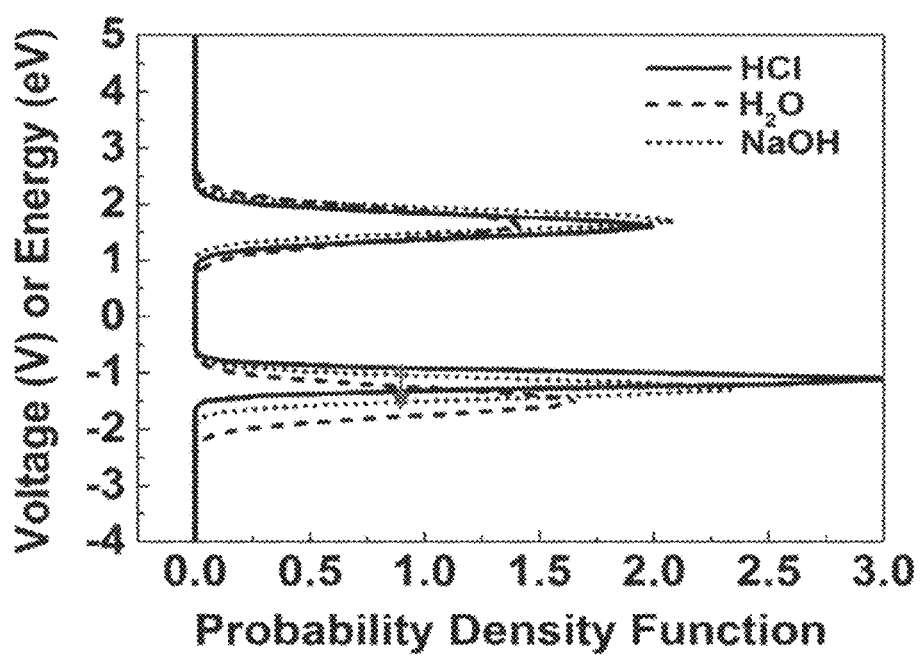
FIG. 14: Effect of pH on adenine LUMO/HOMO levels. Distribution of LUMO (positive peak) and HOMO (negative peak) levels for Adenine deposited on Au (111) surface, at acidic (washed with 0.1 M HCl), neutral ($H_2O$) and basic (0.1 M NaOH) pH. While Adenine has multiple resonance structures at any pH conditions (both charged and uncharged), significant effect of pH on its tunneling probability is not observed (due to dissipation of the charge amongst the resonance structures). Minor increase in HOMO level with increase in pH can be attributed to easier hole tunneling at acidic pH (due to the positive charge).
Figure 15A:
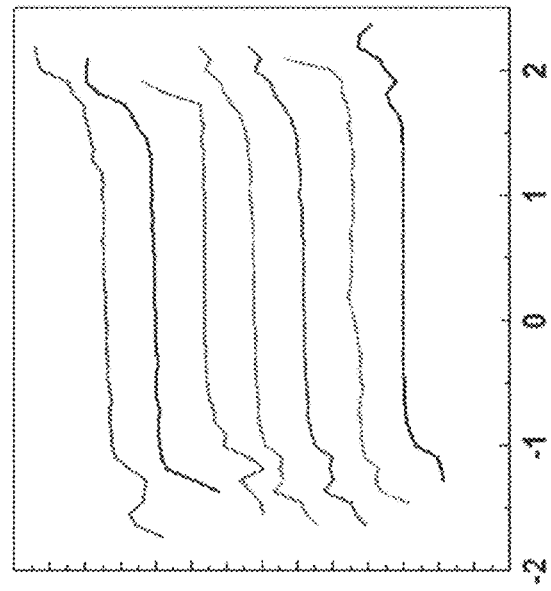
FIGS. 15A-E: Raw data and statistics of adenine: (a) Raw current-voltage (I-V) curves for Adenine at acidic conditions. (b) Raw spectra or dI/dV of (a), arrows indicate identified HOMO/LUMO levels as the first significant negative/positive peak on each spectra. (c-e). Histograms of the positions of HOMO (c), LUMO (d) and Energy Gap (e) for adenine, superimposed by a normal probability density function (indicated by curve, also shown in FIG. 4a,b) fitted to the data set. The shaded box in each of 15C, 15D, and 15E indicates the area of the curve comprising the mean±standard deviation.
Figure 15B:
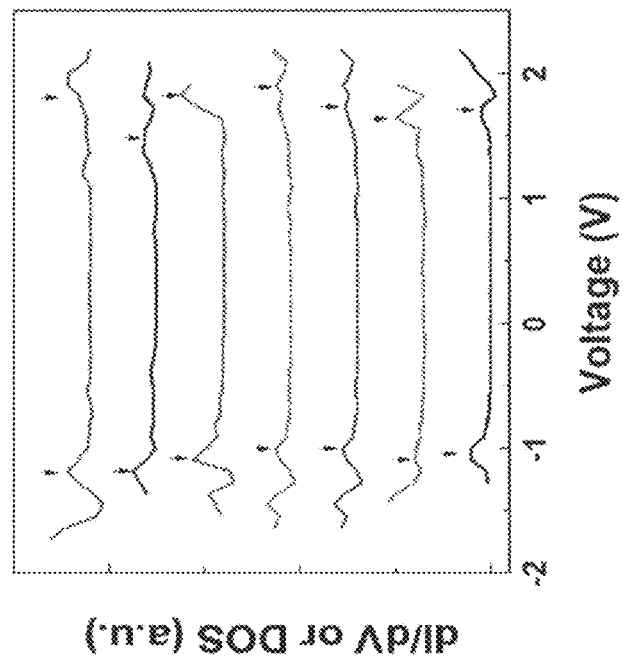
Figure 15E:
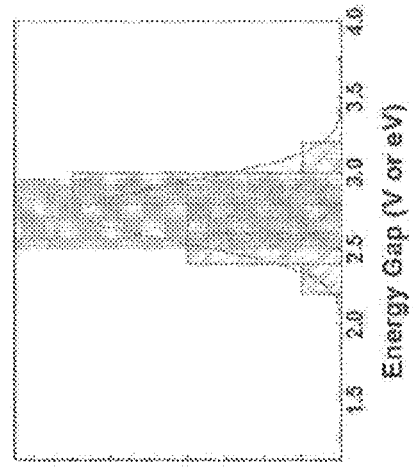
Figure 15D:
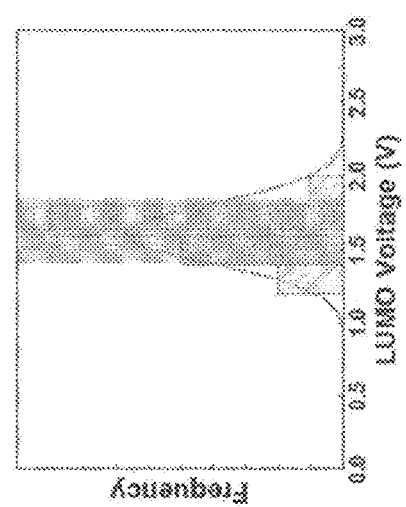
Figure 15C:
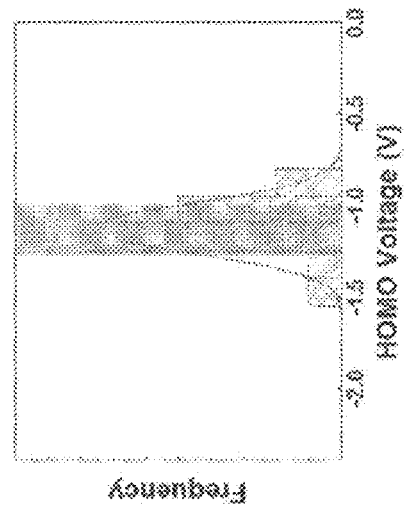
Figure 16:
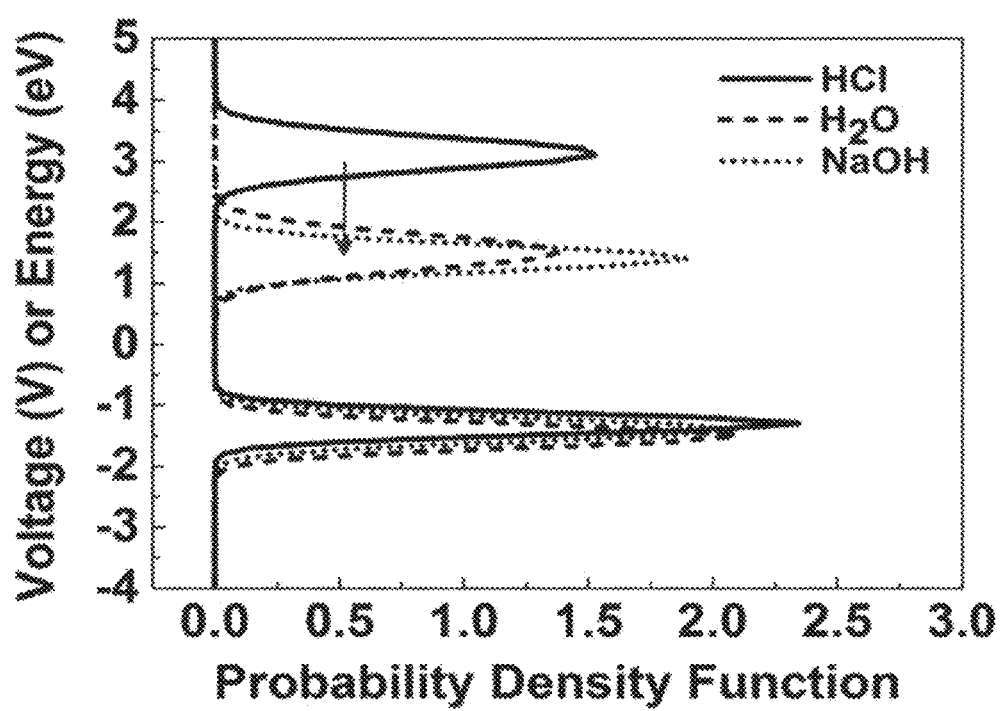
FIG. 16: Effect of pH on cytosine LUMO/HOMO levels. Distribution of LUMO (positive peak) and HOMO (negative peak) levels for Cytosine, deposited on Au (111) surface at acidic (washed with 0.1 M HCl), neutral ($H_2O$) and basic (0.1 M NaOH) pH. Cytosine has a clear pH effect with two main structures: above its pKa~4.4, no difference appears between neutral and basic conditions. However, its protonated form at acidic conditions show likely electron trapping effect, increasing the LUMO energy level.
Figure 17B:
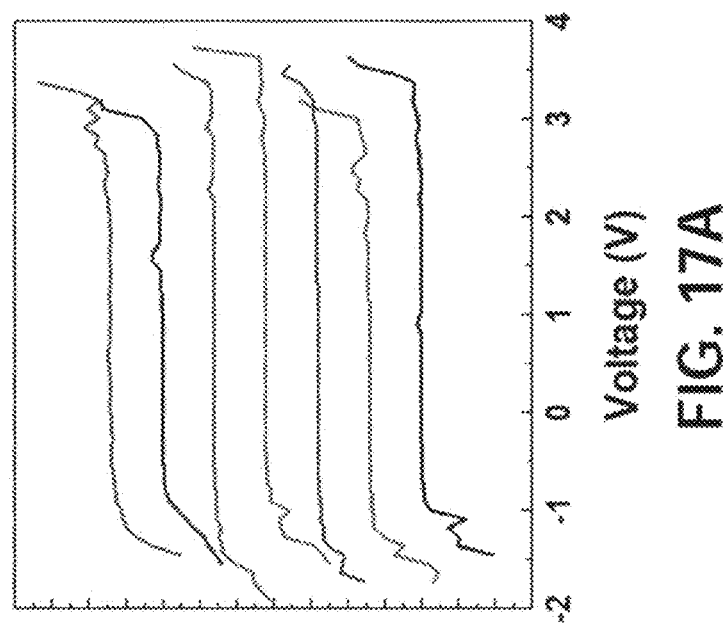
FIGS. 17A-E: Raw data and statistics of cytosine: (a) Raw current-voltage (I-V) curves for Cytosine at acidic conditions. (b) Raw spectra or dI/dV of (a), arrows indicate identified HOMO/LUMO levels as the first significant negative/positive peak on each spectra. (c-e). Histograms of the positions of HOMO (c), LUMO (d) and Energy Gap (e) for Cytosine, superimposed by a normal probability density function (indicated by curve, also shown in FIG. 4a,b) fitted to the data set. The shaded box in each of 17C, 17D, and 17E indicates the area of the curve comprising the mean±standard deviation.
Figure 17A:
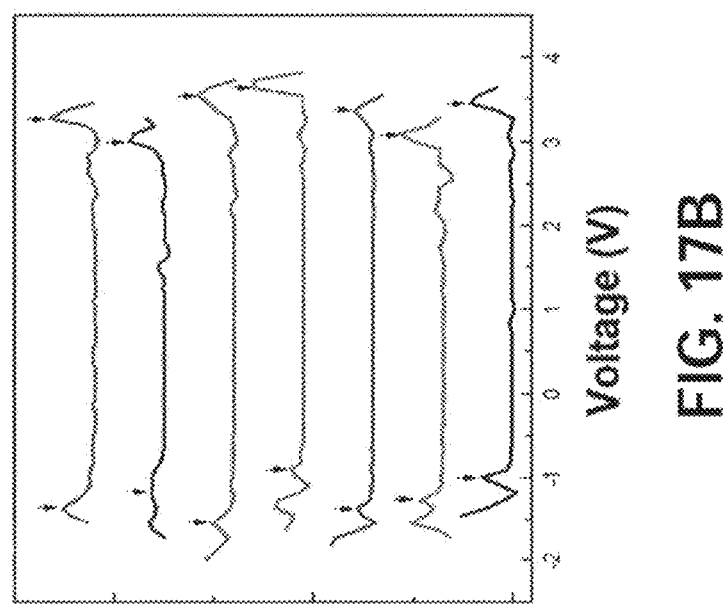
Figure 17E:
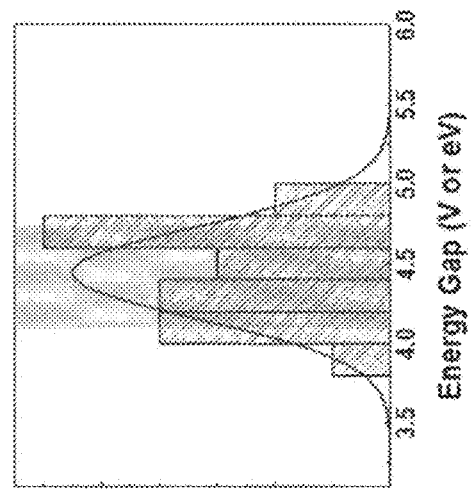
Figure 17D:
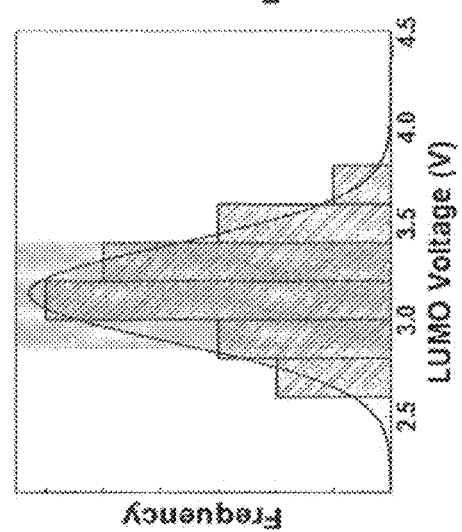
Figure 17C:
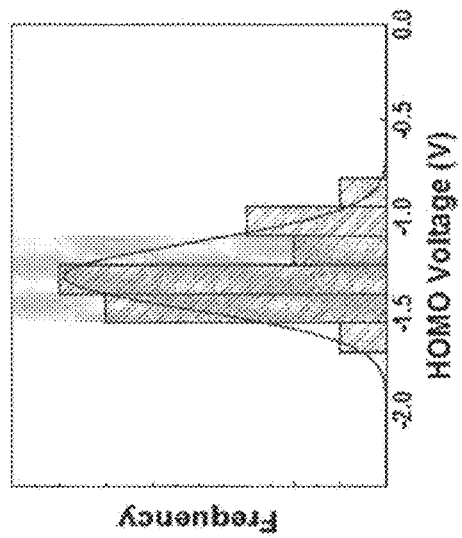
Figure 18A:
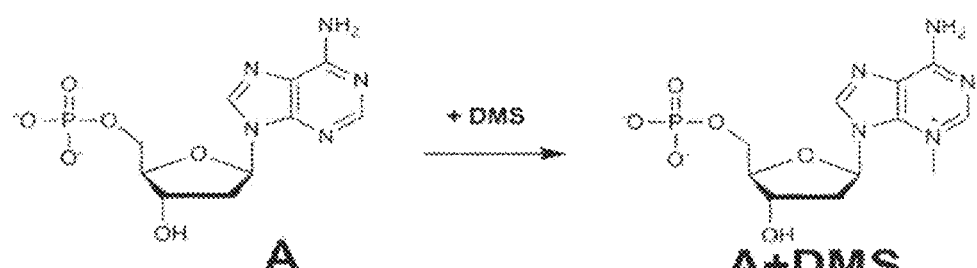
FIGS. 18A-D: Identification of single nucleotide modifications using QM-Seq. (a) Reaction products of methylation of Adenine with DMS. (b) Reaction products of methylation of Guanine with DMS. (c) Boxplot of HOMO and LUMO energy levels distribution for adenine and methylated adenine deposited on poly-lysine modified Au (111) surface, under acidic conditions. Addition of a methyl group shifts the HOMO level by reducing the hole tunneling probability. (d) Boxplot of HOMO and LUMO energy levels distribution for guanine and methylated guanine deposited on poly-lysine modified Au (111) surface, under acidic conditions.
Figure 18B:
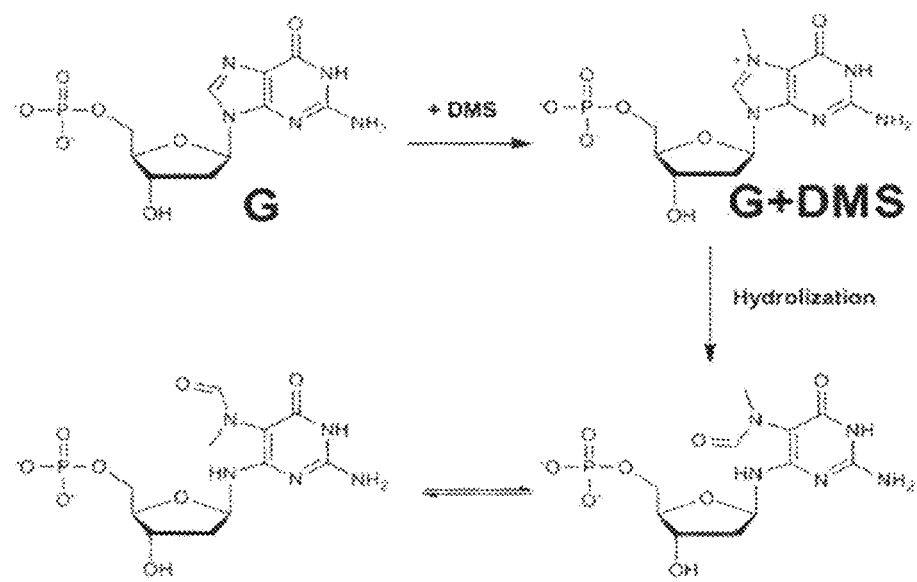
Figure 18D:
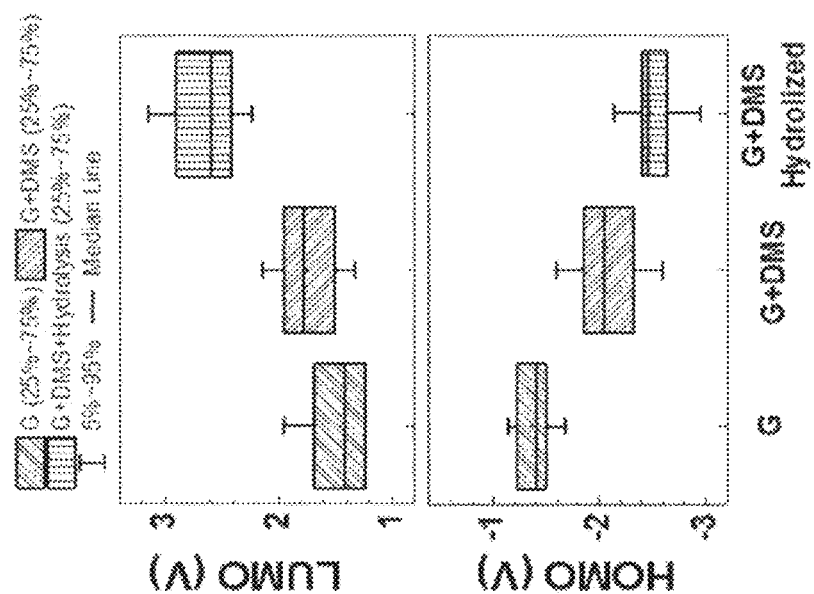
Figure 18C:
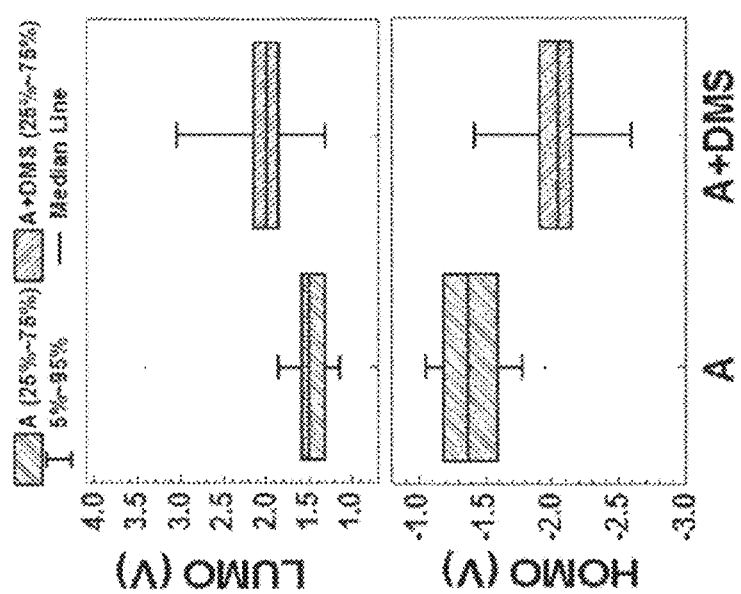
Figure 19B:
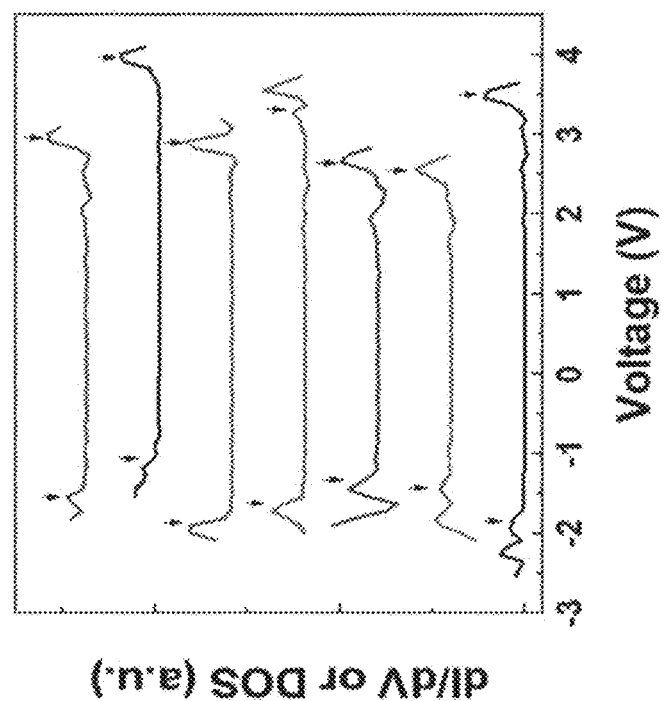
FIGS. 19A-E: Raw data and statistics of Thymine: (a) Raw current-voltage (I-V) curves for Thymine at acidic conditions. (b) Raw spectra or dI/dV of (a), arrows indicate identified HOMO/LUMO levels as the first significant negative/positive peak on each spectra. (c-e). Histograms of the positions of HOMO (c), LUMO (d) and Energy Gap (e) for Thymine (bars), superimposed by a normal probability density function (indicated by curve, also shown in FIG. 4a,b) fitted to the data set. The shaded box in each of 19C, 19D, and 19E indicates the area of the curve comprising the mean±standard deviation.
Figure 19A:
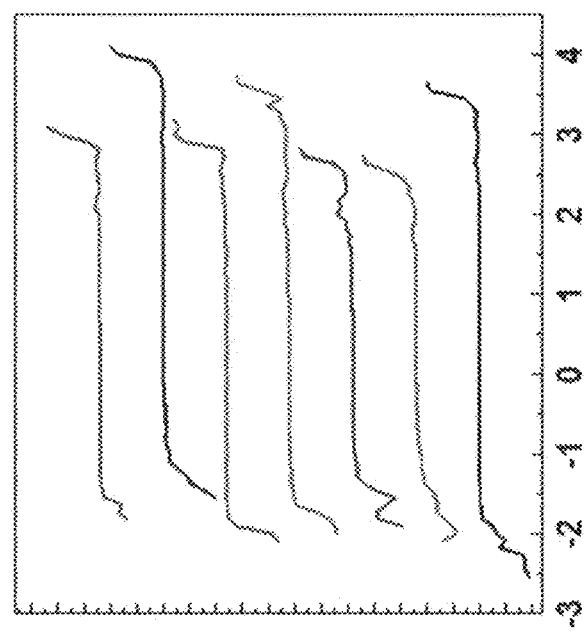
Figure 19E:
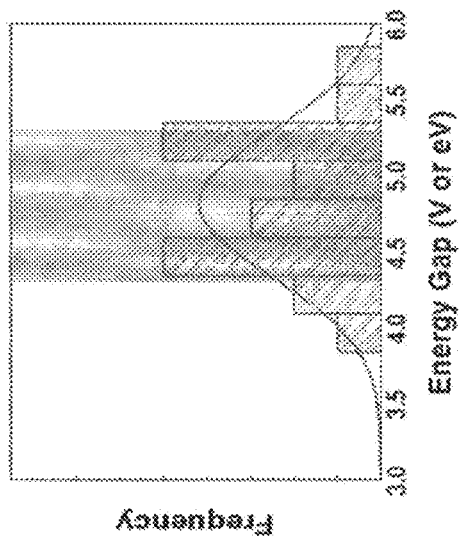
Figure 19D:
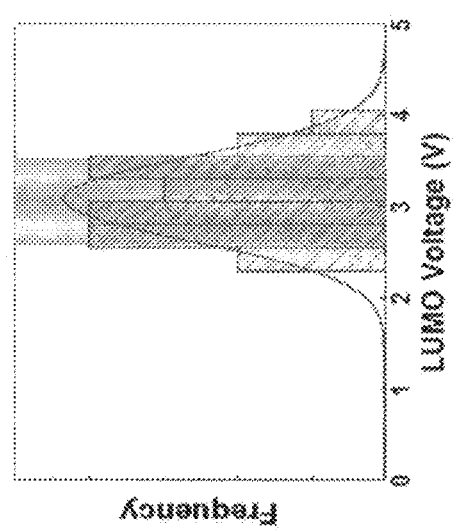
Figure 19C:
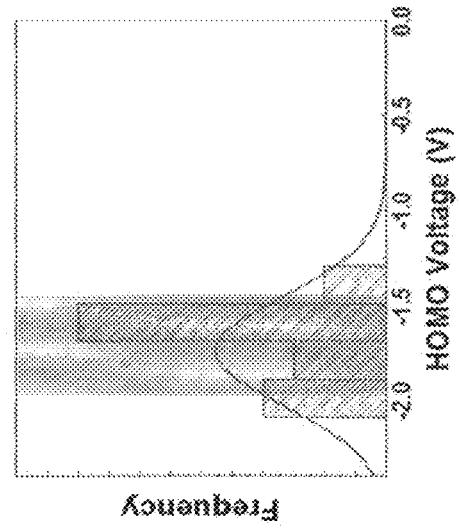
Figure 20:
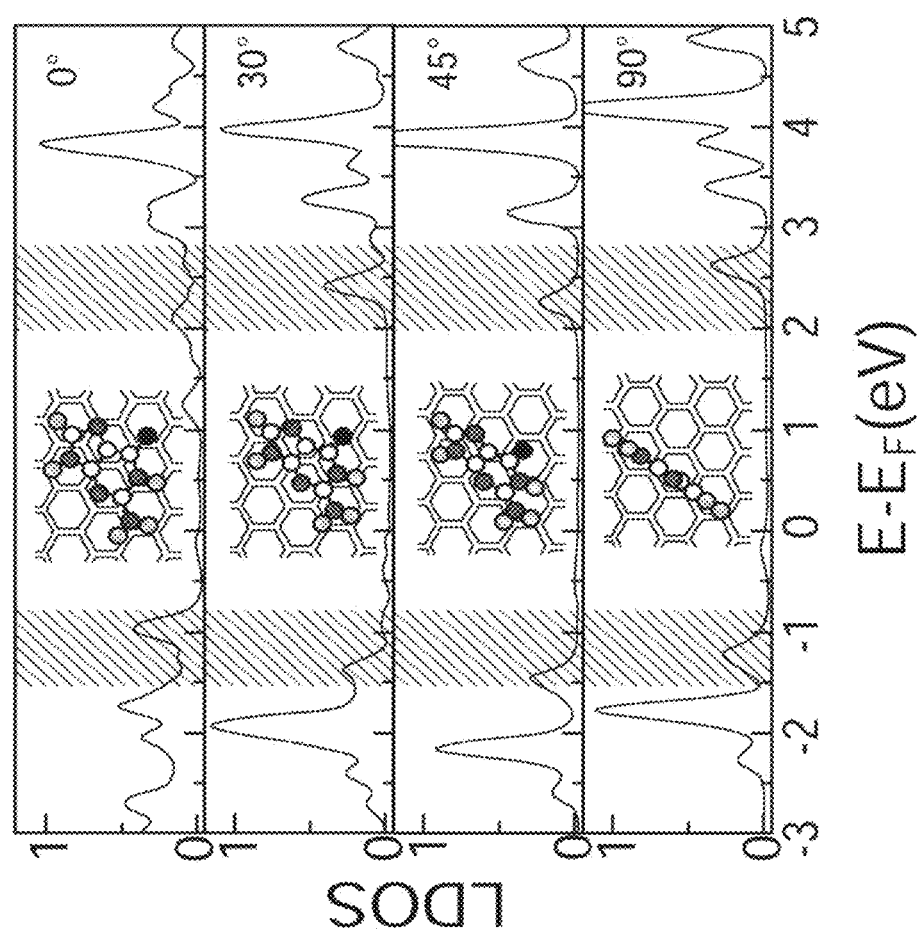
FIG. 20: Configurational energy contribution to HOMO, LUMO and Energy gap dispersion for adenine (nucleobase) adsorbed on graphene—Adapted from Ahmed et al. which describes DFT simulation of a nucleobase at different configurations positioned on top of a conductive substrate and its contribution to the local density of states based on DFT theory. Lines are local density of states (LDOS) of nitrogen atom adsorbed on graphene at different angles (conformation superimposed in the center). Yellow-shaded regions correspond to dominant peak near Fermi level. Grey-shadow boxes represent the distribution of predominant peak (positive and negative) near the Fermi level considering all possible conformations (from 00 to 900).
Figure 21B:
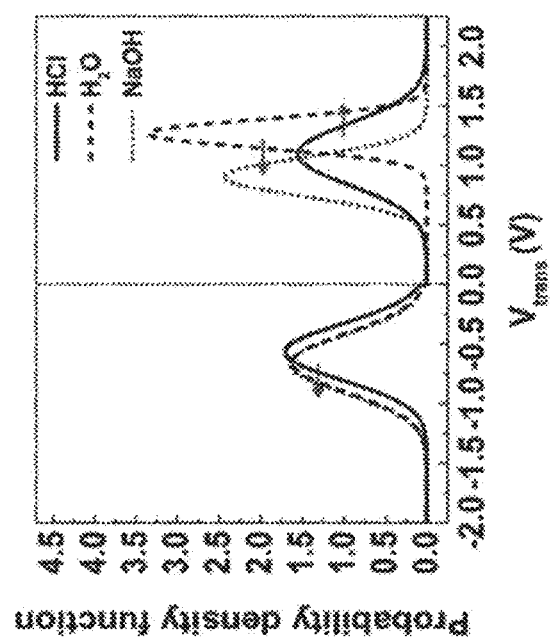
FIGS. 21A-D: Effect of pH on electron and hole transition voltage (between tunneling and field emission regimes), from Fowler-Nordheim plot. $V_{trans}$ for electron ($V_{trans,e-}$) and hole ($V_{trans,h+}$) is shown for (a) Adenine (A), (b) Guanine (G), (c) Cytosine (C), and (d) Thymine (T). Arrows indicate the shift of $V_{trans,e-}$ and $V_{trans,h+}$ between acidic (HCl), neutral ($H_2O$) and basic (NaOH) conditions. All these transitions mimic the respective changes in LUMO and HOMO levels, thereby confirming the role of $V_{trans}$ as one potential biophysical figure of merit.
Figure 21A:
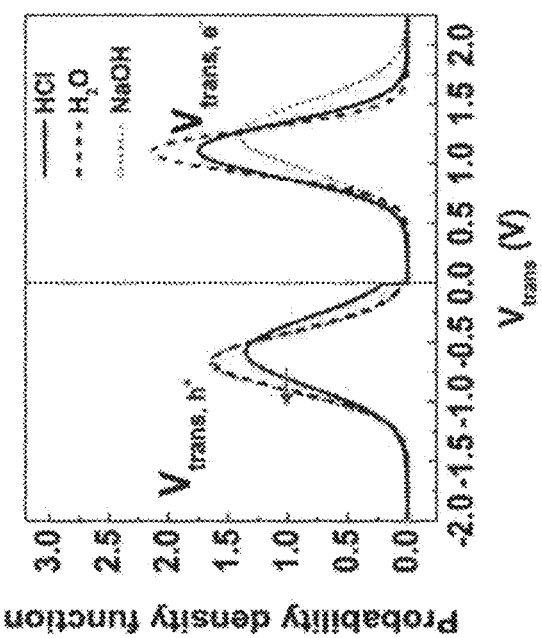
Figure 21D:
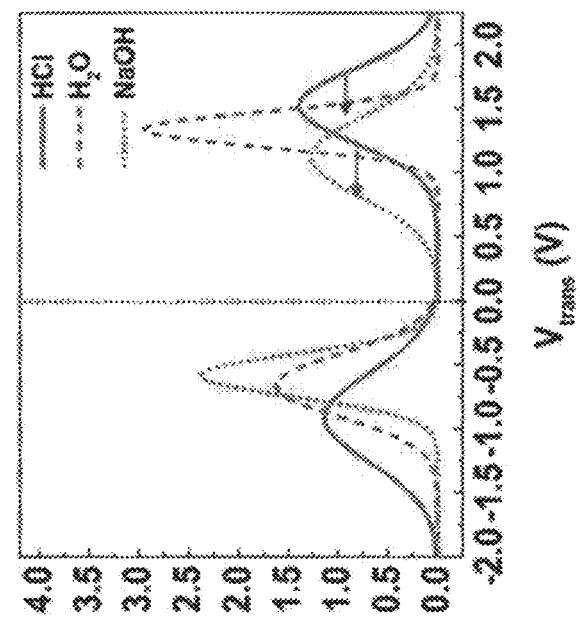
Figure 21C:
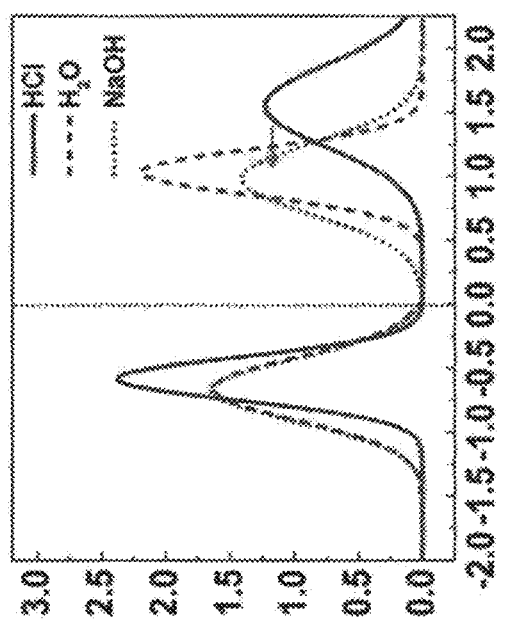

The relative charge of DNA nucleotides can facilitate either electron or hole tunneling depending on the system pH. For example, in some embodiments a positively charged DNA nucleotide species may facilitate hole tunneling and increase the energy level for electron tunneling (LUMO), and a negatively charged species may exhibit the opposite behavior (FIG. 12, 14). This effect can be observed on the spectra shift for a guanine nucleotide along its two $pK_a$ (FIG. 12) where the nucleotide transitions between positively charged structure under acidic pH, to a negatively charged structure at basic pH. In some embodiments, electrostatic interactions may, therefore, change the probability of the charge tunneling (increases on charge repulsion), resulting in different (lower) respective LUMO and HOMO levels.

Tunneling signatures (or fingerprints) for individual nucleotides may differ under different environmental conditions, for example under different pH conditions. In many cases, electron/hole tunneling current through a nucleotide is collected under different environmental conditions. Differences in quantum tunneling signatures under different environmental conditions, may in some cases be due to the presence of keto-enol tautomers of the nucleobases, which may differ under different pH conditions (FIG. 11 and as discussed below). The presence or absence of a specific keto-enol tautomer may lead to separation of electron/hole tunneling probability between different nucleobases, for example between purines (A,G) and pyrimidines (C,T).

The charge density of a nucleotide may aid in determining the energy increase/decrease for these effects. In some cases, purines, which may have several conjugated structures, may have a local charge on any atom that is significantly reduced in comparison with pyrimidines, which may have the charge localized on a single atom (FIG. 11). In some embodiments, the conjugation effect may have a significant impact on the tunneling energy shifts and may be readily observed in acidic conditions (FIG. 4C, 12, 14, 16), for example, where purines may exhibit a significantly smaller effect than pyrimidines (e.g. adenine data in FIG. 14).

In many cases, the use of HOMO-LUMO and energy gap parameters may aid in distinguishing purines (A,G) from pyrimidines (C,T) under acidic conditions based on the energy gap (there is about a 1.7-2 eV difference between the purines A, 2.73 eV and G 2.58 eV and the pyrimidines C, 4.43 eV and T, 4.82 eV) and LUMO level (about 1.5 eV difference between the purines A, 1.61 V and G 1.49 V and the pyrimidines C, 3.13 V and T, 3.08 V). In some embodiments, C and T may be distinguished or de-convoluted based on their HOMO energy level difference (about 0.45 eV difference between C, −1.30 V and T, −1.74 V). In further embodiments A and G can be distinguished/differentiated/de-convoluted using their LUMO levels at basic pH (about 0.40 eV difference between A, 1.72 V and T, 1.33 V). Characteristic LUMO, HOMO, and Band Gap values for the nucleobases A, T, G, and C are presented in Table I. Table I shows these values determined at neutral, acidic and basic pH environments. Thus, in some embodiments, the identity of an unknown nucleotide may be determined by collecting quantum tunneling data on the nucleotide at one or more pH values (acid, basic, and neutral), determining the LUMO, HOMO, and Band Gap values for that nucleotide, and comparing those values to values previously determined for nucleotides of known identity.

TABLE I

Summary of LUMO, HOMO and band gap energy levels for A, C, G, and T on bare Au(111) surface under different pH conditions. Values correspond to mean ± standard deviation.

| | Voltage (V)/<br>Energy (eV) | HCl (acidic) | H₂O (neutral) | NaOH (basic) |
|---|---|---|---|---|
| A | LUMO (V) | 1.61 ± 0.20 | 1.74 ± 0.28 | 1.72 ± 0.19 |
|   | HOMO (V) | −1.12 ± 0.13 | −1.51 ± 0.24 | −1.28 ± 0.17 |
|   | Band Gap (eV) | 2.73 ± 0.20 | 3.25 ± 0.22 | 3.00 ± 0.22 |
| C | LUMO (V) | 3.13 ± 0.26 | 1.61 ± 0.29 | 1.41 ± 0.21 |
|   | HOMO (V) | −1.30 ± 0.17 | −1.53 ± 0.19 | −1.40 ± 0.19 |
|   | Band Gap (eV) | 4.43 ± 0.29 | 3.11 ± 0.24 | 2.82 ± 0.24 |
| G | LUMO (V) | 1.49 ± 0.28 | 1.89 ± 0.25 | 1.33 ± 0.17 |
|   | HOMO (V) | −1.09 ± 0.11 | −1.53 ± 0.13 | −1.60 ± 0.34 |
|   | Band Gap (eV) | 2.58 ± 0.32 | 3.43 ± 0.24 | 2.94 ± 0.42 |
| T | LUMO (V) | 3.08 ± 0.45 | 2.31 ± 0.20 | 1.58 ± 0.23 |
|   | HOMO (V) | −1.74 ± 0.29 | −1.30 ± 0.22 | −1.46 ± 0.39 |
|   | Band Gap (eV) | 4.82 ± 0.48 | 3.70 ± 0.25 | 3.04 0.43 |

TABLE II

Summary of LUMO, HOMO and band gap energy levels for A, C, G, and U on modified Au(111) surface under different pH conditions. Values correspond to mean ± standard deviation.

| | Voltage (V)/<br>Energy (eV) | HCl (acidic) | H₂O (neutral) | NaOH (basic) |
|---|---|---|---|---|
| A | LUMO (V) | 1.46 ± 0.21 | 1.49 ± 0.28 | 1.43 ± 0.22 |
|   | HOMO (V) | −1.46 ± 0.23 | −1.40 ± 0.28 | −1.40 ± 0.26 |
|   | Band Gap (eV) | 2.93 ± 0.29 | 2.89 ± 0.38 | 2.83 ± 0.32 |
| C | LUMO (V) | 2.21 ± 0.22 | 1.59 ± 0.15 | 1.76 ± 0.24 |
|   | HOMO (V) | −1.37 ± 0.26 | −1.70 ± 0.31 | −1.68 ± 0.26 |
|   | Band Gap (eV) | 3.57 ± 0.25 | 3.29 ± 0.37 | 3.44 ± 0.40 |
| G | LUMO (V) | 1.50 ± 0.18 | 1.36 ± 0.32 | 1.53 ± 0.27 |
|   | HOMO (V) | −1.33 ± 0.16 | −1.73 ± 0.24 | −1.31 ± 0.34 |
|   | Band Gap (eV) | 2.83 ± 0.21 | 2.73 ± 0.33 | 2.83 ± 0.36 |
| U | LUMO (V) | 2.03 ± 0.25 | 2.59 ± 0.67 | 1.62 ± 0.37 |
|   | HOMO (V) | −1.49 ± 0.25 | −1.23 ± 0.23 | −1.51 ± 0.33 |
|   | Band Gap (eV) | 3.53 ± 0.32 | 3.82 ± 0.73 | 3.13 ± 0.43 |

Guanine:

In many cases, guanine may exhibit three distinct biochemical structures at acid conditions (acidic pH is below first $pK_a$~3.2-3.3), neutral conditions and basic conditions (above its second $pK_a$~9.2-9.6). In some cases, hole trapping in isomers may result in a steady increase of the HOMO level (i.e. harder to tunnel holes) as the pH increases (from acidic, to neutral to basic condition). In some embodiments, multiple resonance structures at the acidic and basic conditions (FIG. 11) may result in easier electron tunneling (and lower LUMO levels), compared to neutral condition. In some cases, further electrostatic repulsion at basic condition (due to $pKa_2$) can improve electron tunneling probability, and may result in a further decrease of LUMO level for basic pH.

Adenine:

In many cases, adenine may exhibit multiple resonance structures at any pH condition (both charged and uncharged). In most cases, pH changes do not significantly affect adenine's tunneling probability. In some cases, this lack of pH effect may be due to dissipation of the charge amongst the resonance structures. In some cases, adenine may exhibit an increase in HOMO level with increase in pH, which in some cases may be attributed to easier hole tunneling at acidic pH (due to the positive charge).

Cytosine:

In many embodiments, cytosine may display distinct pH effects with two main structures. For example, in some embodiments above its $pK_a$~4.4, cytosine may exhibit no difference between neutral and basic conditions. In other cases, where cytosine is in its protonated form at acidic conditions, it may exhibit an electron trapping effect, which may result in increased LUMO energy level.

Figure 4A:
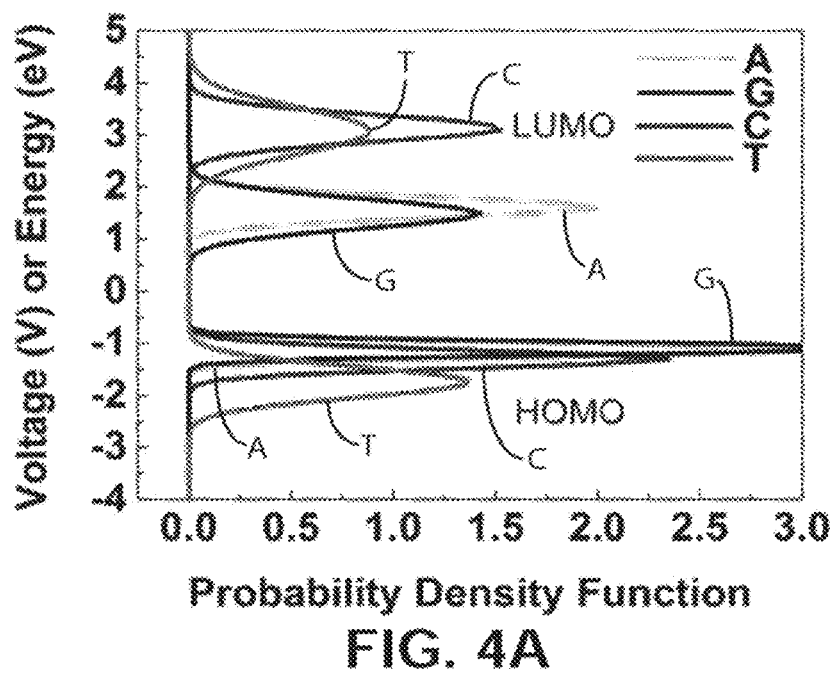
FIGS. 4A-F: Electronic fingerprints obtained using STM-STS for DNA nucleotides. (a) Distribution of HOMO (negative) and LUMO (positive) levels for A, G, C and T, under acidic conditions (surface washed with 0.1 M HCl). A clear separation of LUMO levels (positive voltage peaks) was used to identify pyrimidines (C, T) from purines (A, G), and differences in HOMO levels was used to separate pyrimidines (C from T). (b) Energy gap between LUMO and HOMO energy levels under acidic conditions. (c) HOMO/LUMO levels of Thymine at acidic (HCl), neutral (H$_2$O) and basic (NaOH) pH conditions. Arrows indicate shifts of the LUMO levels between acid, neutral and basic pH conditions. (d) Biochemical structures of Thymine at different pH conditions including keto-enol tautomerization at acidic conditions, and acid-base behavior between neutral and basic conditions. (e) Electron Fowler-Nordheim plot of Thymine at acidic conditions, characterized by its transition voltage ($V_{trans}$) and the slope of triangular tunneling (proportional to the tunneling energy barrier). At very small voltages, the tunneling becomes trapezoidal/rectangular and hence shows deviation from a linear slope(the slope becomes logarithmic). (f) Probability density function of transition voltage for electron ($V_{trans,e-}$) and hole ($V_{trans,h+}$) at acidic conditions for all four nucleotides. $V_{trans,e-}$/$V_{trans,h+}$ and slope (S) of the Fowler-Nordheim tunneling show the same behavior as HOMO/LUMO levels and their energy bandgap (also referred to as "Energy gap," "Band Gap," or "Bandgap"), respectively.
Figure 4B:
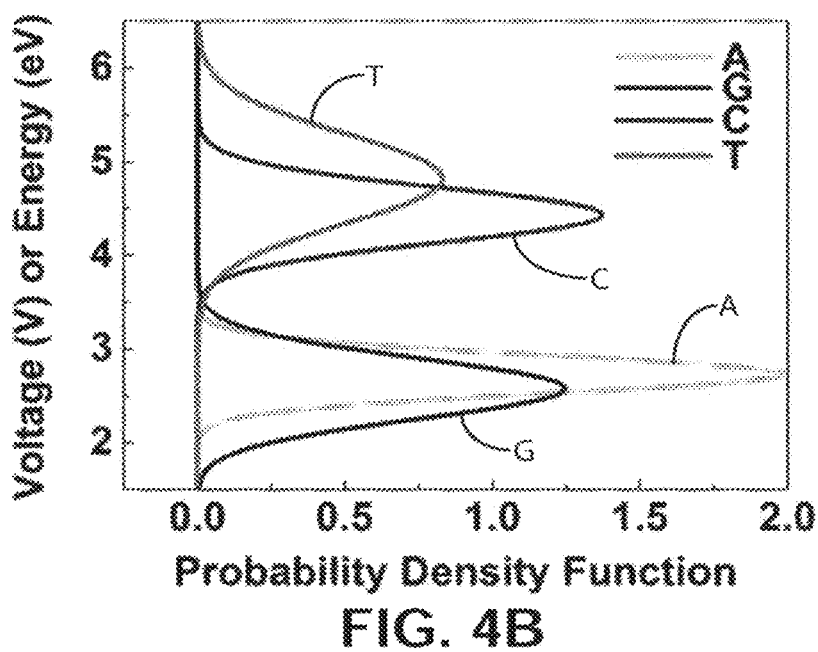

Tunneling current data may be analyzed in other ways in order to differentiate/distinguish various nucleobases. In some embodiments, tunneling current may be analyzed using a Fowler-Nordheim (F—N) plot. These plots may aid in identifying underlying biophysical parameters governing charge tunneling through the single nucleotides or through individual nucleotides of a polynucleotide. Tunneling current (I)-voltage (V) data may be plotted as $\ln(I/V^2)$ vs. $(1/V)$. In some embodiments, this plot may aid in extracting the transition voltage ($V_{trans}$) and the slope of the tunneling regime (for triangular barrier). $V_{trans}$ is determined as the minimum (equivalent to the transition point between different regimes) on the F—N plot. S is the slope of the F—N plot at high bias (small values of 1/V). This value takes a negative slope for electron tunneling and positive slope for hole tunneling. FIG. 4E is an example of a F—N plot for the nucleotide T. In some cases, the transition voltage, $V_{trans,e-}$, may represent the transition from tunneling to field emission regime, and the slope, S, may be a measure of tunneling barrier (for electrons here). In some cases, these biophysical parameters for electron ($V_{trans,e-}$) and hole ($V_{trans,h+}$) tunneling through the nucleotide sequences represent identifying components of electronic signatures, and may be used similarly to HOMO-LUMO and Band Gap values to characterize and identify unknown nucleotides and polynucleotide sequences.

In some cases, $V_{trans,e-}$ and $V_{trans,h+}$ values may be used to distinguish different nucleobases under different environmental conditions, for example pH. In some cases, $V_{trans,e-}$ and $V_{trans,h+}$ values, determined under acidic, neutral, and basic conditions may be used to differentiate among 2 or more nucleobases. In many embodiments, one or more parameters may be used to aid in differentiating 2 or more nucleobases. In some cases, the parameters may be selected from, $V_{trans,e-}$, $V_{trans,h+}$, S, HOMO, LUMO, or Band energy (Band Gap) values. In many embodiments, the parameters may be determined under one or more different conditions, for example acidic, neutral, or basic conditions.

In many cases, additional parameters may be extracted from analysis of tunneling data, such as transition voltage from tunneling to field emission, and the slope indicating the barrier for charge tunneling. These tunneling constants, $V_{trans,h+}$, $V_{trans,e-}$, $S = S_e + S_h$ (where $S_e = S$ electron tunneling and $S_h$ =hole tunneling), may be characteristic of the molecule through which charges are tunneled. In some cases, these parameters may be determined for individual nucleotides to aid in their differentiation. In some embodiments, these parameters may be combined with HOMO-LUMO and Band Gap values to aid in determining nucleobase identity and creating a nucleotide fingerprint. In some embodiments, determination of the change in hole tunneling probabilities using $V_{trans,h+}$, can be used like a HOMO level to determine the identity of nucleotides under different pH conditions.

Additionally, Fowler-Nordheim plots can be used to identify the tunneling transition voltage for both electron and hole ($V_{trans,e-}$ and $V_{trans,h+}$) and energy barrier (S) (FIG. 4E and Table III). Together, up to six parameters ($V_{HOMO}$, $V_{LUMO}$, Energy gap, S, $V_{trans,e-}$, $V_{trans,h+}$) can be used to identify and validate the identity of a single nucleotide.

TABLE III

Summary of values of $V_{trans}$ from FN plots for both electron ($V_{trans,\ e-}$) and hole ($V_{trans,\ h+}$) at different pH conditions on bare Au(111) surface. Values correspond to mean ± standard deviation.

| | Transition voltage, $V_{trans}$ (V) | HCl (acidic) | H$_2$O (neutral) | NaOH (basic) |
|---|---|---|---|---|
| A | $V_{trans,\ e-}$ | 1.11 ± 0.23 | 1.10 ± 0.19 | 1.23 ± 0.29 |
|   | $V_{trans,\ h+}$ | −0.58 ± 0.30 | −0.61 ± 0.25 | −0.56 ± 0.16 |
| C | $V_{trans,\ e-}$ | 1.55 ± 0.33 | 1.03 ± 0.18 | 0.98 ± 0.28 |
|   | $V_{trans,\ h+}$ | −0.58 ± 0.17 | −0.66 ± 0.25 | −0.67 ± 0.24 |
| G | $V_{trans,\ e-}$ | 1.10 ± 0.26 | 1.27 ± 0.12 | 0.91 ± 0.16 |
|   | $V_{trans,\ h+}$ | −0.57 ± 0.23 | −0.62 ± 0.22 | −0.72 ± 0.18 |
| T | $V_{trans,\ e-}$ | 1.52 ± 0.29 | 1.34 ± 0.14 | 1.12 ± 0.31 |
|   | $V_{trans,\ h+}$ | −0.91 ± 0.35 | −0.60 ± 0.17 | −0.68 ± 0.28 |

In many embodiments, an acidic environment may aid in the formation of distinguishable nucleotide isomers. The pKa for A, G, T, and C are about 4.1, 3.3, 9.9, and 4.4 respectively). In many cases, an acidic environment can be used to reproducibly sequence single nucleotides using Band Gap, HOMO, LUMO, $V_{trans}$ and S values (FIG. 4A, B, E, F). In some embodiments, a single STM-STS measurement, performed under acidic pH, may be used to sequence single stranded DNA (using STM) and single nucleotides (using STS data, shown for A in FIG. 5A and T, G, C, in FIG. 22). In other embodiments, multiple STM-STS measurements, performed under multiple pH environments, may be used to sequence single stranded DNA and single nucleotides. In some embodiments, the time scale for determining DNA and/or nucleotide identity with the disclosed method may be on the order of seconds or minutes.

In many embodiments, the disclosed technique may be able to sequence a polynucleotide with over about 85%, 90%, 95%, 96%, 97%, or 99% accuracy. In some embodiments, the presently claimed technique may be used to sequence polynucleotides of greater than about 30 nt, 40 nt, 50 nt, 60 nt, 70 nt, 80 nt, 90 nt, 100 nt, 200 nt, 300 nt, 400 nt, 500 nt, 1 k nt, 2 k nt, 3 k nt, 4 k nt, 5 k nt, or 10 k nt. In many cases, the disclosed technique can be used to determine 3'→5' order of a polynucleotide. In some cases, 3'→5' directionality may be determined by tagging the end of a single stranded DNA, in some embodiments the 3' or 5' end is tagged. For example, tagging may be accomplished by using a ligase with specific 5' or 3' end specific primer tags, for example T4 ligase. The ligation step may create templates with marked 5'- or 3'-ends. In some cases, the sequence near the tagged end may be known. Using the disclosed sequencing method, the known sequences will be identified by the tag, which will reveal the directionality of the unknown DNA sample.

The disclosed method may be used to differentiate and identify modified nucleobases. In some embodiments, the presently disclosed technique may be used to differentiate and identify nucleotides and nucleobases, including naturally occurring, synthetic, and/or modified nucleotides and nucleobases. Naturally occurring nucleotides may include modified and unmodified nucleobases, including adenine, guanine, cytosine, thymine, uracil, and inosine. In some embodiments, the disclosed method may be used to determine the identity of other A,U,G,C RNA bases containing ribose sugar with 2'OH group. Nucleobases may, in some cases be modified, for example by methylation. In some embodiments, various additional chemical modifications used with RNA, DNA, and/or sugar backbones can be detected. In some embodiments, the disclosed method may be used to detect 1-methyl-7-nitroisatoic anhydride, or benzoylcyanide, or other electrophiles), Dihydroxy-3-ethoxy-2-butanone (Kethoxal), CMCT (1-cyclohexyl-(2-morpholino-ethyl)carbodiimide metho-p-toluene sulfonate), or deaminated bases, for example deamination with bisulfite. Methylated nucleobases, may include methylcytosine, methyladenine, methylguanine, methyluridine, methylinosine, 5-methylcytosine, 5-hydroxymethylcytosine, 7-methylguanosine, N6-methyladenosine, and O6-methylguanine.

The disclosed compositions, methods, and techniques may be used to determine electronic signatures for a variety of molecules. In some case, the molecule may be a nucleotide or nucleobase. In many embodiments, the disclosed techniques and compositions may identify and differentiate molecules based on their electronic density of states. In some embodiments, the electronic density of states may be determined using tunneling spectroscopy (correlated STM-STS). In some embodiments, different electronic signatures may be identifiable and distinct for each molecule depending on the pH environment. In many cases, nucleotides may be analyzed in acidic, basic, and/or neutral conditions. In some embodiments, the acid-base behavior of nucleotides and their corresponding tautomeric structures may aid in identification of unknown nucleotides.

The presently disclosed technique may be automated to aid in the detection and sequencing of polymer chains, especially polynucleotides. In some embodiments, single chains may be sequenced using high resolution STS to provide for fast single-molecule sequencing with single nucleotide resolution. The disclosed technique can be developed for fast, inexpensive, accurate, enzyme-free, and high-throughput identification of single nucleotides and modifications, and can provide an alternative for next-generation sequencing technology in biomedical applications.

The presently claimed techniques, methods, devices, and compositions may be used to sequence a polynucleotide on a substrate. In some cases, the substrate is gold (111). In some embodiments, the substrate forms a microfluidic channel or a well. In some embodiments a microfluidic channel or well is coated with a ultrasmooth substrate, for example gold (Au (111)). In many embodiments, a plurality of polynucleotides may be sequenced simultaneously in separate channels or wells, using the disclosed technique. In many cases, a microfluidic well may feed a polynucleotide, for example a single stranded polynucleotide, into a microfluidic channel where the polynucleotide is sequenced using the disclosed technique.

Since a single STM tip and a single Au(111) substrate may be used for sequencing low concentrations of DNA or RNA, multiple microfluidic channels and wells and multiple STM tips can be used to extrude and sequence multiple polynucleotides (RNA or DNA molecules) simultaneously on the disclosed substrate. The operating costs for this fast, high-throughput, enzyme-free, single molecule DNA sequencing technique may be very low. For a simple gold substrate, entire genome sequences can be made on a single substrate, significantly reducing the cost of operation (to tens of dollars) and time (few hours or minutes) for entire sequence. In some embodiments, wherein many individual single polynucleotides are sequenced simultaneously, the time may be reduced to less than a few hours.

The present disclosure further provides for a method for identifying a nucleobase, nucleoside and/or a nucleotide comprising: acquiring tunneling current data for the a nucleobase, nucleoside and/or a nucleotide; deriving at least three, at least four, at least five, at least six, at least seven, at least eight or at least nine electronic signatures from the tunneling current data, wherein the electronic signatures are selected from the group consisting of a HOMO(eV) value, a LUMO (eV) value, a Bandgap(eV) value, a $Vtrans_+$ (V) value, a $Vtrans_-$ (V) value, a $\phi_{e-}$ (eV) value, a $\phi_{h+}$ (eV) value, a $m_{e-}/m_{h+}$ value and a $\Delta\phi$(eV) value; matching the at least three, at least four, at least five, at least six, at least seven, at least eight or at least nine electronic signatures to a set of corresponding electronic fingerprint reference values, thereby identifying the a nucleobase, nucleoside and/or a nucleotide; wherein, deoxyadenosine comprises the set of corresponding electronic fingerprint reference values of HOMO(eV) value is −1.39±0.3; LUMO(eV) value is 1.42±0.24; Bandgap(eV) value is 2.81±0.41; $Vtrans_+$ (V) value is 1.14±0.2; $Vtrans_-$ (V) value is −0.51±0.32; $\phi_{e-}$ (eV) value is 1.45±0.57; $\phi_{h+}$ (eV) value is 1.03±0.61; $m_{e-}/m_{h+}$ value is 0.29±0.23 and $\Delta\phi$(eV) value is 2.48±0.98; adenosine comprises the set of corresponding electronic fingerprint reference values of HOMO(eV) value is −1.44±0.2; LUMO (eV) value is 1.47±0.21; Bandgap(eV) value is 2.9±0.27; $Vtrans_+$ (V) value is 1.26±0.26; $Vtrans_-$ (V) value is −0.63±0.23; $\phi_{e-}$ (eV) value is 2.06±0.72; $\phi_{h+}$ (eV) value is 1.25±0.59; $m_{e-}/m_{h+}$ value is 0.43±0.17 and $\Delta\phi$(eV) value is 3.3±0.93; methylated deoxyadenosine comprises the set of corresponding electronic fingerprint reference values of HOMO(eV) value is −2.04±0.28; LUMO(eV) value is 2.06±0.37; Bandgap(eV) value is 4.1±0.25; $Vtrans_+$ (V) value is 1.47±0.37; $Vtrans_-$ (V) value is −0.91±0.27; $\phi_{e-}$ (eV) value is 1.6±0.36; $\phi_{h+}$ (eV) value is 1.28±0.41; $m_{e-}/m_{h+}$ value is 1.21±0.98 and $\Delta\phi$(eV) value is 2.87±0.74; deoxyguanosine comprises the set of corresponding electronic fingerprint reference values of HOMO(eV) value is −1.36±0.19; the LUMO(eV) value is 1.48±0.24; the Bandgap(eV) value is 2.84±0.27; the $Vtrans_+$ (V) value is 1.13±0.13; the $Vtrans_-$ (V) value is −0.48±0.29; the $\phi_{e-}$ (eV) value is 1.33±0.3; the $\phi_{h+}$ (eV) value is 0.79±0.5; the $m_{e-}/m_{h+}$ value is 0.32±0.25 and the $\Delta\phi$(eV) value is 2.12±0.65; guanosine comprises the set of corresponding electronic fingerprint reference values of HOMO(eV) value is −1.4±0.31; the LUMO(eV) value is 1.47±0.19; the Bandgap (eV) value is 2.86±0.31; the $Vtrans_+$ (V) value is 1.13±0.17; the $Vtrans_-$ (V) value is −0.59±0.15; the $\phi_{e-}$ (eV) value is 1.97±0.44; the $\phi_{h+}$ (eV) value is 1.07±0.44; the $m_{e-}/m_{h+}$ value is 0.54±0.19 and the $\Delta\phi$(eV) value is 3.04±0.72; methylated deoxyguanosine comprises the set of corresponding electronic fingerprint reference values of HOMO (eV) value is −2.24±0.42; the LUMO(eV) value is 2.3±0.64; the Bandgap(eV) value is 4.53±0.85; the $Vtrans_+$ (V) value is 1.5±0.46; the $Vtrans_-$ (V) value is −1.33±0.55; the $\phi_{e-}$ (eV) value is 3.29±1.36; the $\phi_{h+}$ (eV) value is 3.25±1.69; the $m_{e-}/m_{h+}$ value is 1.13±0.72 and the $\Delta\phi$(eV) value is 6.54±2.98; deoxycytidine comprises the set of corresponding electronic fingerprint reference values of HOMO(eV) value is −1.81±0.34; the LUMO(eV) value is 2.39±0.4; the Bandgap(eV) value is 4.2±0.49; the $Vtrans_+$ (V) value is 1.34±0.31; the $Vtrans_-$ (V) value is −0.8±0.26; the $\phi_{e-}$ (eV) value is 2.62±0.89; the $\phi_{h+}$ (eV) value is 1.57±0.63; the $m_{e-}/m_{h+}$ value is 0.64±0.31 and the $\Delta\phi$(eV) value is 4.19±1.17; cytidine comprises the set of corresponding electronic fingerprint reference values of HOMO(eV) value is −1.4±0.24; the LUMO(eV) value is 2.2±0.22; the Bandgap(eV) value is 3.6±0.25; the $Vtrans_+$ (V) value is 1.59±0.28; the $Vtrans_-$ (V) value is −0.59±0.33; the $\phi_{e-}$ (eV) value is 3.17±0.63; the $\phi_{h+}$ (eV) value is 1.23±0.68; the $m_{e-}/m_{h+}$ value is 0.39±0.25 and the $\Delta\phi$(eV) value is 4.4±1; methylated doexycytidine comprises the set of corresponding electronic fingerprint reference values of HOMO(eV) value is −2.78±0.39; the LUMO(eV) value is 2.62±0.59; the Bandgap(eV) value is 5.4±0.36; the $Vtrans_+$ (V) value is 1.62±0.37; the $Vtrans_-$ (V) value is −1.89±0.29; the $\phi_{e-}$ (eV) value is 3.07±0.8; the $\phi_{h+}$ (eV) value is 3.4±1.13; the $m_{e-}/m_{h+}$ value is 1.18±1.46 and the $\Delta\phi$(eV) value is 6.46±1.89; thymidine comprises the set of corresponding electronic fingerprint reference values of HOMO(eV) value is −1.38±0.19; the LUMO(eV) value is 2.68±0.3; the Bandgap(eV) value is 4.06±0.32; the $Vtrans_+$ (V) value is 1.43±0.37; the $Vtrans_-$ (V) value is −0.44±0.19; the $\phi_{e-}$ (eV) value is 2.75±0.69; the $\phi_{h+}$ (eV) value is 0.85±0.4; the $m_{e-}/m_{h+}$ value is 0.33±0.17 and the $\Delta\phi$(eV) value is 3.61±0.73; and uracil comprises the set of corresponding electronic fingerprint reference values of HOMO(eV) value is −1.51±0.25; the LUMO(eV) value is 2.04±0.25; the Bandgap(eV) value is 3.54±0.31; the $Vtrans_+$ (V) value is 1.53±0.34; the $Vtrans_-$ (V) value is −0.9±0.36; the $\phi_{e-}$ (eV) value is 3.71±1.36; the $\phi_{h+}$ (eV) value is 1.98±1.09; the $m_{e-}/m_{h+}$ value is 0.68±0.29 and the $\Delta\phi$(eV) value is 5.68±1.61.

The present disclosure further provides for a method for developing a set of electronic fingerprint reference values for nucleobase, nucleoside and/or a nucleotide comprising: acquiring tunneling current data for the nucleoside, wherein the identity of the nucleobase, nucleoside and/or a nucleotide is known; deriving at least one, at least two, at least three, at least four, at least five, at least six, at least seven, at least eight or at least nine electronic signatures from the tunneling current data; developing the set of electronic fingerprint reference values from the electronic signatures, wherein the set of electronic fingerprint reference values are capable of identifying the nucleobase, nucleoside and/or a nucleotide.

In another aspect, the set of electronic fingerprint reference values are capable of distinguishing a first nucleobase, nucleoside and/or a nucleotide from a second nucleobase, nucleoside and/or a nucleotide, wherein the first nucleobase, nucleoside and/or a nucleotide and the second nucleobase, nucleoside and/or a nucleotide are different nucleosides.

In another aspect, the electronic signatures are selected from the group consisting of a HOMO(eV) value, a LUMO (eV) value, a Bandgap(eV) value, a $Vtrans_+$ (V) value, a $Vtrans_-$ (V) value, a $\phi_{e-}$ (eV) value, a $\phi_{h+}$ (eV) value, a $m_{e-}/m_{h+}$ value and a $\Delta\phi$(eV) value.

In another aspect, the set of electronic fingerprint reference values are selected from the group consisting of a HOMO(eV) value, a LUMO(eV) value, a Bandgap(eV) value, a $Vtrans_+$ (V) value, a $Vtrans_-$ (V) value, $\phi_{e-}$ (eV) value, a $\phi_{h+}$ (eV) value, a $m_{e-}/m_{h+}$ value and a $\Delta\phi$(eV) value.

The present disclosure further provides for method for determining a nucleic acid sequence, wherein the nucleic acid sequence is selected from the group consisting of DNA, modified DNA, RNA, modified RNA, PNA, modified PNA and any combination thereof, and wherein the nucleic acid sequence comprises nucleobases and a charged backbone.

Massively Parallel Sequencing

In some embodiments, massively parallel sequencing using QM-Seq is provided. In some such embodiments, the disclosed technique may be used to provide massively parallel sequencing using a stripped gold substrate. In one embodiment, template stripping may be used to prepare the substrate, and the massively parallel STM imaging may be performed using template stripped gold substrates. In one embodiment, the tips may be created optically, using optical lithography, followed by anisotropic etching, such as KOH etching.

Figure 27B:
FIGS. 27A-C: (a) is a picture of centimeter scale optically created tip patterns, using a simple optical lithography, followed by anisotropic KOH etching. (b) is a SEM image showing high fidelity and periodically patterned STM tips made from gold. Using a large area (cm×cm) scale STM chip on an ultraflat/ultrasmooth substrate, a 2 μm×2 μm surface can be scanned, and create an entire sequence over cm scale, by massively parallel scanning and simple readout from a chip, similar to the ones shown in the figure. (c) is a 1 megapixel (or one megatip) 2 cm×2 cm chip. Voltage can be simultaneously applied to a plurality of tips, the current is collected and stored, and all current values from the plurality of tips may be read simultaneously (similar to a CCD camera). After the current is read, another bias voltage can be applied, and so on, to recreate the entire current-voltage curve over a massive 2 cm×2 cm substrate. Several thousand genomes can be placed, linearized and read simultaneously in the microfluidic channels. Piezos may be used to move a sample a few angstroms, to allow for sequencing the next nucleobases—and the process repeated to analyze additional nucleobases. Therefore, in a single 2 micrometer scan movement (or piezo scan), of the massively parallel sequencer can sequence all possible nucleobases on a relatively large sample biochip, patterned using a simple microfluidic device.
Figure 40A:
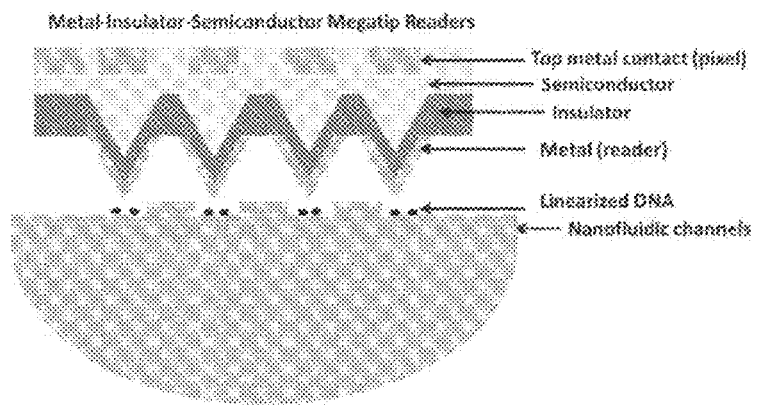
FIG. 40A-B: Schematic showing (A) metal-insulator-semiconductor (MIS) multi-tip readers, and (B) metal-insulator-metal (MIM) readers. Following application of a single voltage, parallel reads are performed by all sharp metal tips, the charge stored in MIS or MIM pixels, and sequentially transferred to the "read" line (using microprocessors and signal timers), amplified using a current amplifier, converted to a digital signal (analog-to-digital converter), and then stored. Then the voltage is scanned (second voltage applied), and read, to construct the I-V curves for all multi-tips. This data is sent to the base calling algorithm for determining the sequence for all DNA, RNA, modifications etc. using the QM-Seq parameters library.
Figure 40B:
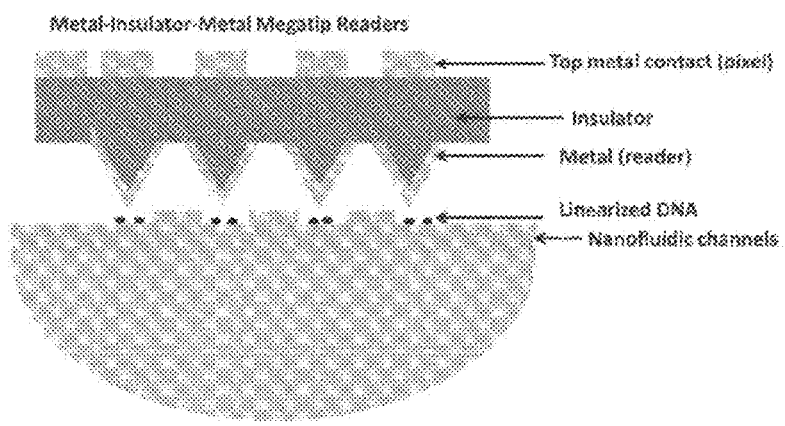

Massively parallel sequencing uses an array of tips, e.g., as shown FIG. 27. In some embodiments, each tip may comprise a metal-insulator-semiconductor (MIS) structure, which in some instances is similar to a charge-couple device (CCD) structure. In an MIS tip structure, a metal contact is coated with an insulator, which is coated with insulator semiconductor, and finally a metal, which forms the outer surface of the tip. See FIG. 40A. In some embodiments, each tip may comprise a metal-insulator-metal (MIM) structure, which comprises a metal contact coated with an insulator and then with a metal that forms the outer surface of the tip. See FIG. 40B.

In some embodiments, the tips form a regular array in which each set of two tips is separated by 50 nm (tip point to tip point). In some embodiments, the tips form rows in which each set of two tips in the row are separate by a first distance, and the two adjacent tips in two adjacent rows are separated by a second distance. In some embodiments, the first distance and the second distance are the same. In some embodiments, the first distance and the second distance are each between 10 nm and 100 µm (but they may be the same or different). In some embodiments, the first distance and the second distance are each between 10 nm and 10 µm, or between 10 nm and 1 µm, or between 10 nm and 100 nm. In some embodiments, the first distance and the second distance are each between 10 nm and 100 nm, or are each between 20 nm and 80 nm. The tips are, in some embodiments, arrayed on a single flat surface to form a chip (also referred to as a "multi-tip" or "multi-tip reader" or "multi-tip array").

Nonlimiting exemplary multi-tips comprise arrays of at least 100, at least 500, at least 1,000, at least 2,000, at least 5,000, at least 10,000, at least 50,000, at least 100,000, at least 200,000, at least 500,000, or at least 1,000,000 tips. In some embodiments, a multi-tip comprises an array of between 100 and 5,000 tips in a first dimension by between 100 and 5,000 tips in a second dimension, or between 500 and 2,000 tips in a first dimension and between 500 and 2,000 tips in a second dimension. In some embodiments, a multi-tip comprises an array of 1,000×1,000 tips. In some embodiments, a multi-tip comprises an array that is other than 1,000×1,000 tips. In some embodiments, the tips are arrayed such that the ratio of the longest side of the chip to the shortest side of the chip is between 1 and 2 or between 1 and 1.5. In some embodiments, the tips are arrayed such that the ratio of the longest side of the chip to the shortest side of the chip is about 1.

In some embodiments, massively parallel sequencing uses an ultrasmooth surface (such as Au(111)) surface modified with a polycationic polymer, such as poly-lysine, or with a positively charged polyelectrolyte. In some embodiments, nucleic acid (such as ssDNA, RNA, modified oligonucleotide, aptamer, etc.) is fluidically spread onto the ultrasmooth surface modified with a polycationic polymer or positively charged polyelectrolyte (referred to in some instances as the "substrate") at a desired density. Nonlimiting exemplary densities for nucleic acid on the ultrasmooth surface include. For example, in some embodiments, nucleic acid is deposited at a density of between 0.1 and 1000 nucleic acid molecules per channel, or between 0.1 and 100 nucleic acid molecules per channel, or between 1 and 100 nucleic acids per channel, or between 0.1 and 10 nucleic acids per channel.

Figure 38A:
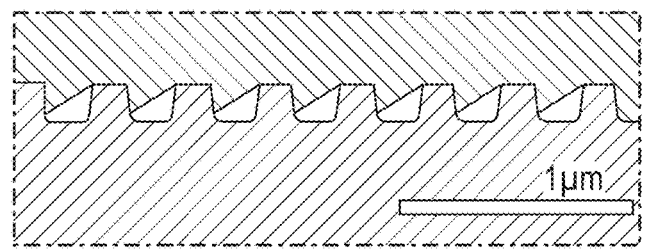
FIGS. 38A-B: (A) SEM image showing nanofluidic channels for automated multiplexed QM-Seq with increased duty-cycle (or fraction of scanned areas with DNA sample). (B) Atomic force micrograph (AFM) image for the nanofluidic channel and the line scan showing the periodicity and the depth of the channel.
Figure 38B:
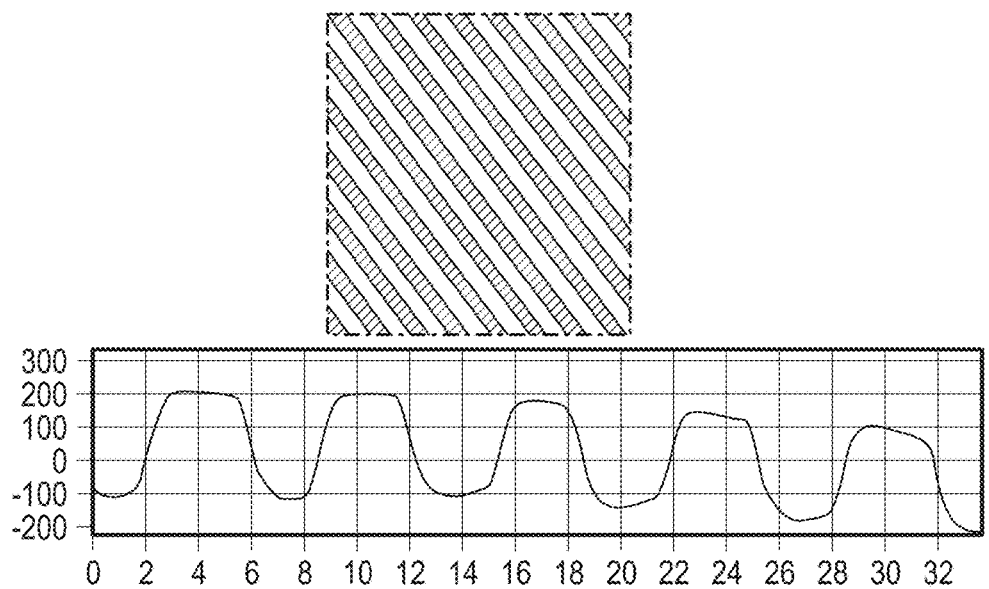

In some embodiments, the ultrasmooth surface comprises non-wetting hydrophobic polymer "ridges" that form channels of exposed polycationic polymer- or positively charged polyelectrolyte-coated ultrasmooth surface (such as polylysine-coated Au(111)). A nonlimiting exemplary surface with polymer ridges is shown in FIG. 38. In some embodiments, the channels may be created using nanolithography, which is described, for example, in Nagpal et al., 2009, Science 325: 594. Nonlimiting exemplary non-wetting hydrophobic polymer that may be used to form the ridges include polystyrene, polymethylsiloxane, polymethylmethacrylate, and the like. The channels, in various embodiments, may be between 10 nm and 10 µm apart, from center to center, or between 10 nm and 1 µm apart, or between 10 nm and 100 nm apart, or between 20 nm and 80 nm apart. The distance between the center of two adjacent channels is typically about the same as the distance between two adjacent rows of tips (measured tip to tip), allowing adjacent tips to be placed in the center of adjacent channels simultaneously. In some embodiments, the substrate comprises at least 10, at least 100, at least 200, at least 300, at least 500, at least 800, or at least 1000 channels. In some embodiments, the substrate comprises at least as many channels as the multi-tip reader comprises tips in one of its dimensions (that is, if the multi-tip reader comprises 1,000×1,000 tips, the substrate comprises at least 1,000 channels).

In some embodiments, the polymer surface is sloped towards the exposed polycationic polymer- or positively charged polyelectrolyte-coated ultrasmooth surface to reduce the amount of surface that is coated with nucleic acid, thereby increasing the duty cycle of the scan. Thus, in some embodiments, the width of the polymer ridge at its top is less than the width of the polymer ridge at its bottom, where it contacts the ultrasmooth surface. In this manner, the pointed tips can "fit" into the channels, which have a larger width at the top (where the tip is wider) and a smaller width at the bottom (where the tip reaches a point), and the duty cycle is increased because the surface area at the bottom of the channel is narrower than it would be if the ridges were perpendicular. In some embodiments, the multi-tip is raised while the nucleic acid is deposited on the surface, and then lowered for scanning. In some embodiments, the tip in its lowered position for scanning is 0.1 to 5 nm above the surface on which the nucleic acid is deposited. In some embodiments, the variation in tip height on the multi-tip is less than 5 nm, or less than 1 nm.

As a nonlimiting example of scanning using a multi-tip, each tip may scan a 10 nm section of a defined width (e.g., 10 nm to 10 µm or 10 nm to 100 nm) at 2 Å resolution with 50 lateral scans. In embodiments comprising channels, if that portion of the channel has 1 nucleic acid molecule bound to the surface, then the duty-cycle for the scan is about 6-8% (for example, a nucleobase is about 0.6-0.8 nm, which makes up 6-8% in a 10 nm channel). If that portion of the channel has 2 nucleic acid molecules bound to the surface, then the duty-cycle for the scan is about 12-16%. The density of the nucleic acid in the channels can be varied by changing the polymer profile and/or concentration of nucleic acid in the solution that is flowed through the channel during nucleic acid deposition. A similar calculation and considerations apply to embodiments comprising nucleic acid deposited on the ultrasmooth surface without channels.

EXAMPLES

Example 1—LUMO, HOMO, and Band Gap Values

Flame annealed flat, template-stripped ultrasmooth gold (111) substrates (see below). To prepare linearized DNA with nucleotides drawn out from the substrate (to study charge tunneling through the nucleobases, instead of the sugar backbone), a positively charged gold (111) surface was prepared and developed for use in a new extrusion deposition technique, detailed below (FIG. 1A).

STM Substrate Preparation

The flame-annealed Au(111) surface was obtained by template stripping. In a typical template stripping process, thermally evaporated gold (Au) films are flame annealed on silicon (100), or other index matched substrate (Au(111) is formed at 45° orientation to Si(100)), to produce Au(111) orientation. Since the gold coating has no adhesion to the cleaned silicon substrate, they can be peeled off by using an epoxy, electrodeposited metal, or other polymer films which can adhere to the gold. The peeled off films reveal atomically flat (mimicking the smoothness of flat silicon wafer) Au(111) substrate (described in Nagpal et al., *Science*. 325, 594, 2009). Immediately after peeling, the surface was treated with $O_3$ plasma for 2 min (Jelight Company INC UVO Cleaner Model No. 42), to negatively charge the surface uniformly (for adsorption of positively charged polyelectrolyte). For bare gold samples, first 500 µL of 0.1M HCl, 0.1M $Na_2SO_4$ or 0.1M NaOH was added on the surface and dried with compressed air. Then 1 µL of DNA solution (either oligomers or ampR) was extended with translational motion on the surface and let it dry. For poly-l-lysine samples, 25 µL of 10 ppm solution (MW 70,000-150.00 g/mol purchased from Sigma, USA) was added on clean gold substrate followed by 5 min incubation at room temperature, then it was washed with 500 µL of double distilled $H_2O$ and dried with compressed air. The DNA sample was prepared for STM-STS, as described above. Additionally, the samples were washed with 500 µL of water, acid or base at same concentration and dried under compressed air.

ssDNA Oligomers and ssDNA ampR DNA for STM

Single-stranded oligomers, (poly(dA)$_{15}$, poly(dC)$_{15}$, poly (dG)$_{15}$, poly(dT)$_{15}$) were purchased from Invitrogen, USA. The DNA oligomers were dissolved in 0.1M $Na_2SO_4$ solution at a concentration of 20 µM and stored at −20° C. until used. DNA concentrations were measured using NanoDrop 2000 spectrophotometer (Thermo Scientific, USA).

Extrusion Deposition Technique for Linearizing DNA Strands for Sequencing

Figure 23B:
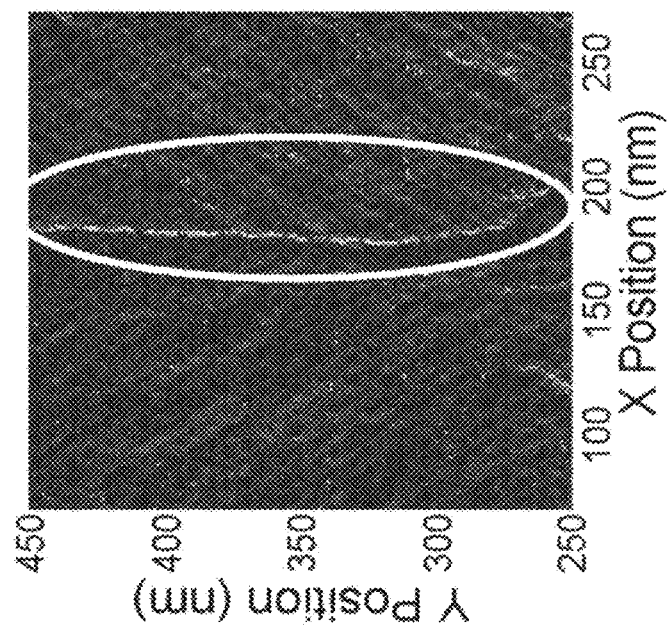
FIGS. 23A-B: Linearization of ssDNA using the extrusion deposition technique. STM images of ssDNA deposited on bare gold without extrusion (a) and on poly-L-lysine modified gold with extrusion (b). The role of poly-L-lysine coating and our extrusion deposition scheme is clearly visible in this STM data, where linearized DNA allows clear STS identification of single nucleotides (FIG. 25).
Figure 23A:
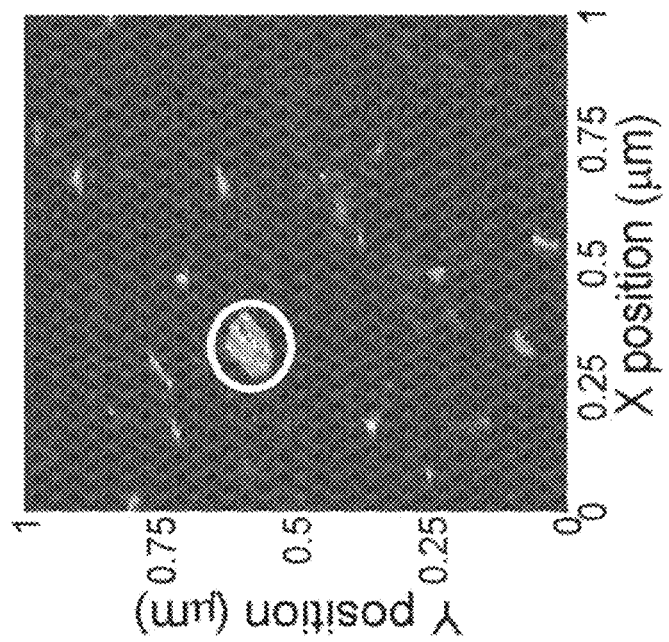

To disperse elongated linear ssDNA on gold substrate, a three-step procedure was followed. First, the gold (111) surface was positively charged by coating it with by 10 ppm poly-L-lysine solution as described above. Second, ssDNA was melted at 95° C. for 5 min, followed by flash cooling on ice for 5 min. In some cases, dsDNA and short mononucleotide ssDNA strands do not contain tertiary structures, but 1 kb long ssDNA can form secondary structures. In general, melting may help remove secondary structures on DNA and the use of a positively charged surface may help disrupting secondary structures. Positive charge on the surface was provided by poly-L-lysine peptide which links with the phosphate backbone via electrostatic interaction. In most cases, for example for sequencing purposes, acidic conditions were used to de-convolute/distinguish/differentiate four nucleotides, C, T and purines—G or A. Third, the ssDNA dispersion (1-5 nM) was extruded on the modified Au(111) surface with a translational motion, to form linearized DNA chains (FIG. 23, described below). Extrusion of the polynucleotide was done with different setups. As specific examples, we describe two embodiments: using a pipette tip (0.1-1 L) and slowly applying a translational motion while depositing; and using microfluidics, where the polynucleotide is added on one side and the capillary forces extrudes the polynucleotide through the nano/micro-channel.

Depositing DNA on a positively charged gold surface, following an extruding motion, allowed the DNA to be immobilized on the gold surface due to interactions of the negatively charged phosphate backbone with positively charged surface. This interaction exposed the nucleotides on top of atomically flat gold, and allowed the nucleotides to to be sequenced using measurement of their STS spectrum. This method also reduced secondary structures, by linearizing the ssDNA, as well as reduces the noise and background signals from the ribose sugar and the phosphate backbone.

Surface modification with poly-L-lysine produced only small changes in the LUMO-HOMO levels of the nucleobases. This effect may be due to the slight basic component of lysine residues which increases the surface relative pH.

Figure 3A:
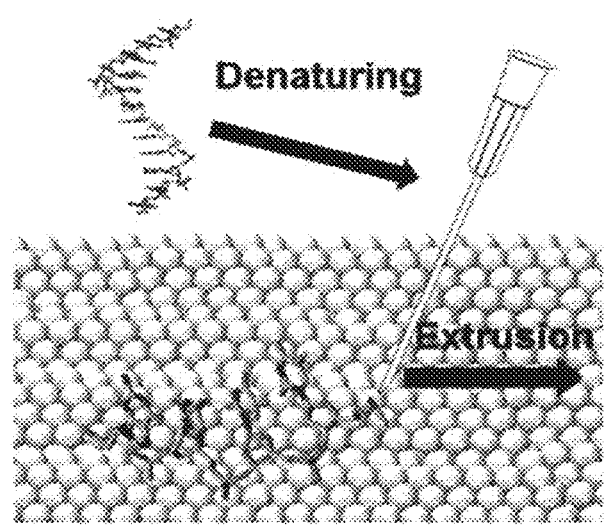
FIGS. 3A-F: Sequencing single DNA molecule using scanning tunneling microscopy—scanning tunneling spectroscopy (STM-STS). (a) Illustration showing the DNA processing scheme. Denatured single stranded (ss) DNA are deposited on clean Au (111) surface modified with poly-L-lysine using an extrusion deposition technique to reproducibly obtain elongated linearized DNA template for sequencing. (b) Schematic illustration of STM-STS to obtain topographic image, I—V and dI/dV or Density of states (DOS) spectra of ssDNA nucleotides, deposited on positively charged Au (111) surface. Electron or holes tunnel through single nucleotides to provide the tunneling probability using electrical tunneling current data. A, G, C, T nucleotides are, where possible, differentiated by different shading. (c-f) Chemical structure of DNA nucleotides (monophosphates), Adenosine 5'-monophosphate (c), Deoxyguanosine 5'-monophosphate (d), Deoxycytidine 5'-monophosphate (e), and Deoxythymidine 5'-monophosphate (f), at neutral pH.

A chemically-etched platinum-iridium tip (80:20 Pt—Ir) was used and correlated STM and STS studies were conducted, by tunneling electrons and holes through the linearized DNA nucleotides (FIGS. 1a and 3a,b). The tunneling current spectroscopy data (current (I)-voltage (V)) is a direct measure of the local electronic density of states (dI/dV spectra, FIG. 10 and discussion above) of the molecule, and serves to help create a unique electronic fingerprint based on the nucleotides biochemical structure (FIGS. 1 and 3a,b). To identify distinct tunneling signatures for the various DNA nucleotides, the electron/hole tunneling through the nucleotides, was investigated under different pH conditions. The presence of keto-enol tautomers of the nucleobases under different pH conditions (FIG. 11 and described below) can aid in separating electron/hole tunneling probability between purines (A,G) and pyrimidines (C,T) to aid in differentiating these two groups.

Imaging and Spectroscopy

Scanning Tunneling Microscope images were obtained with a modified Molecular Imaging PicoSPM II using chemically etched Pt—Ir tips (80:20) purchased from Agilent Technologies, USA. The instrument was operated at room temperature and under atmospheric pressure. Tunneling junction parameters were set at tunneling currents of 100 pA and sample bias voltage of 0.1V. Spectroscopy measurements were obtained at a scan rate of 90V/s with previous junction parameters in order to avoid degradation of the DNA sample due to high current/voltage. Scanning tunneling spectroscopy data containing information on current-voltage (I-V) spectra was used to obtain its derivative dI/dV using Matlab. dI/dV is proportional to the electronic local density of states as discussed below. Energy band assignment of LUMO and HOMO levels was done by assigning the first significant positive and negative peaks on the spectra, respectively (FIG. 10). The energy difference between LUMO and HOMO values defines the electronic LUMO-HOMO energy band gap. Each nucleotide was assigned based on its HOMO/LUMO and energy gap for primary identification between purines and pyrimidines. Identification of C and T was based on their LUMO and HOMO level differences.

Figure 2A:
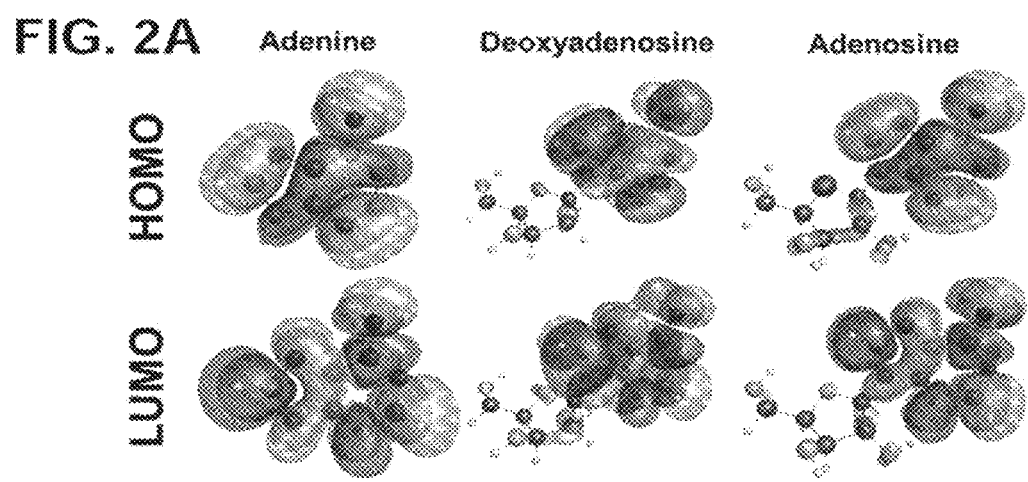
FIGS. 2A-B: Frontier Molecular Orbitals of nucleobases, deoxynucleosides and ribonucleosides: HOMO, LUMO molecular orbitals structures using density functional theoretical (DFT) calculations with B3LYP functional and 6-311G (2d,2p) basis set for (a) adenine, deoxyadenosine and adenosine as a purine example; and for (b) cytosine, deoxycytidine and cytidine as example of pyrimidine. Shading indicates the different phases of the wave function.
Figure 2B:
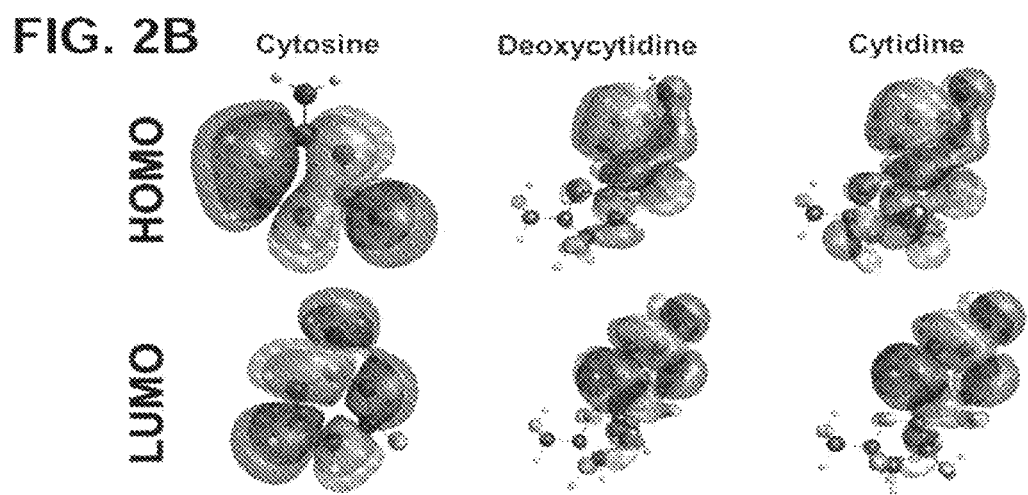

X-Y positions corresponding to each pixel were used to calculate the distances between data points. This information was also used to assign sequence, as each nucleotide has a size of about 0.65 nm. Based on spatial measurements of nucleotide sequences, the distance between two adjacent measurements was computed in nm and divided by 0.65. Therefore, each measurement corresponds to a contiguous nucleotide and the position is only used for computing the order thereof. The sequences were therefore identified using the Quantum Molecular Sequencing scans First, for each nucleotide biophysical parameters were identified, for example, HOMO, LUMO, Band Gap, Transition voltage (positive and negative), ratio of electron/hole effective masses, $\varphi_0$ for electron and hole and $\Delta\varphi_0$. Identified parameters from reference library (as determined on training sets from well-characterized, known sequences, such as homopolynucleotides lacking modifications) were used to construct a machine learning model as a reference. Then, unknown spectra were processed to extract the parameters and those were compared against the training set to identify the probability of each individual group from the training set. The group with highest probability is assigned to the original spectra and used for sequence alignment. This methodology allows identification of the sequence. For checking the accuracy of the identified sequencing against annotated sequences (e.g. ampR here),the identified sequence was compared against ampR sequence available at National Center for Biotechnology information (Accession number EF680734.1, available at www.ncbi.nlm.nih.gov/nuccore/EF680734.1), using Basic Local Alignment Search Tool (BLAST). BLAST is used in this case for aligning the measured sequence to a reference. In addition to sequence aligning, the data obtained can also be used for de novo assembly into a new sequence annotation Density Functional Theory Simulations:

Electronic structure calculations were performed using density functional theory with B3LYP functional and 6-311G(2d,2p) basis set on GAMESS software package using restricted Hartree-Fock method and depicted in FIG. 2, and described in *Phys. Rev.* 140, A1133, C. C. J. Roothaan *Rev. Mod. Phys.* 23, 69-89, and *J. Comput. Chem.* 14, 1347-1363 (1993). For neutral nucleobases comparison with deoxynucleotides and ribonucleotides a 6-311G(2d,2p) basis set, as described at *J. Chem. Phys.* 77, 3654 (1982) and *J. Chem. Phys.* 80, 3265 (1984), was used which provides accurate results as it is a split-valence triple zeta description of the Gaussian orbitals. The study case of the different tautomers with pH on the isolated nucleobases we used a 6-31++G(2d,2p) basis set as described at *J. Chem. Phys.* 77, 3654 (1982) and *J. Chem. Phys.* 80, 3265 (1984). Addition of diffuse functions on both hydrogens and heavy atoms provides a better description for charged molecules. The structure of each nucleobase, nucleotide, or nucleoside was initially optimized using Jmol software integrated feature. Further geometry optimization was calculated during electronic calculation on GAMESS. Molecular orbitals were drawn using MacMolPlt.

TABLE IV

Summary of isolated nucleobases energy band gaps simulated from density function theoretical DFT calculations using 6-31++G(2d, 2p) basis set and B3LYP functional.

| | Band Gap (eV) | | |
|---|---|---|---|
| Nucleobase | HCl (acidic) | H$_2$O (neutral) | NaOH (basic) |
| A | 4.68 | 5.33 | — |
| C | 5.71 | 5.27 | — |
| G | 4.71 | 5.17 | 3.48 |
| T | 5.55 | 5.41 | 4.16 |
| U | 5.71 | 5.61 | 4.22 |

TABLE V

Comparison of energy band gaps from nucleobases, deoxyribonucleotides and ribonucleotides calculated with DFT using 6-311G(2d, 2p) basis set and B3LYP functional in neutral conditions. Energy band gaps in eV.

| | Nucleobase | Deoxynucleotide | Nucleotide |
|---|---|---|---|
| A | 5.43 | 5.42 | 5.39 |
| C | 5.39 | 5.36 | 5.39 |
| G | 5.51 | 5.42 | 5.44 |
| T | 5.52 | 5.39 | — |
| U | 5.69 | — | 5.50 |

STS measurements performed at acidic pH may facilitate formation of keto/enol isomers. Acid pH environments may be achieved by addition of a strong acid, for example HCl In many embodiments, the pH environment may be achieved by addition of any acid, base, or pH buffers, for example acids may include sulfuric, citric, nitric, lactic, carbonic, phosphoric, boric, oxalic, and acetic acid. In most embodiments, the acid used to change the pH environment. In many embodiments, the acid will have a pKa below 3, which may aid in ensuring that the desired nucleotide chemical modification can be achieved. In the case of deoxyribonucleotides, this may be seen in FIG. 11. In many cases, STS performed at acidic pH may allow for separation of Lowest Unoccupied Molecular Orbital (LUMO) and Highest Occupied Molecular Orbital (HOMO) levels, which may indicate the probability of tunneling electron and holes, respectively. This separation may be seen in the V or eV vs Probability plots of FIG. 4A. This separation may also be seen in the energy "Band Gap", or the difference between HOMO-LUMO levels depicted in FIG. 4B. In some embodiments, HOMO levels (or hole tunneling probability) of nucleotides C ($-1.30\pm0.17$ eV) and T ($-1.74\pm0.29$ eV) may also exhibit a separation as seen in FIG. 4A. The separation between C and T HOMO levels may be due to their keto and enolized structures (FIG. 11).

Basic conditions may also be used to distinguish nucleobases. In some cases, basic pH may aid in distinguishing between Adenine and Guanine nucleotides (A and G). In these cases, LUMO levels may be about $1.72\pm0.19$ eV for A and $1.33\pm0.17$ eV for G. In some embodiments, basic pH may be achieved by addition of a strong base, for example NaOH. In many cases, the desired pH environment may be achieved by addition of a variety of acids, bases or buffers, including potassium, ammonium, calcium, magnesium, barium, aluminum, ferric, and zinc lithium hydroxide). In most cases, a base used to achieve a basic pH will have a pKa above 9, which may aid in ensuring that the desired nucleotide chemical modification can be achieved In some case, HOMO levels for A and G may also differ under basic conditions. Values for four nucleotides, A, T, G, and C, in three different environments, are reported in Table I.

Figure 4C:
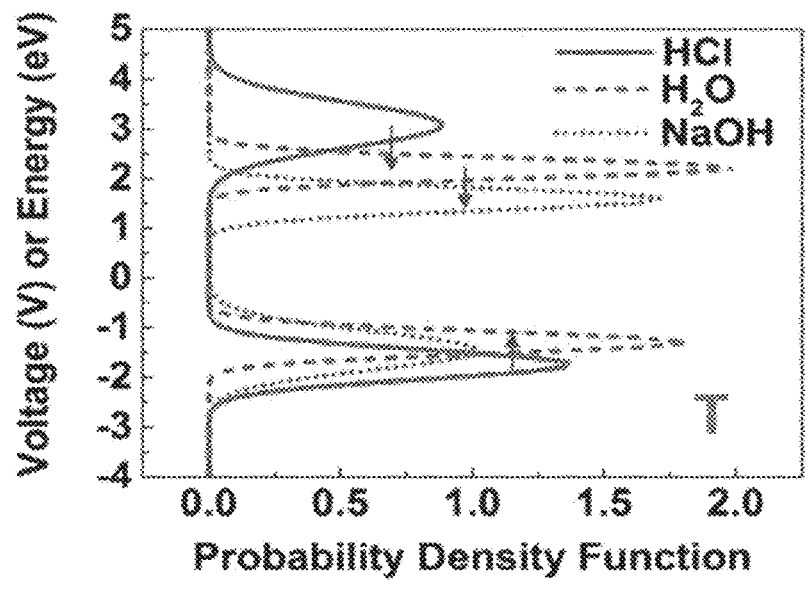
Figure 4D:
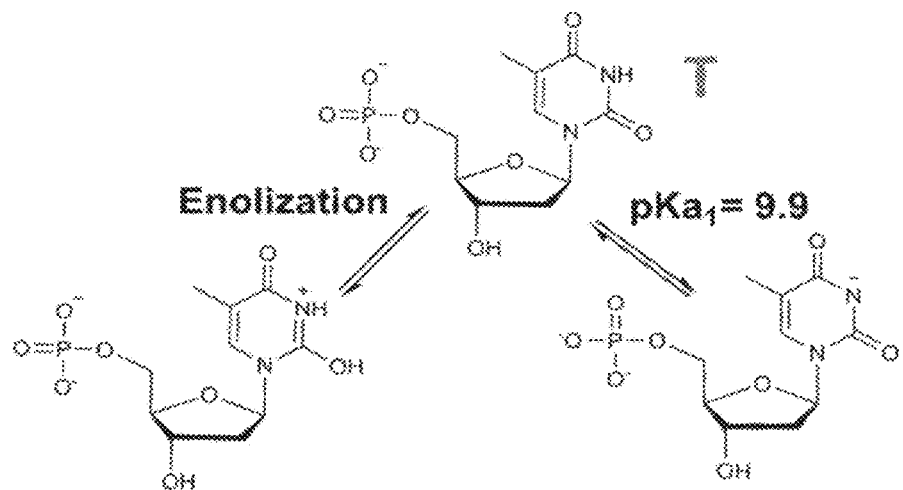
Figure 4E:
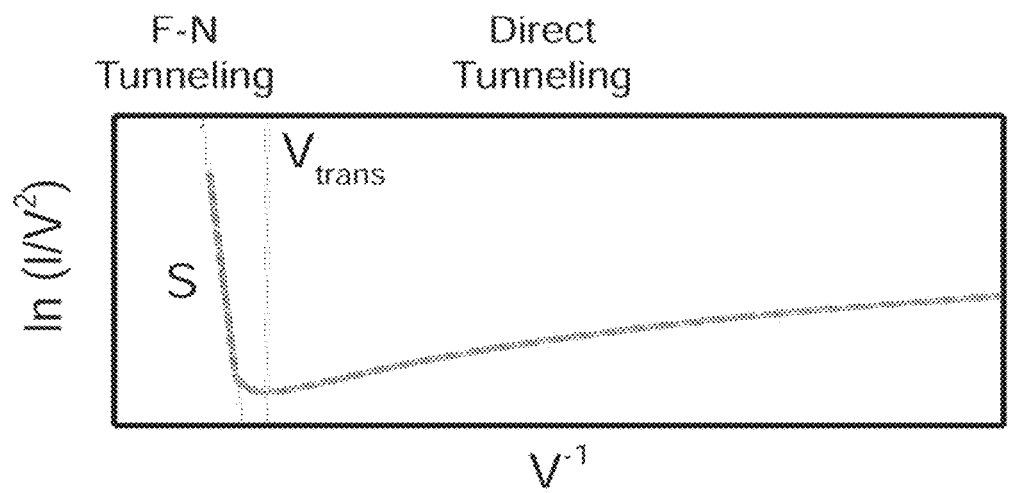

In some cases, differences in biochemistry may be seen with other isomers, and detected using the STS of single nucleotides, under different pH conditions (FIG. 4C, 12, 14, 16). For example, thymine nucleobase (T), unlike adenine, guanine, and cytosine, may tunnel charges (both electrons and holes) through the enol isomers (formed under acidic condition), (FIG. 4C, D, 11, Table I). This effect may be due to due to conjugation. STS spectroscopy through single T nucleotides under acidic, neutral and basic pH demonstrates these biochemical changes, which may be due to ease of tunneling charges through single molecules (FIG. 4C, D). The LUMO level in single T nucleotides decreases with increase in pH due to easier electron tunneling (likely effect of electrostatic repulsion, FIG. 4D, 11, discussed above). Similar effect of pH on the LUMO and HOMO levels is also observed for other nucleotides (FIG. 12, 14, 16). For example, the two pKa values and resulting isomers for guanine can be seen using STS data (FIG. 12, Table I). Therefore, biochemical structure, nucleobase tautomers and other isomers formed under different pH conditions (determined by their pKa values), were tracked using probability of electron and hole tunneling, as monitored using LUMO and HOMO values respectively (along with Band Gap, FIG. 4A, B, C, 12, 14, 16, Table I).

It was hypothesized, using DFT studies, that the presence of protonated and deprotonated acid/base for the nucleotides and keto-enol tautomers of the nucleobases under different pH conditions (e.g. FIG. 11 and as described above), could lead to separation of electron/hole tunneling probability between purines (A,G) and pyrimidines (C,T) under different pH conditions. The resulting quantum molecular sequencing (QM-Seq) electronic signatures would be distinct leading to the development of a robust biochemical nucleotide identification method.

Example 2—Biophysical Parameters as New QM-Seq Signatures

Figure 4F:
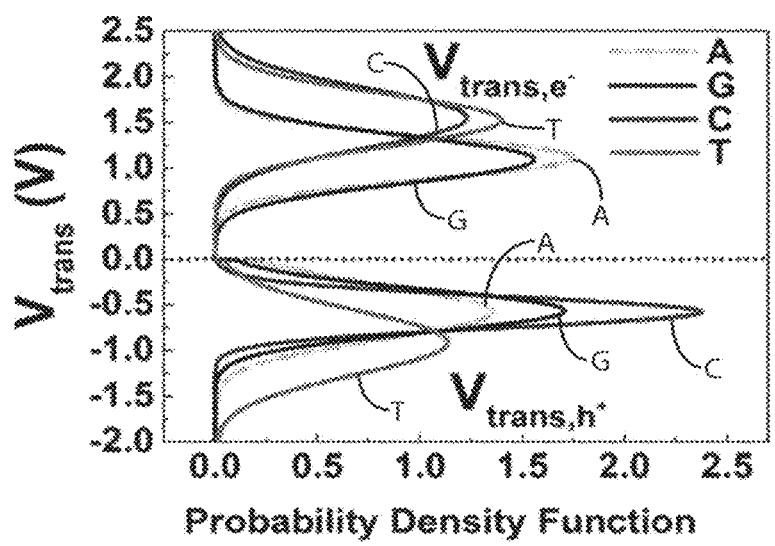

To develop additional biophysical figures of merit or parameters or QM-Seq signatures for facile identification of nucleobases towards sequencing applications, detailed analysis of tunneling current was analyzed from single molecules (deoxynucleotides here). Tunneling current was analyzed using a Fowler-Nordheim (F—N) plot, to identify the underlying biophysical parameters governing charge tunneling through the single nucleotides. The tunneling current (I)-voltage (V) data was plotted as $\ln(I/V^2)$ vs. (I/V), to extract the transition voltage ($V_{trans}$) of the tunneling regime (for triangular barrier), as shown for F—N plot for T in FIG. 4E. The transition voltage, $V_{trans,e-}$, represents the transition from tunneling to field emission regime, and it is a measure of the tunneling barrier (for electrons here). These parameters for electron ($V_{trans,e-}$) and hole ($V_{trans,h+}$) tunneling through the nucleotide sequences represent identifying components of electronic signatures, may be used similarly to HOMO-LUMO and bandgap values to characterize and identify sequences (discussion below). On extracting these parameters for individual nucleotides, as shown in FIG. 4F, we observe distinct separation of $V_{trans,e-}$ and $V_{trans,h+}$ values under acidic conditions (Table III, discussion previously and below). Similar shifts were also observed in electron and hole transition voltage under different pH conditions, as shown in FIG. 21 and Table III). Therefore, using HOMO-LUMO levels, energy bandgap, $V_{trans,h+}$, and $V_{trans,e-}$, as biophysical parameters, we can identify nucleotides using charge (electron and hole) tunneling data.

Figure 7D:
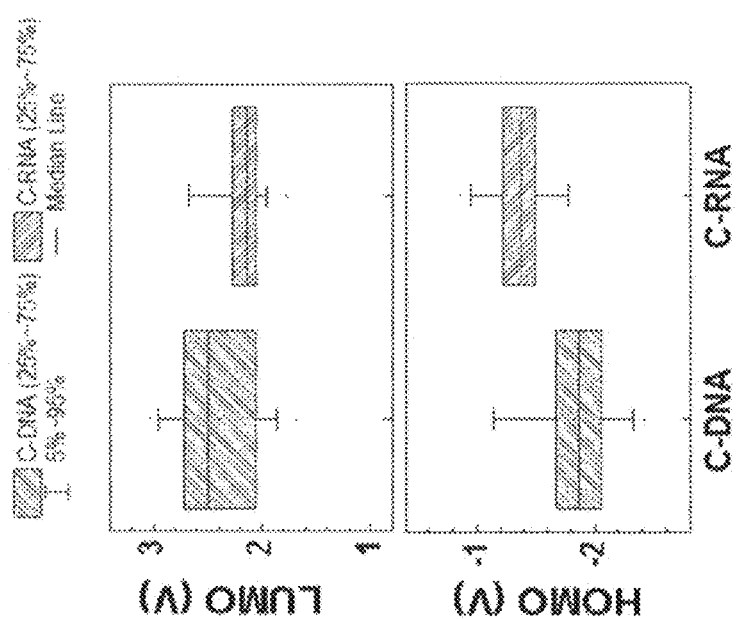
Figure 7C:
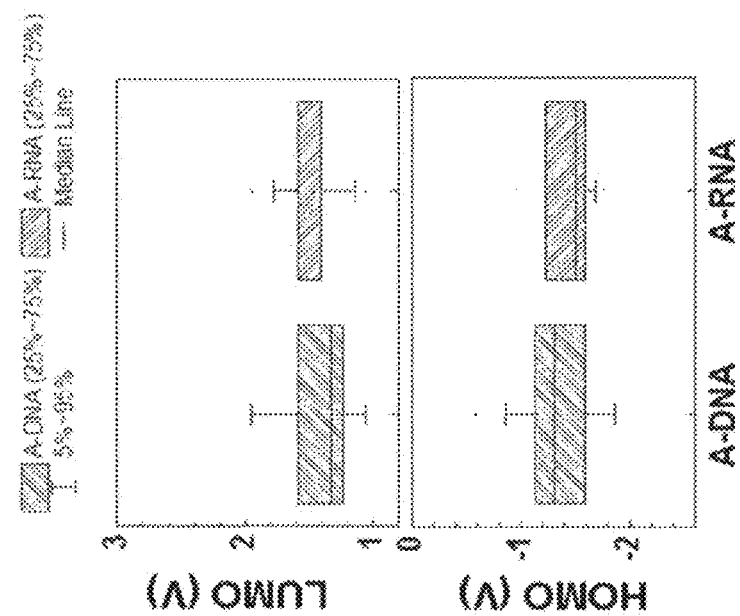

QM-Seq signatures for ribonucleotide identification: Using the DFT investigation, along with the experimental biophysical and biochemical studies, we identified that acidic pH ensures formation of distinguishable signatures ($pK_a$ for A, G, T, and C are 4.1, 3.3, 9.9, and 4.4 respectively) which can be used to reproducibly identify single nucleotides (using energy bandgap, HOMO-LUMO, $V_{trans,h+}$, and $V_{trans,e-}$, FIG. 4 A, B, E, F, QM-Seq data for DNA in Tables I and III, QM-Seq data for RNA in Table II), for fast and accurate electronic identification. Furthermore, DFT studies suggested that quantum signatures or electronic fingerprints for RNA pyrimidine nucleobases can be different from DNA. To evaluate the potential of QM-Seq for direct RNA sequencing and uniqueness of quantum signatures, we measured the QM-Seq biophysical parameters for RNA homo oligonucleotides under acidic conditions (FIG. 7A, B, Table II). Clear separation of QM-Seq signatures allows quick identification of RNA purines (A/G) and pyrimidines (C/U). However, dispersion of signatures due to molecule entropy and delocalization of charge cloud over the 2'hydroxylated sugar backbone prevents further distinction between nucleotides. Comparing the purines (FIG. 7C) and pyrimidines (FIG. 7D) QM-Seq signatures between RNA and DNA shows clear distinction between fingerprints for pyrimidine nucleobases, as suggested by DFT simulations. Since the 2'hydroxylated sugar backbone distinguishes RNA and DNA nucleotides, strong localization of charges to the nucleobases prevents difference in signatures for purine nucleotides (FIG. 7C, Table II). These results outline a relationship between biochemical structure of nucleotides and their QM-Seq signatures, and demonstrate the ability for fast single-molecule sequencing using unique QM-Seq electronic fingerprints.

RNA production using in vitro transcription: RNA samples were prepared using in vitro transcription from extracted DNA genes using MAXIscript kit (Applied Biosystems). We mixed 500-1000 ng of DNA template, 1 μL of ATP 10 mM, 1 μL of CTP 10 mM, 1 μL of GTP 10 mM, 1 μL of UTP 10 mM, 1 μL of nuclease-free water in a PCR tube. Then, 2 μL of 10× transcription buffer was added and mixed thoroughly. Finally, 2 μL of SP6 polymerase enzyme was added to the reaction followed by vortex and spin. All the reagents were kept at room temperature for the assembly except the polymerase (Note that assembling the reaction in ice can precipitate the template DNA). The solution was then incubated for 1 h at room temperature. Following the incubation, 1 μL of TURBO DNase was added to degrade the template DNA and it was incubated at 37° C. for 30 minutes. Then, the solution was transferred to 1.5 mL centrifuge tube and preceded to ethanol precipitation. We added 25 μL of nuclease free water, 5 μL of sodium acetate 3M at pH=5.5 and 3 volumes of chilled absolute ethanol. The solution was incubated at −20° C. for at least 30 minutes. Then, the product was centrifuged at maximum speed for 15 minutes followed by two washing with ethanol (70%). Finally the RNA pellet was re-suspended on 15 μL of 0.5×TE buffer.

Figure 30:
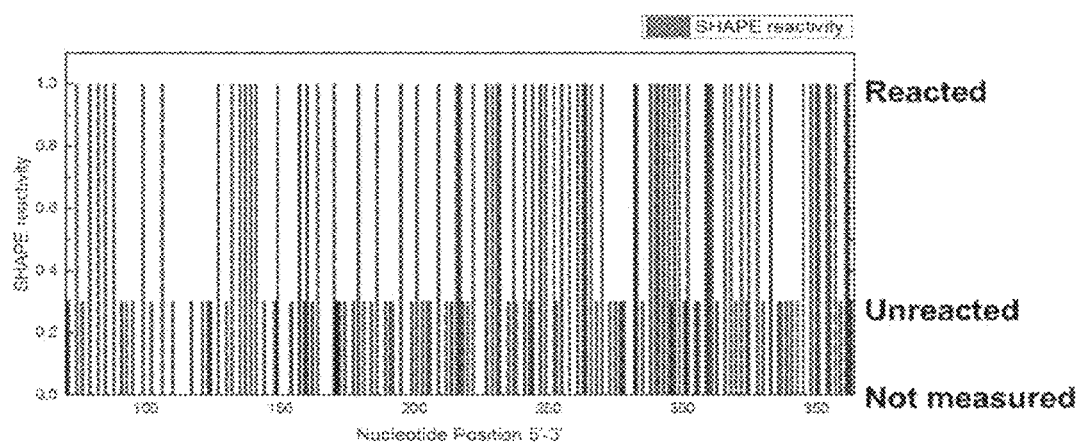
FIG. 30: Structure determination based on the reactivity. The figure shows assignment of reacted vs. unreacted nucleotides during RNA structure determination The secondary/tertiary nucleic acid structure, RNA here, was obtained using electronic fingerprints of chemical modification with RNA SHAPE and/or DMS molecule, and using RNA Structure software with constrained single-stranded regions where SHAPE or DMS had reacted.
Figure 32:
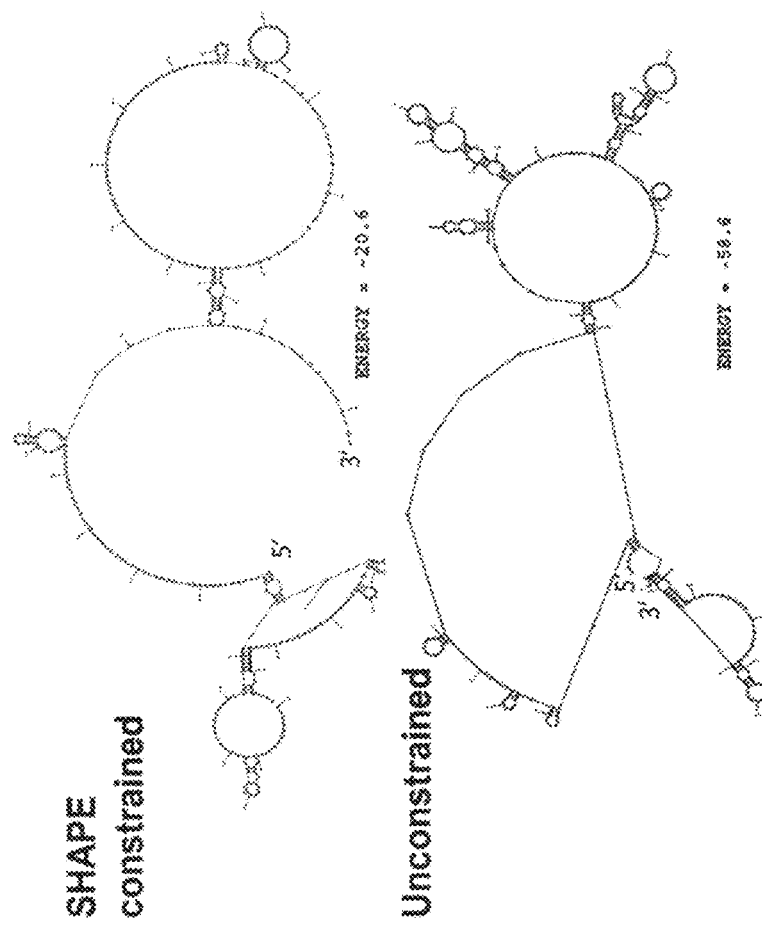
FIG. 32: RNA structure of HIV-RNase measured experimentally with QM-Seq (upper panel). Lower panel shows an in silico unconstrained RNA structure predicted using RNA folding software.
Figure 33A:
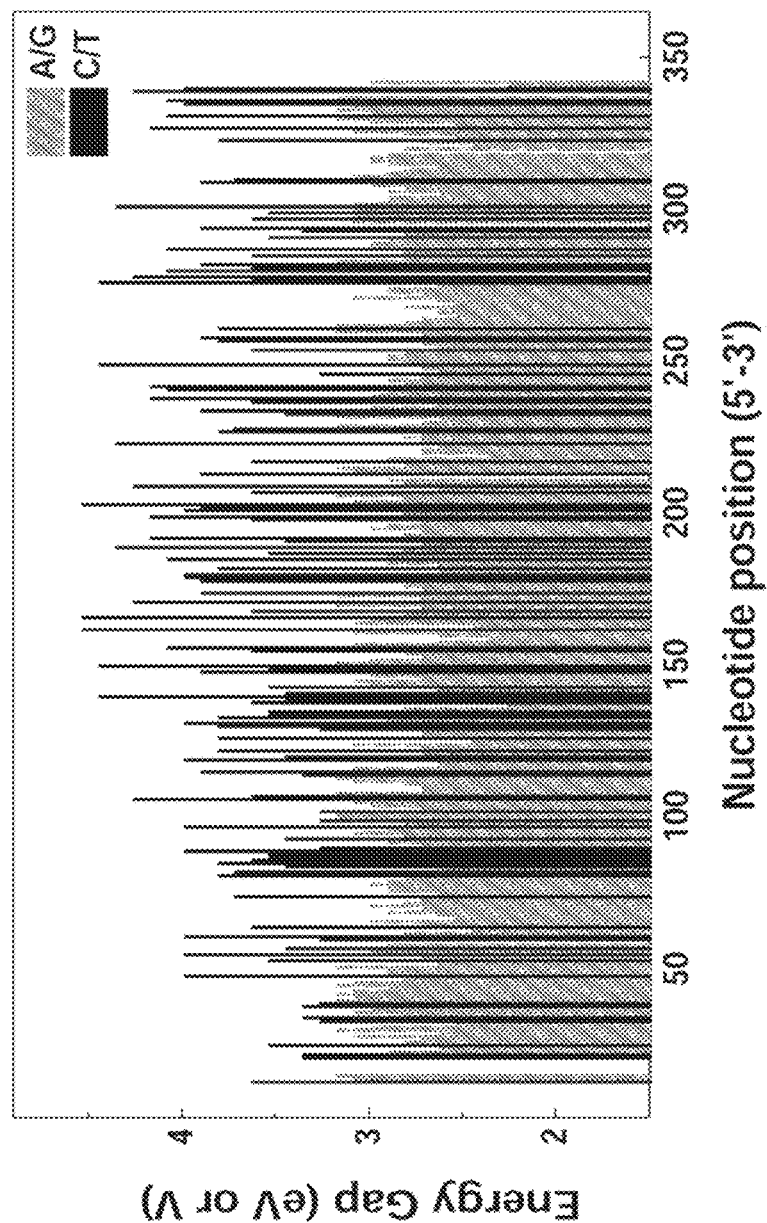
FIG. 33A-B: Comparison between using (top) 3 parameter electronic states (HOMO-LUMO-Energy gap), and (bottom) multidimensional biophysical parameters (>9 parameters, including but not limited to HOMO, LUMO, Energy gap, tunneling barrier heights for electron and holes, difference in tunneling barrier heights, voltages corresponding to change in tunneling barrier profile from direct tunneling to Fowler-Nordheim tunneling for electron and holes, effective masses of electrons and holes in nucleotide tunneling, ratio of effective electron and hole masses, slopes of corresponding Fowler-Nordheim plots), all calculated from quantum tunneling spectroscopy scans and used as electronic fingerprints, obtained by QM-Seq on HIV-1 RNAse. The electronic states can help in identification between RNA purines and pyrimidines, but the multi-variable electronic fingerprints allow unique identification of all four nucleobases with high precision, as shown in this figure (bottom).
Figure 33B:
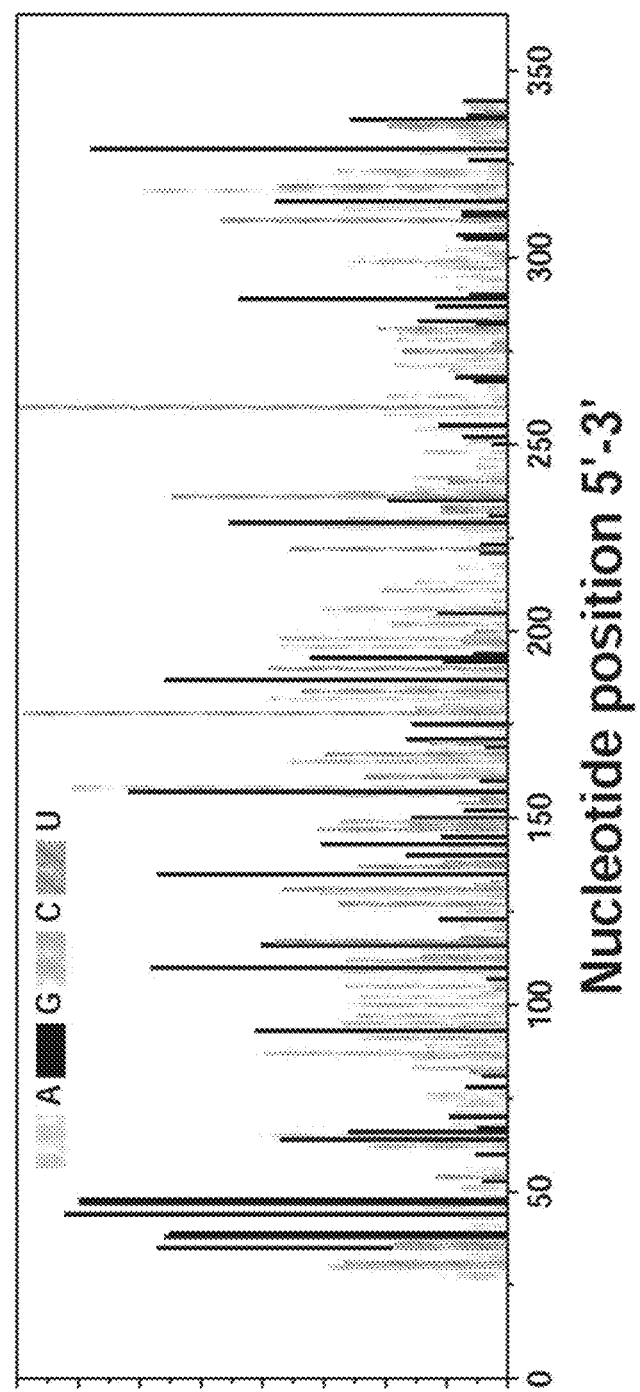

RNA modification with N-methyl isatoic anhydride: On 10 μL of folded RNA add 10 μL of N-methyl isatoic anhydride (NMIA) solution (130 mM of NMIA in DMSO). Incubate at 37° C. for 2.5 hours. Follow the reaction with ethanol precipitation as described above. Re-suspend RNA pellet in 10 μL of 0.5×TE buffer. This NMIA electrophile addition for Selective 2' Hydroxyl Acylation Analyzed by Primer Extension (or SHAPE) is used to determine RNA structure. Such analysis of chemical modification in single molecules using QM-Seq (FIG. 30) was used to determine single-molecule RNA structure for HIV-1 sample (FIG. 32).

RNA Modification with Dimethyl Sulfate: On 10 μL of folded RNA add 10 μL of DMS solution (0.8 mM of DMS (Dimethyl sulfate, SPEX CertiPrep, USA) in methanol). Incubate both tubes at 37° C. for 2 hours. Follow the reaction with ethanol precipitation as described above. Re-suspend RNA pellet in 10 μL of 0.5×TE buffer.

Data analysis: Several parameters were extracted from each the tunneling current data from each nucleobase (HOMO, LUMO, Band Gap, Transition voltage (positive and negative), ratio of electron/hole effective masses, $\varphi_0$ for electron and hole and $\Delta\varphi_0$). We have developed a sorting algorithm that can be used to identify both sequence and structure simultaneously (FIG. 1).

Figure 31:
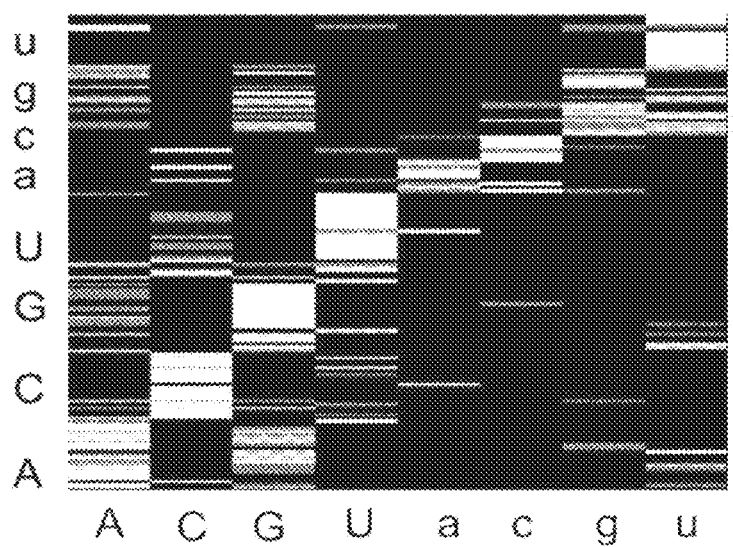
FIG. 31: The Clustering method assigns the RNA nucleotides with high confidence. The diagonal indicates accurate base calling. Letters in uppercase are the unmodified RNA nucleotides, letters in lower case are the modified RNA nucleotides.

First, parameters were identified, for example, HOMO, LUMO, Band Gap, Transition voltage (positive and negative), ratio of electron/hole effective masses, $\varphi_0$ for electron and hole and $\Delta\varphi_0$, on either unmodified homo oligomers or modified (either with NMIA or DMS). Identified parameters from individual modified/unmodified oligos (as determined on training sets from well-characterized, known sequences, such as homopolynucleotides containing or lacking modifications) were used to construct a machine learning model (for example a Naive-Bayes model, which classifies previously defined groups based on Bayesian probability that the new data point belongs in a specific group. In this model, parameters are assumed (naively) that they are independent from each other and compared to the reference. Then, the overall score or probability to pertain in each group is computed and provided as output. The highest score/probability from certain group is defined as called group) as a reference. Then, unknown spectra were processed to extract the parameters and those were compared against the training set to identify the probability of each individual group from the training set (FIG. 31). The group with highest probability is assigned to the original spectra and used for sequence alignment. This methodology allows identification of both sequence and structure simultaneously. Other machine learning processes or algorithms for data classifications (supervised machine learning) that can be used include: Analytical learning, Artificial neural network, Backpropagation, Boosting (meta-algorithm), Bayesian statistics, Case-based reasoning, Decision tree learning, Inductive logic programming, Gaussian process regression, Group method of data handling, Kernel estimators, Learning Automata, Minimum message length (decision trees, decision graphs, etc.), Multi-linear subspace learning, Naive bayes classifier, Nearest Neighbor Algorithm, Probably approximately correct learning (PAC) learning, Ripple down rules, a knowledge acquisition methodology, Symbolic machine learning algorithms, Sub-symbolic machine learning algorithms, Support vector machines, Random Forests, Ensembles of Classifiers, Ordinal classification, Data Pre-processing, Handling imbalanced datasets, Statistical relational learning, Proaftn, and multi-criteria classification algorithm.

Figure 34A:
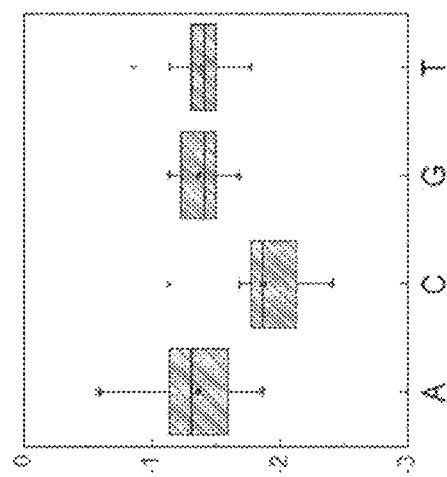
FIGS. 34A-H: Different Biophysical parameters used as electronic fingerprints for DNA nucleotide (A,T,G,C) identification determined on a poly-lysine coated ultraflat Au(111) substrate in acidic conditions. a) LUMO-level b) HOMO-level c) Barrier height for electrons d) Barrier height for holes e) Total tunneling barrier height for molecule f) ratio of effective electron and hole masses for charge tunneling through individual nucleotides. Transition voltage from direct to Fowler-Nordheim tunneling for g) electrons and h) holes.
Figure 34B:
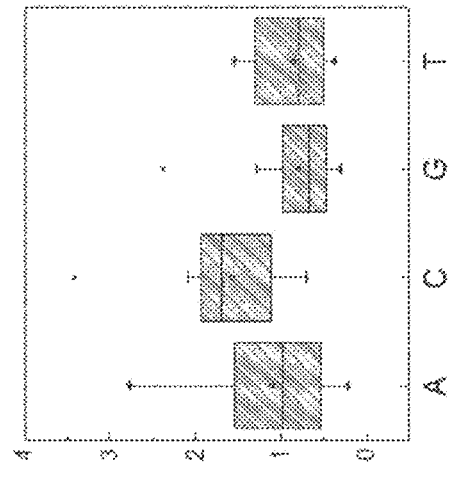
Figure 34C:
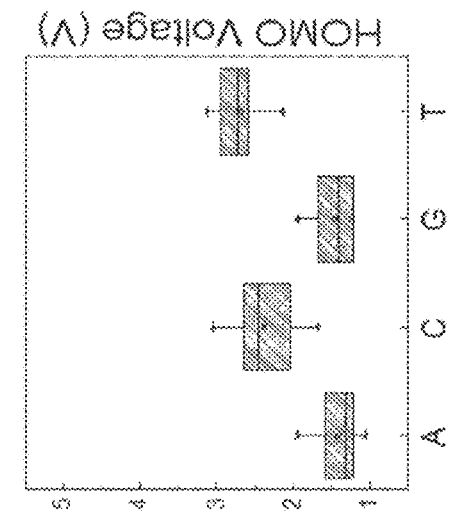
Figure 34D:
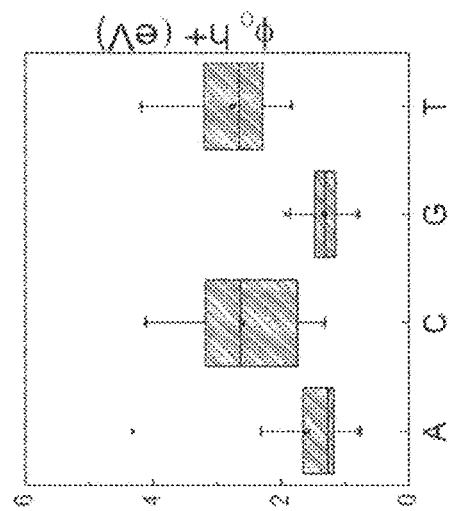
Figure 34E:
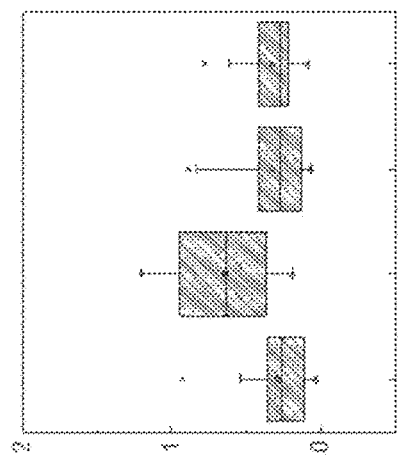
Figure 34F:
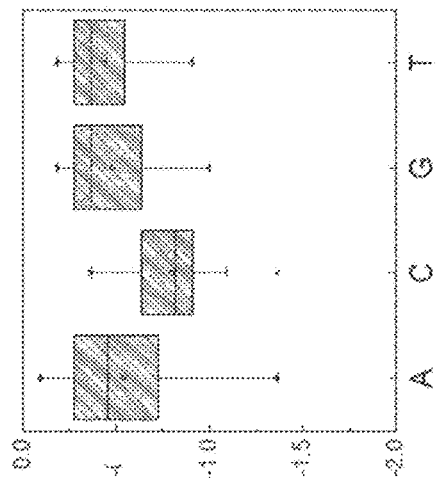
Figure 34G:
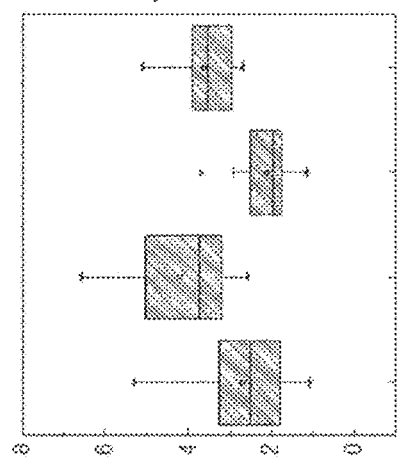
Figure 34H:
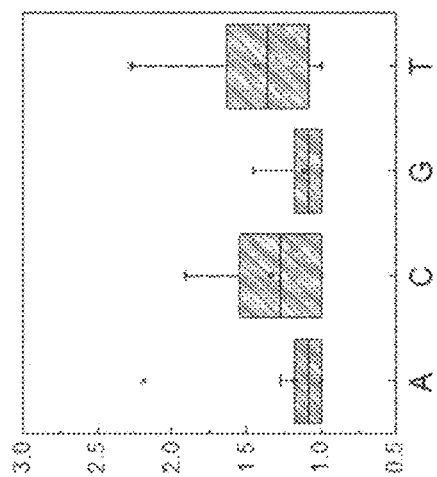
Figure 35A:
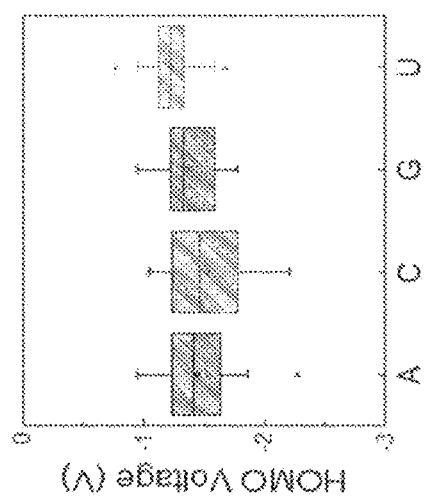
FIGS. 35A-H: Different Biophysical parameters used as electronic fingerprints for RNA nucleotide (A,U,G,C) identification on modified Au(111) substrate in neutral conditions. (a) LUMO-level; (b) HOMO-level; (c) Barrier height for electrons; (d) Barrier height for holes; (e) Total tunneling barrier height for molecule; (f) ratio of effective electron and hole masses for charge tunneling through individual nucleotides. Transition voltage from direct to Fowler-Nordheim tunneling for (g) electrons and (h) holes.
Figure 35B:
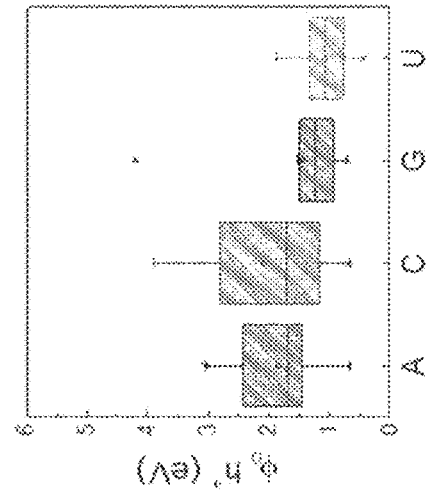
Figure 35C:
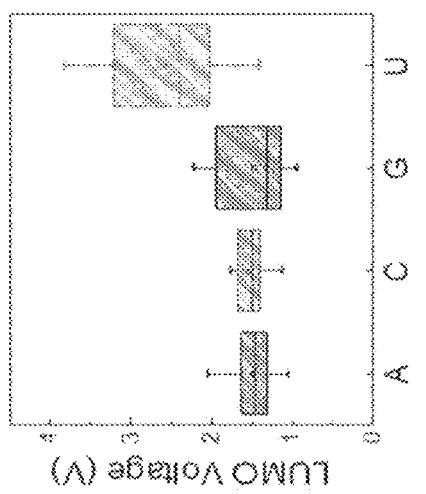
Figure 35D:
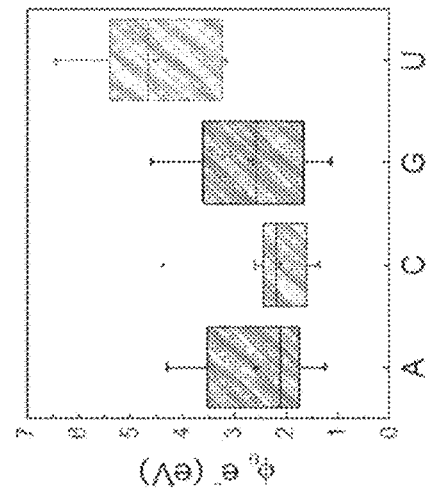
Figure 35F:
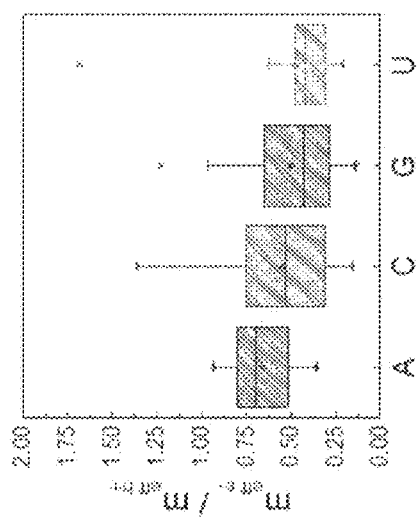
Figure 35H:
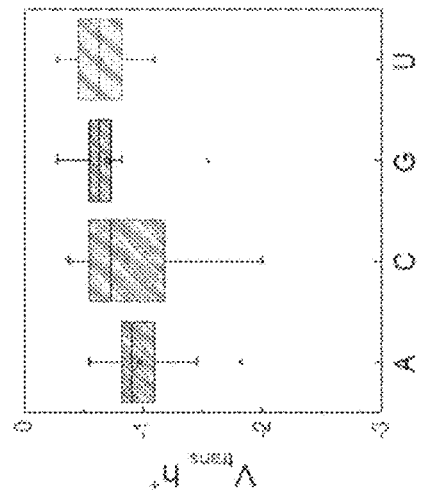
Figure 35E:
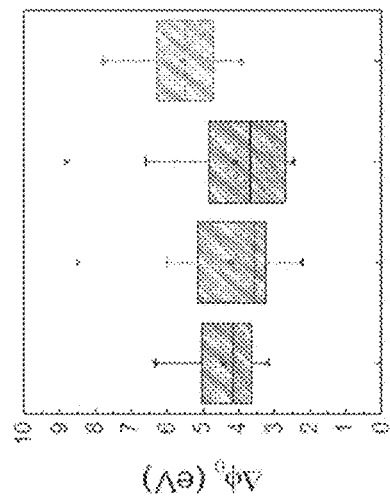
Figure 35G:
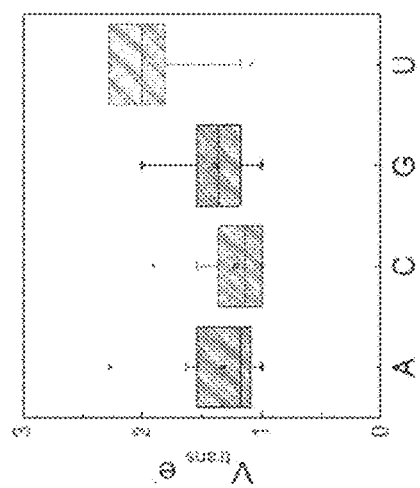

In other embodiments, values for parameters derived from the tunneling current data were identified, for example, HOMO, LUMO (FIG. 34A,B), Band Gap, Transition voltage (positive and negative), ratio of electron/hole effective masses, $\varphi_0$ for electron and hole and $\Delta\varphi_0$ (FIG. 34C,D). These values were identified for both unmodified homo oligomers or modified (either with NMIA or DMS) homo oligomers in various environments. These identified parameters, referred to as "training sets" were obtained from well-characterized, known sequences, such as homopolynucleotides containing or lacking modifications. The parameter values from the training sets were then used to construct a machine learning model as a reference. Various machine learning models may be used, for example a Naïve-Bayes model, which classifies previously defined groups based on Bayesian probability that the new data point belongs in a specific group. In this model, parameters are assumed (naively) to be independent from each other and compared to the reference. Then, an overall score or probability that the new data point belongs in each group is computed and provided as output. The highest score/probability from a certain group is defined as a called group.

Next, tunneling current data is collected for unknown nucleobases. This tunneling current data was processed to determine values for the various parameters: HOMO, LUMO, Energy Bandgap $V_{trans, e-}$, $V_{trans, h+}$, $\phi_{0,e-}$, $\phi_{0,h+}$, $\Delta\phi$ and $m_{eff\,e-}/m_{eff\,h+}$. These values were then compared against values obtained from the training sets in order to identify the probability that the unknown nucleobase belongs to an individual group from the training set. The called group (the group with highest probability of matching the unknown nucleobase's group) is assigned to that nucleobase and used for sequence alignment. This methodology allows identification of both sequence and structure simultaneously. Other machine learning processes for data classifications (supervised machine learning) that can be used include: Analytical learning, Artificial neural network, Backpropagation, Boosting (meta-algorithm), Bayesian statistics, Case-based reasoning, Decision tree learning, Inductive logic programming, Gaussian process regression, Group method of data handling, Kernel estimators, Learning Automata, Minimum message length (decision trees, decision graphs, etc.), Multi-linear subspace learning, Naive bayes classifier, Nearest Neighbor Algorithm, probably approximately correct (PAC) learning, Ripple down rules, a knowledge acquisition methodology, Symbolic machine learning algorithms, Sub-symbolic machine learning algorithms, Support vector machines, Random Forests, Ensembles of Classifiers, Ordinal classification, Data Pre-processing, Handling imbalanced datasets, Statistical relational learning, Proaftn, and multi-criteria classification algorithm.

Example 3—Transition Voltage Values

Detailed analyses of tunneling current data from single molecules (nucleotides here) was also conducted to further aid in identification of nucleobases in sequencing applications. For these experiments, tunneling current was analyzed using a Fowler-Nordheim (F—N) plot. This analysis was performed to identify underlying biophysical parameters governing charge tunneling through the single nucleotides. Tunneling current (I)-voltage (V) data was plotted as $\ln(I/V/V^2)$ vs. (1N), in order to extract the transition voltage ($V_{trans}$) and the slope of the tunneling regime (for triangular barrier). An example of this analysis is shown in the F—N plot for T in FIG. 4E. The transition voltage, $V_{trans,e-}$, represents the transition from tunneling to field emission regime, and the slope, S, is a measure of tunneling barrier (for electrons here).

On careful analysis of tunneling parameters, like transition voltage from tunneling to field emission, and the slope indicating the barrier for charge tunneling, three biophysical parameters/constants may be extracted. These tunneling constants ($V_{trans,h+}$, $V_{trans,e-}$, $S=S_e+S_h$) were characteristic of the molecule through which charges are tunneled (nucleotides here), and were used to develop additional figure of merits to HOMO-LUMO and bandgaps, respectively. For example, on analyzing the change in hole tunneling probabilities using $V_{trans,h+}$, it was observed that it can be used like HOMO level for nucleotides under different pH conditions (FIG. 21, Table III). Similarly, $V_{trans,e-}$ represents the ease of electron tunneling (lower value shows easier electron tunneling), like LUMO level. Slope S mimics the bandgap observed in these biomolecules. On more careful analysis, similar behavior was observed for these Fowler-Nordheim (F—N) transition voltages ($V_{trans}$) (FIG. 21, Table III). $V_{trans}$ represents the shift from triangular tunneling to field emission of either electrons or holes. $V_{trans}$ show the same pattern with pH as the HOMO ($V_{trans,h+}$) and LUMO ($V_{trans,e-}$) level which confirms the biophysical theory behind F—N tunneling applied for biomolecules like DNA. Hence, these tunneling parameters can be used as additional new QM-Seq signatures/figures of merit developed in this work.

Using the transition from direct tunneling to Fowler-Nordheim tunneling in biomolecules by measuring the transition voltage ($V_{trans}$), we estimate the tunneling barrier height (energy offset between the metal tip Fermi level ($E_F$) and the frontier molecular orbital, i.e. either HOMO or LUMO). When the applied bias voltage (bias) is less than the barrier height, direct tunneling is assigned to the dominant transport mechanism. In the zero-bias limit, the barrier is assumed to be rectangular, and can be approximated as where is the effective electron mass, is the barrier height, d is the tunneling distance, and h ($h=h/2\pi$) is the Planck's constant. At high bias voltage, conduction mechanism is dominated by Fowler-Nordheim tunneling, or field emission, and the triangular barrier can be approximated. Therefore, the transition from direct tunneling (logarithmic on F—N plot) to Fowler-Nordheim tunneling (linear on F—N plot) exhibits an inflection point ($V_{trans}$) on the F—N plot ($\ln(I/V^2)$ vs. $1/V$). The transitions in shape of the tunneling curve from a rectangular ($V=0$ V) to a trapezoidal ($V<\varphi_B/e$) then to a triangular form ($V>\varphi_B/e$) can be seen with increasing bias. Therefore, $V_{trans}$ provides an experimental method to measure the transition from rectangular to triangular barrier, thus measuring the height of the original rectangular barrier associated with the tunneling transport in biomolecules.

These experiments indicate that the parameters for electron ($V_{trans,e-}$) and hole ($V_{trans,h+}$) tunneling through the nucleotide sequences represent signature components, and may be used similarly to HOMO-LUMO and Band Gap values to characterize and identify sequences. On extracting these parameters for individual nucleotides, as shown in FIG. 4F, separation of $V_{trans,e-}$ and $V_{trans,h+}$ values under acidic conditions can be observed (Table III, and discussions above). Similar shifts in electron and hole transition voltage under different pH conditions was also observed, as shown in FIG. 21 and Table III. Therefore, using HOMO-LUMO levels, $V_{trans}$ and slope (S) as components of identifying signatures (or parameters), nucleotides can be separated using charge (electron and hole) tunneling data.

Example 4—AmpR and HIV-1 RNase Sequencing

For example, and as describe more thoroughly below, the disclosed technique was used to determine electronic fingerprints (or tunneling data) on a sequence of an 85 and a 700 nt region of ampR gene, which encodes resistance to beta-lactam antibiotics; and a 350 nt region of HIV-1 RNase sequence. To determine the secondary and tertiary structure of single RNA molecules, we also using an NMIA SHAPE modification (FIG. 32) and determined the unreacted and reacted regions. The presently disclosed technique succeeded in these sequencing projects with over 95% success rate in a single Quantum Molecular Sequencing scan/read, where success is defined as matching the identity of the unknown nucleotide with the identity of the known sequence. In many embodiments, the success rate may be greater than about 96%, 97%, 98%, or 99%.

Using the biophysical and biochemical studies described above, it was determined that an acidic pH could be used to promote the formation of distinguishable isomers (pKa for A, G, T, and C are 4.1, 3.3, 9.9, and 4.4 respectively), and that these distinguishable isomers can be used to reproducibly sequence single nucleotides (using Band Gap, HOMO-LUMO, $V_{trans}$ and S, FIG. 4A, B, E, F).

Figure 5B:
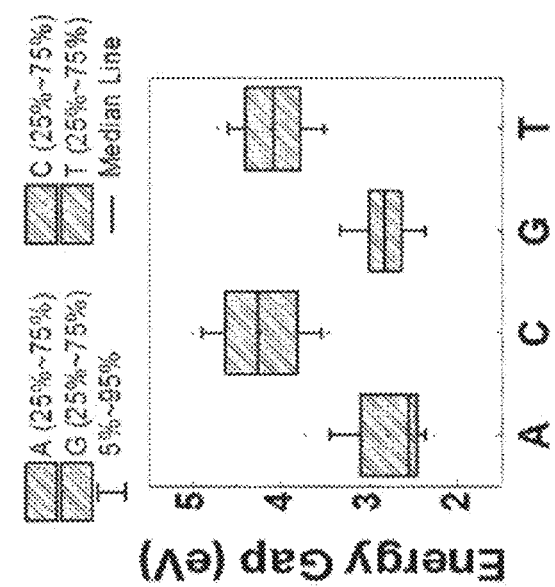
Figure 5A:
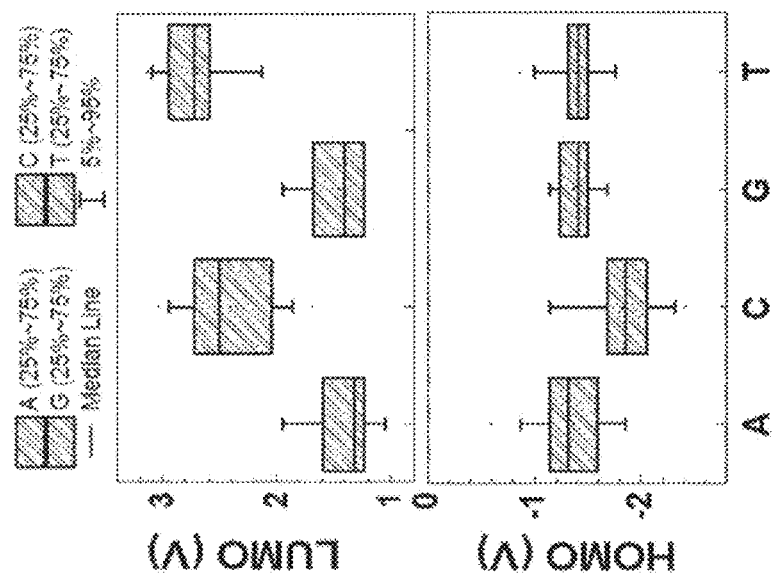
Figure 22A:
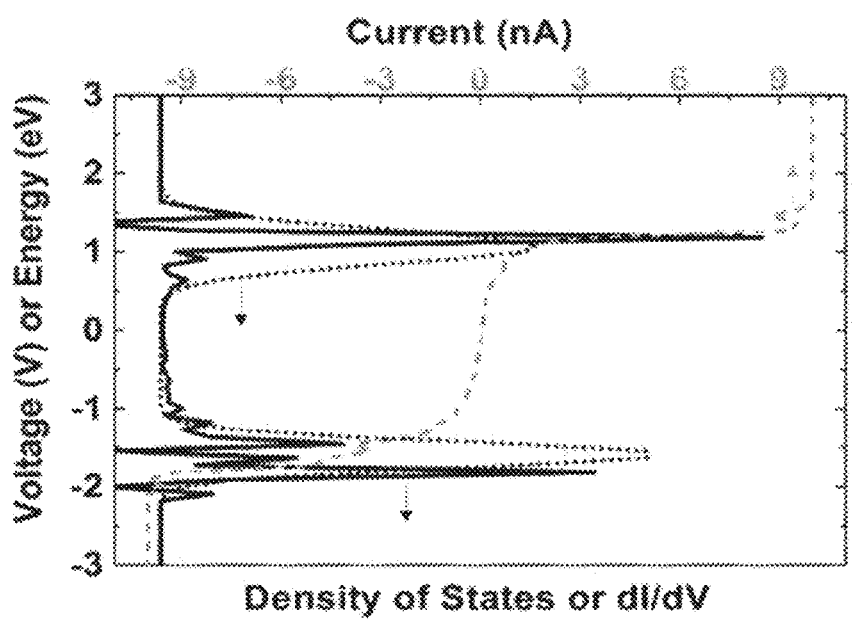
FIGS. 22A-C: Tunneling properties of DNA nucleotides Guanine, Cytosine and Thymine. I-V (dashed line), dI/dV or density of states (solid line) and probability distribution of LUMO and HOMO levels (dotted line) for Guanine (a), Cytosine (b) and Thymine (c). The dotted lines are the normal probability distribution functions fitted for both LUMO and HOMO energy levels.
Figure 22B:
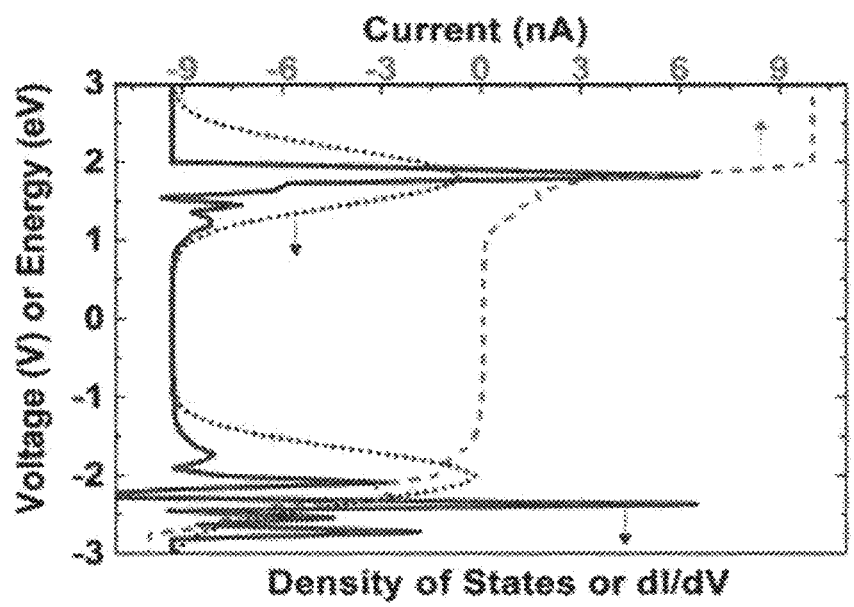
Figure 22C:
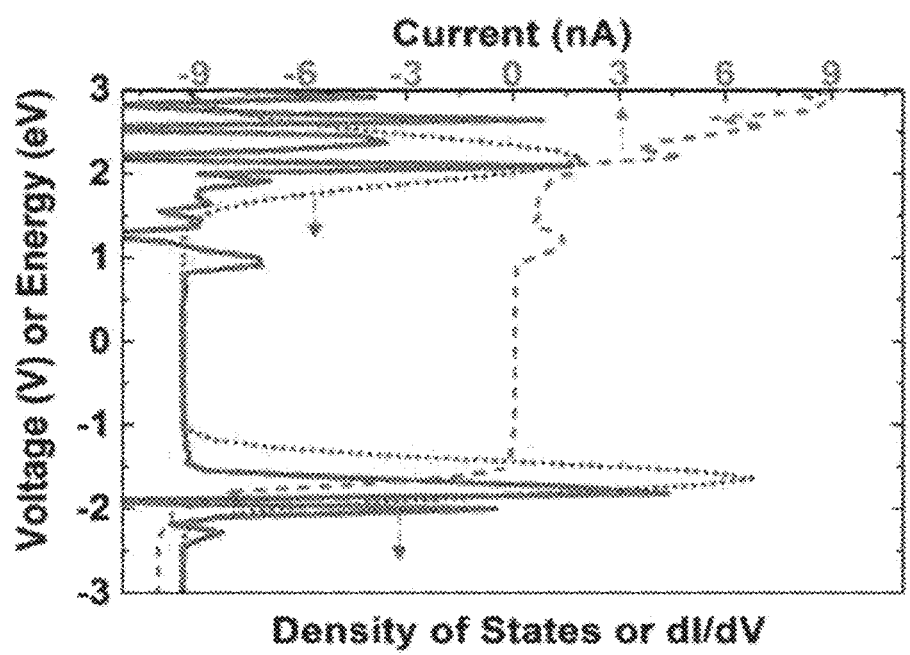

In these experiments, a single STM-STS measurement, under acidic pH, was used to sequence single molecule DNA (using STM) and single nucleotides (using STS data, shown for A in FIG. 5A and T, G, C, in FIG. 22). This was achievable within a time scale of minutes.

Figure 24B:
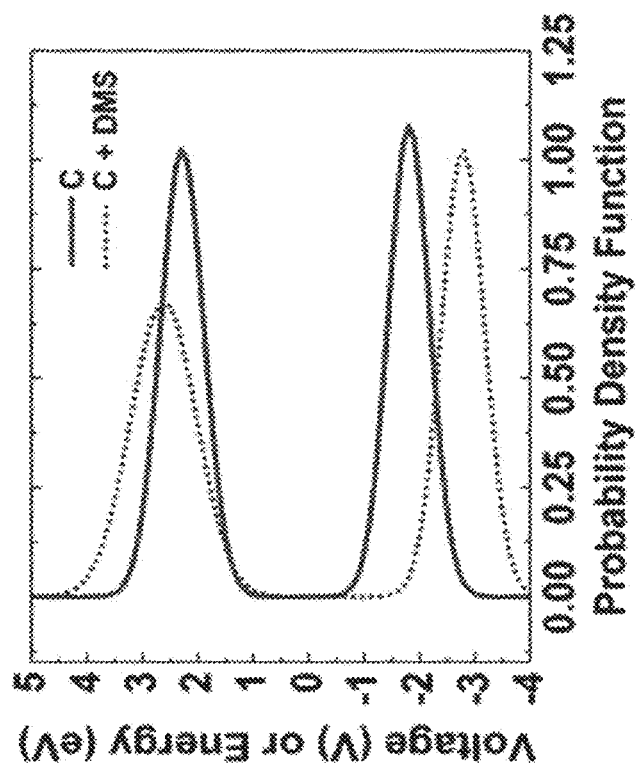
FIGS. 24A-B: Identification of single nucleotide modifications using STM-STS. (a) Reaction products of methylation of Cytosine with DMS. (b) HOMO and LUMO energy levels distribution for cytosine and methylated cytosine deposited on poly-lysine modified Au (111) surface, under acidic conditions. Addition of a methyl group shifts the HOMO level by reducing the hole tunneling probability.
Figure 24A:
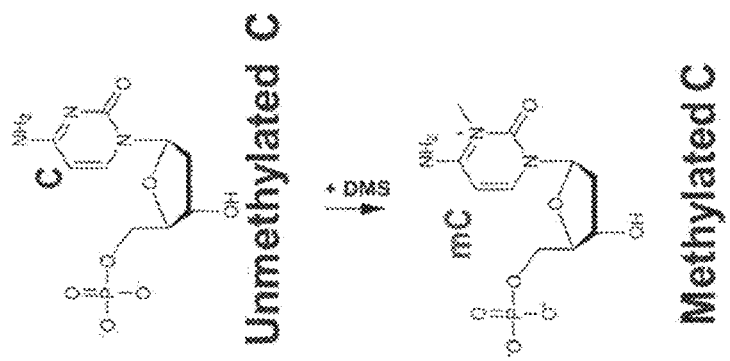

In order to demonstrate the simplicity of this method, and potential applications to study drug resistance and mutating pathogens, sequencing of bacterial antibiotic resistance gene ampR was performed. The ampR gene is useful for pathogenic treatment because it encodes β-lactamase which inhibits penicillin derived antibiotics. A ssDNA solution was prepared, with low concentrations (1-5 nM) to mimic physiological levels (see below, FIG. 24).

Figure 25:
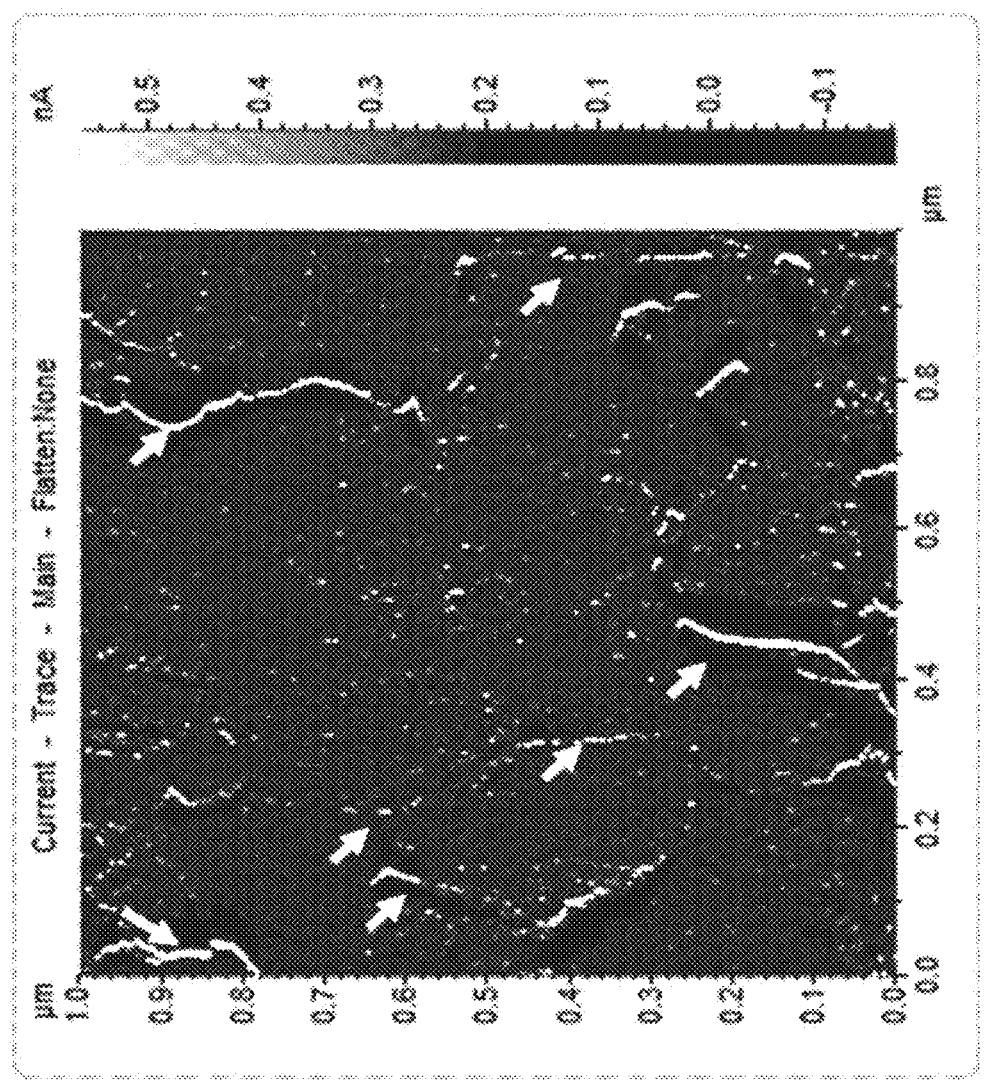
FIG. 25: Single molecule DNA detection capability. Using a low concentration of ssDNA (1-5 nM in doubly distilled water or TE buffer (Tris(hydroxymethyl)aminomethane-Ethylenediaminetetraacetic acid (or EDTA) buffer) to mimic physiological concentration, using the disclosed technique several DNA linearized strands can be detected using STM-STS sequencing. In a sample scan shown here, DNA molecules were found in a small scan area (1 μm×1 μm) on ultrasmooth Au(111) substrate. This demonstrates the capability of this sequencing technique to detect and sequence very low concentrations of DNA molecules.
Figure 26:
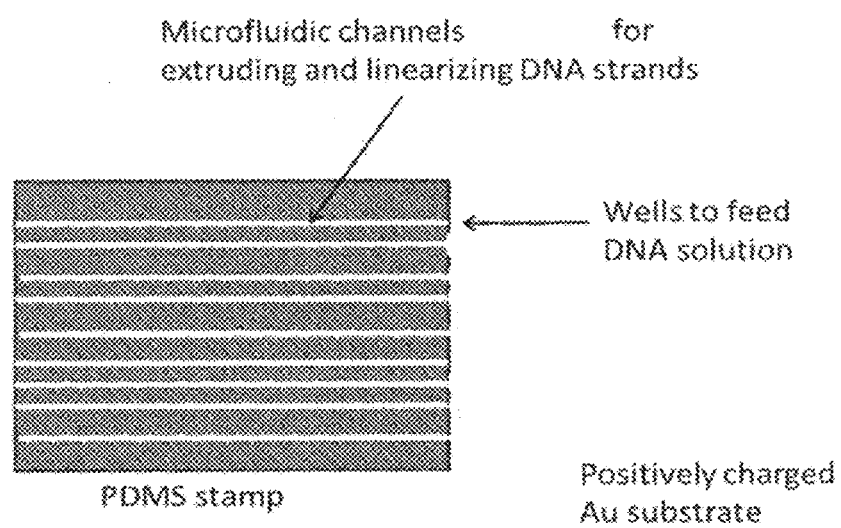
FIG. 26: Depicts a substrates forming channels in a microfluidic device. The channel dimensions (width) can vary between 100 nanometers (nm=$10^{-9}$ m) to 50 micrometers μm.

Single stranded DNA of ampicillin resistance gene (ampR) gene was obtained in two steps. Firstly, double stranded ampR DNA was amplified from plasmid pZ12LUC plasmid (Expressys, Germany) by performing polymerase chain reaction (PCR) using Phusion High-Fidelity PCR Kit (Thermo Scientific, USA). Plasmid pZ12LUC was extracted from *Escherichia coli* strain DH5α-Z1 using genejet plasmid miniprep kit (Thermo Scientific, USA). Forward (CGAGCTCGTAAACTTGGTCTGA) (SEQ ID NO: 1) and reverse primers (GTGAAGACGAAAGGGCCTCG) (SEQ ID NO: 2) (Invitrogen, USA) were used to amplify 1091 bp of ampR gene. Single stranded ampR DNA was obtained by second round of PCR using double stranded ampR as the template DNA and only the forward or reverse primer. The products of each reaction were purified using gel extraction with ZymoClean Gel DNA recovery kit (Zymo Research, USA) and diluted to 5 nM (1.7 ng/μL) in 0.1M $Na_2SO_4$ (to mimic physiological concentrations, FIG. 25). DNA concentrations were measured using NanoDrop 2000 spectrophotometer (Thermo Scientific, USA).

Figure 6A:
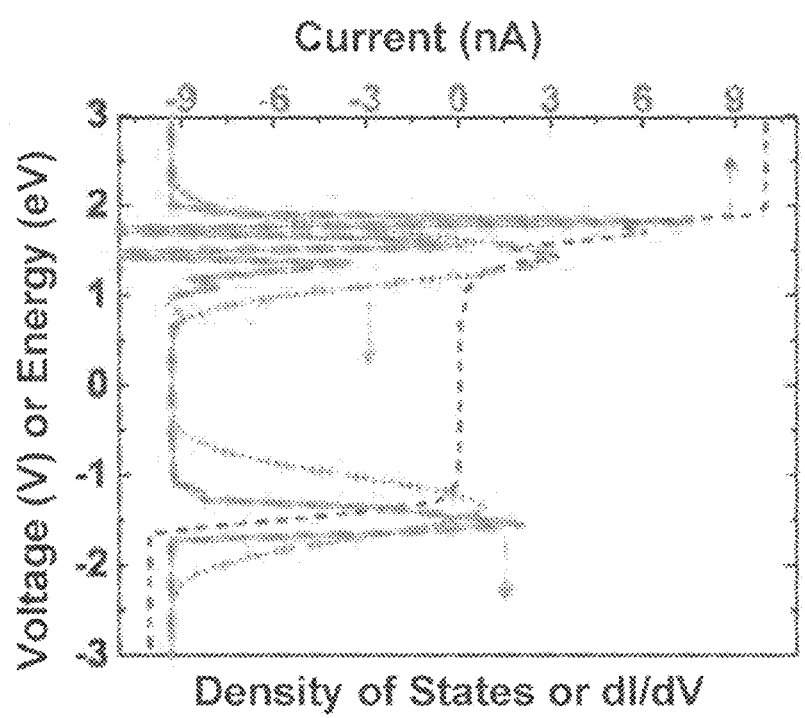
Figure 6B:
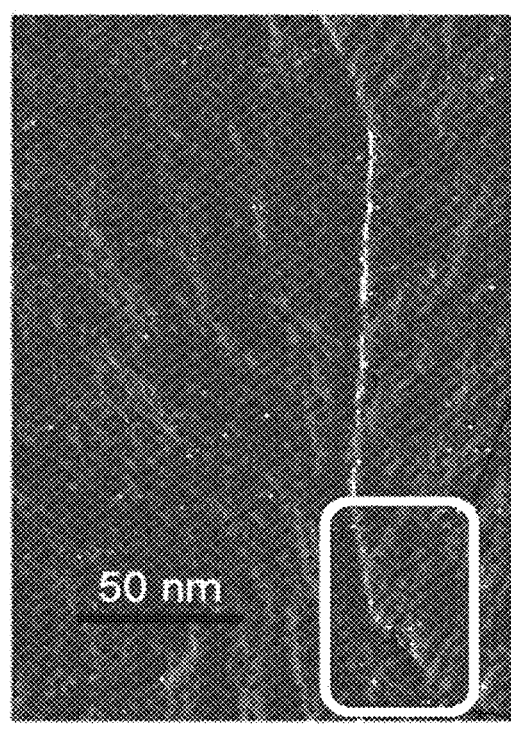
Figure 6C:
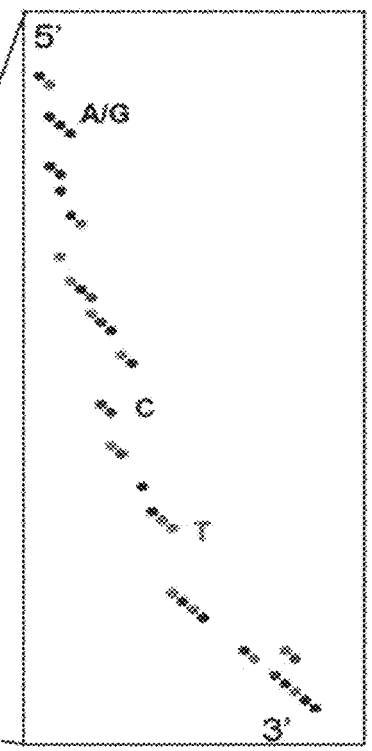
Figure 6D:
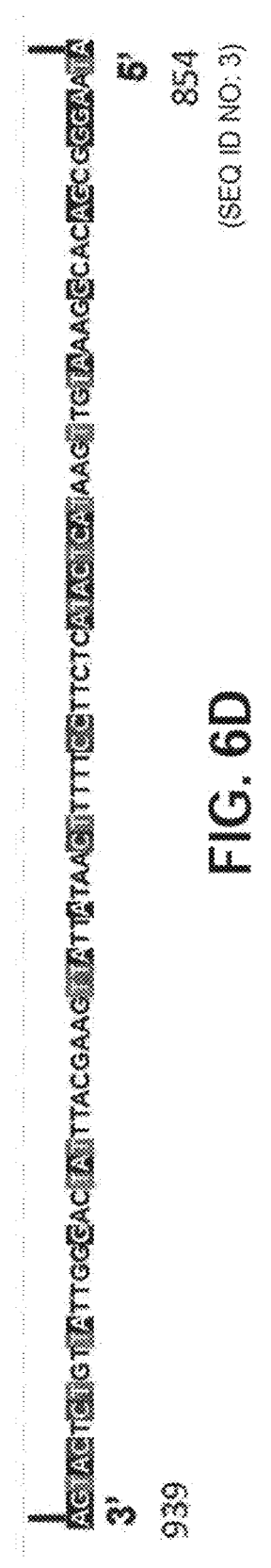

Using the three-step extrusion deposition technique described above, single molecules of elongated linear strands of ssDNA were reproducibly deposited on the substrate (FIG. 6B, and FIG. 23). Simultaneous STM imaging and STS spectroscopy of single strands of ampR DNA was performed (as shown in FIG. 6B, c, d). The STS scan measurement setup had a lateral resolution of 1 nm (limited by the resolution of our piezo scanner and setup, see below). Using the STS scans, nucleotides were correctly identify on each measurement, and adjacent nucleobases were also identified using secondary identification technique (see Methods), with over 95% accuracy (FIG. 6C). Overall, a total of 40 nucleotides were successfully identified within an 85 base region on ampR gene (FIG. 6C, D).

Figure 3B:
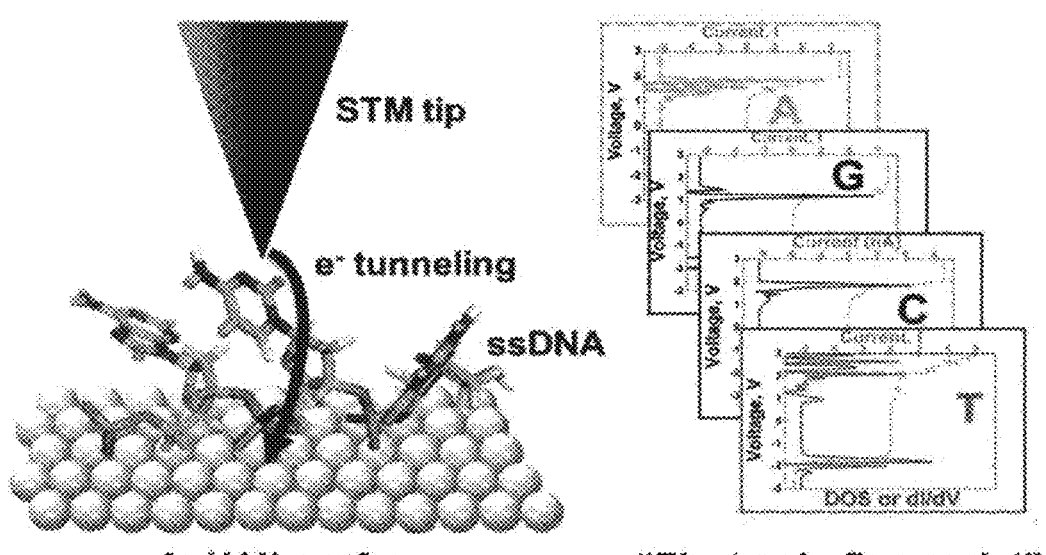
Figure 3C:
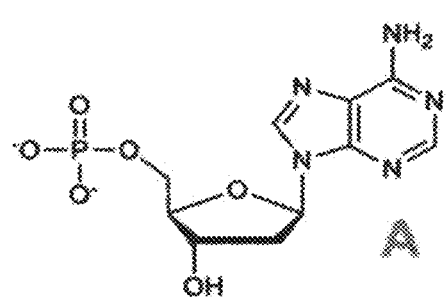
Figure 3D:
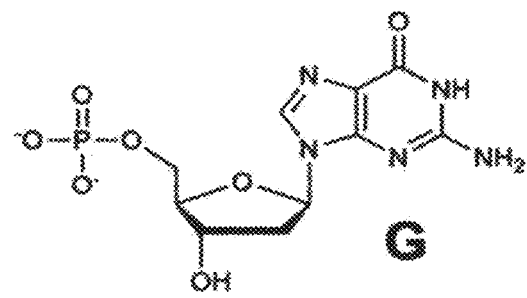
Figure 3E:
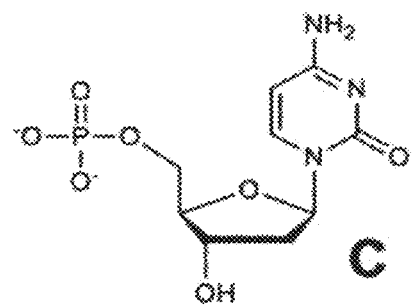
Figure 3F:
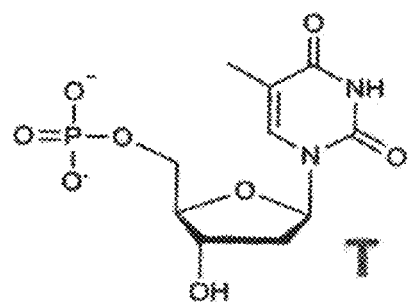
Figure 27A:
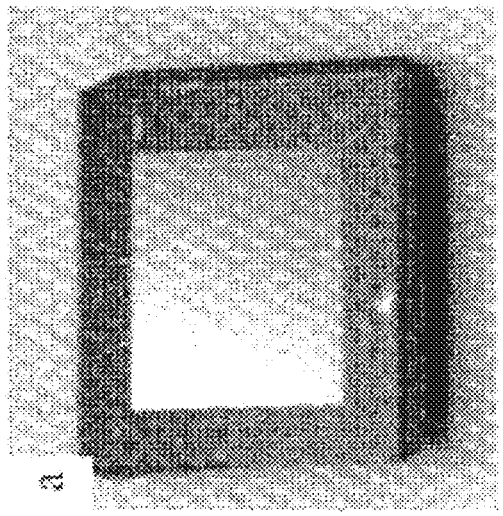
Figure 27C:
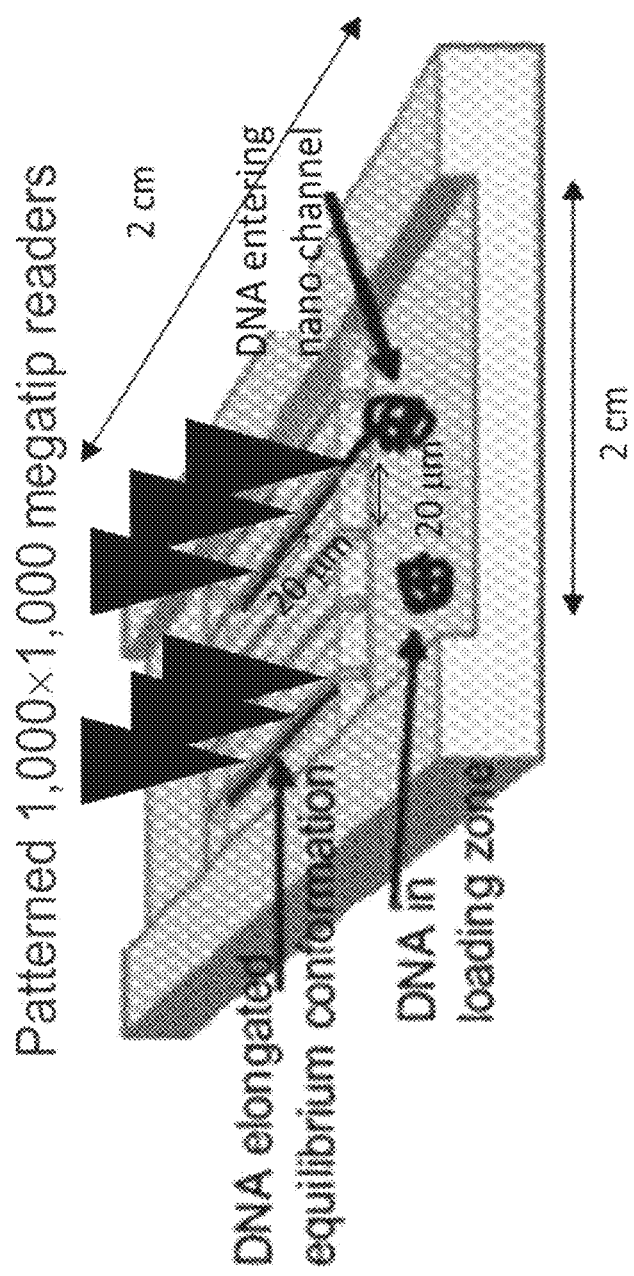
Figure 28:
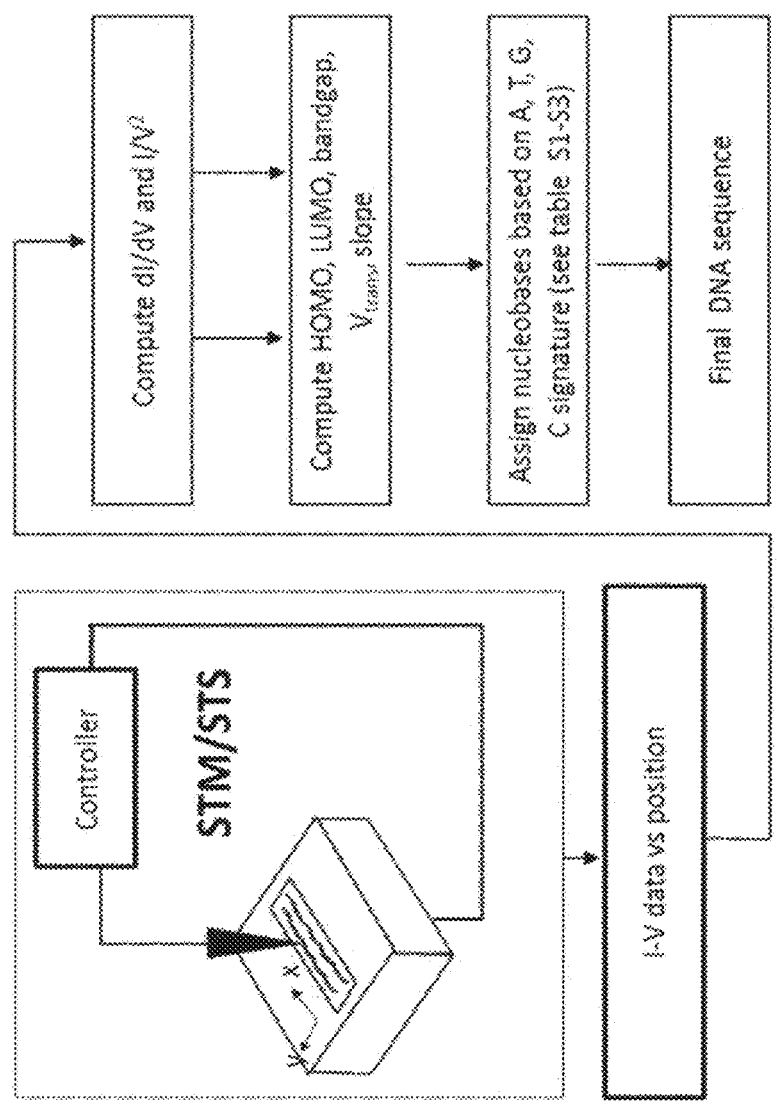
FIG. 28: Schematic diagram showing method of base calling by automatic method.
Figure 29:
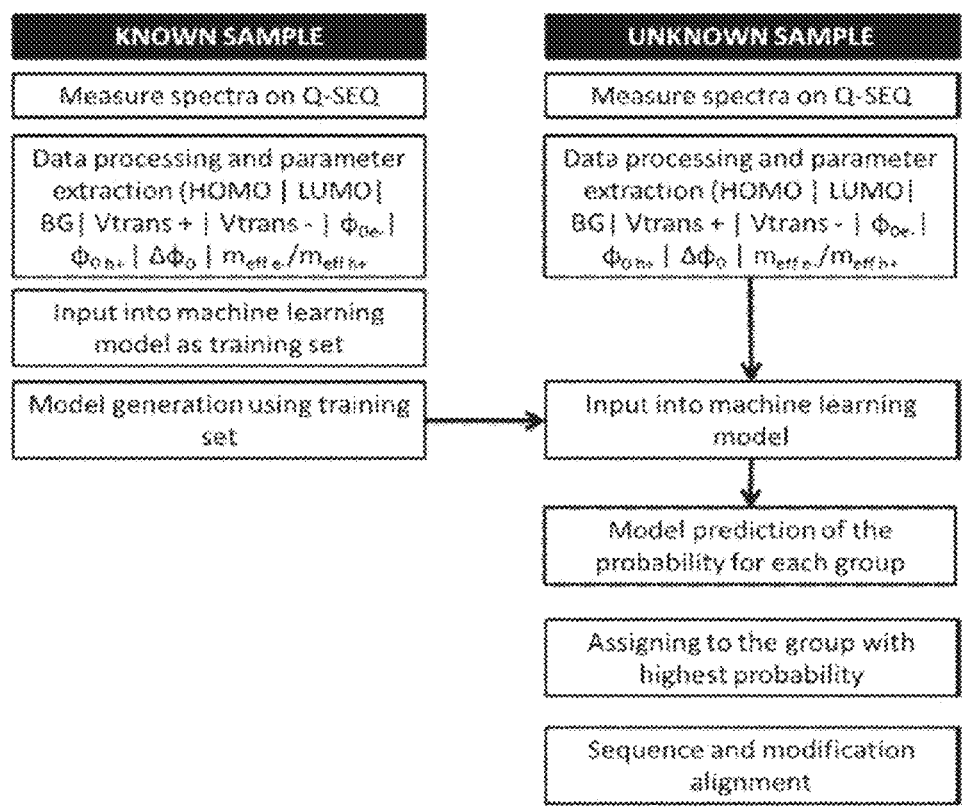
FIG. 29: Flowchart showing an embodiment of a method for determining the identity of a nucleobase, its position on a substrate, and its sequence in a polynucleotide.
Figure 36:
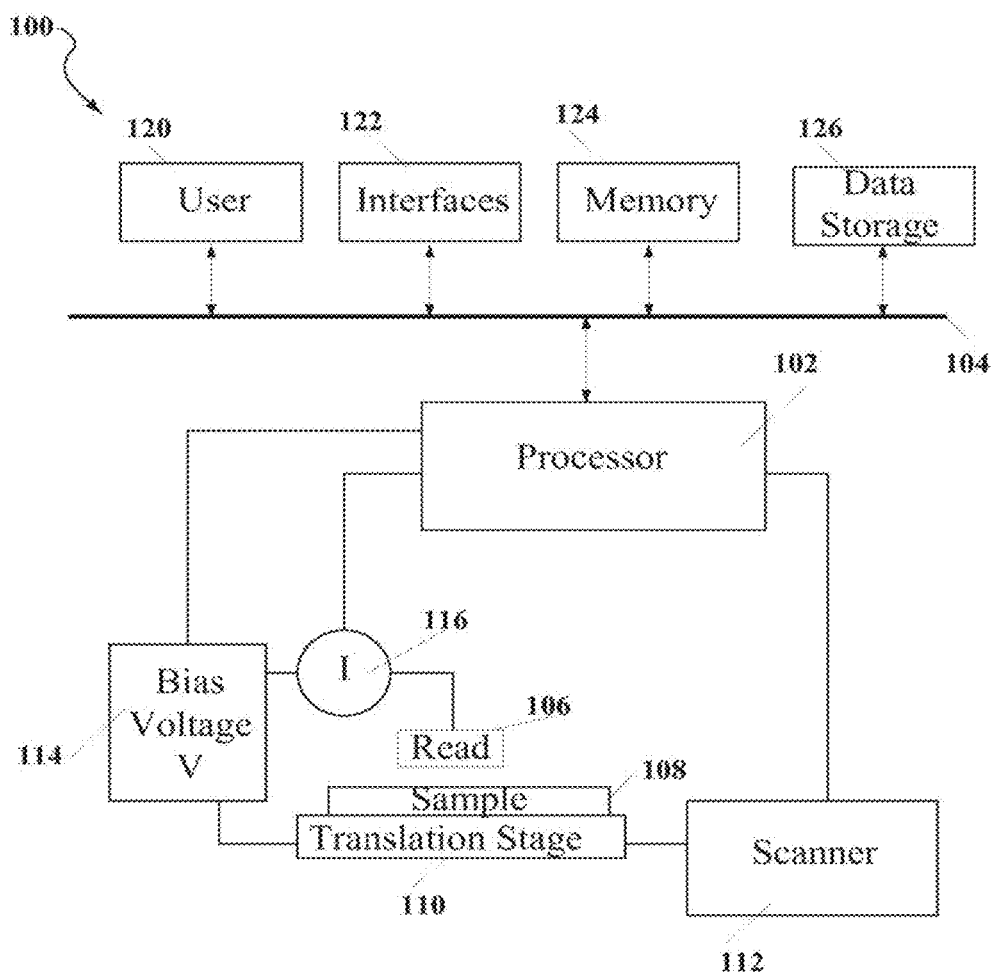
FIG. 36: Schematic diagram showing the detailed design of an experimental setup for QM-Seq.

FIG. 36 illustrates one example of a sequencer 100 (polynucleotide sequence determining device) according to some embodiments of the present invention. As shown in FIG. 36, a read head 106 is positioned over a sample 108. Sample 108, as discussed previously, is a single-strand of DNA or RNA sample with one or more nucleotides positioned on a substrate, which may be flat (111) oriented gold. In some embodiments, sample 108 is positioned on a translation stage 110 and read head 106 is fixed. In some other embodiments, sample 108 may be fixed while read head 106 is mounted on a translation stage. Read head 106 can be a single tip read head as discussed above and as is illustrated in FIGS. 1A and 3B or may be an array of tips as illustrated in FIG. 27A, B, C. Sample 108 can be prepared as discussed in, for example, Examples 1-3, above, and shown in FIGS. 3B and 27C. The arrangement of read head 106 over sample 108 is illustrated, for example, in FIGS. 1A, 3B, and 27A, B, C. Illustration of the preparation of sample 108 is illustrated in FIG. 3A and discussed in detail above.

As is further shown in FIG. 36, a bias voltage V is generated between sample 108 and read head 106 by bias voltage generator 104 and a current I is measured by current sensor 116. Bias voltage generator 104 can be controlled by a processor 102 to scan across a range of bias voltages V and the current I at each bias voltage V is read by current sensor 116 and provided to processor 102. As such, processor 102 can collect an I/V curve (otherwise referred to as a spectra, tunneling data) for each x-y position of read head 106 over sample 108. As is further shown in FIG. 36, processor 102 is coupled to control a scanner 112 that is coupled to a translation stage 110. Translation stage 110 can, for example, be a piezoelectric x-y-z stage capable of moving sample 108 relative to read head 106 as directed by scanner 112. However, any translation stage that is capable of moving sample 108 in a precise fashion can be utilized.

Processor 102, therefore, can control both the position of sample 108 relative to read head 106 and can further be coupled to a data backbone 104 and thereby to data storage 126, memory 124, interfaces 122, and user interface 120. Data storage 126 can be fixed storage such as memory hard drives, FLASH drives, magnetic drives, etc. Memory 124 can be volatile or non-volatile memory that can store data and software instructions. Interfaces 122 can be any interface that connects to external devices or networks. Interface 122 can, for example, be used to couple sequencer 100 to an external computing system that performs analysis of the electronic signature data acquired by sequencer 100. User interface 120 can be, for example, video screens, audio devices, keyboards, pointer devices, touchscreens, or other devices that allow processor 102 to communicate with a user.

Figure 37:
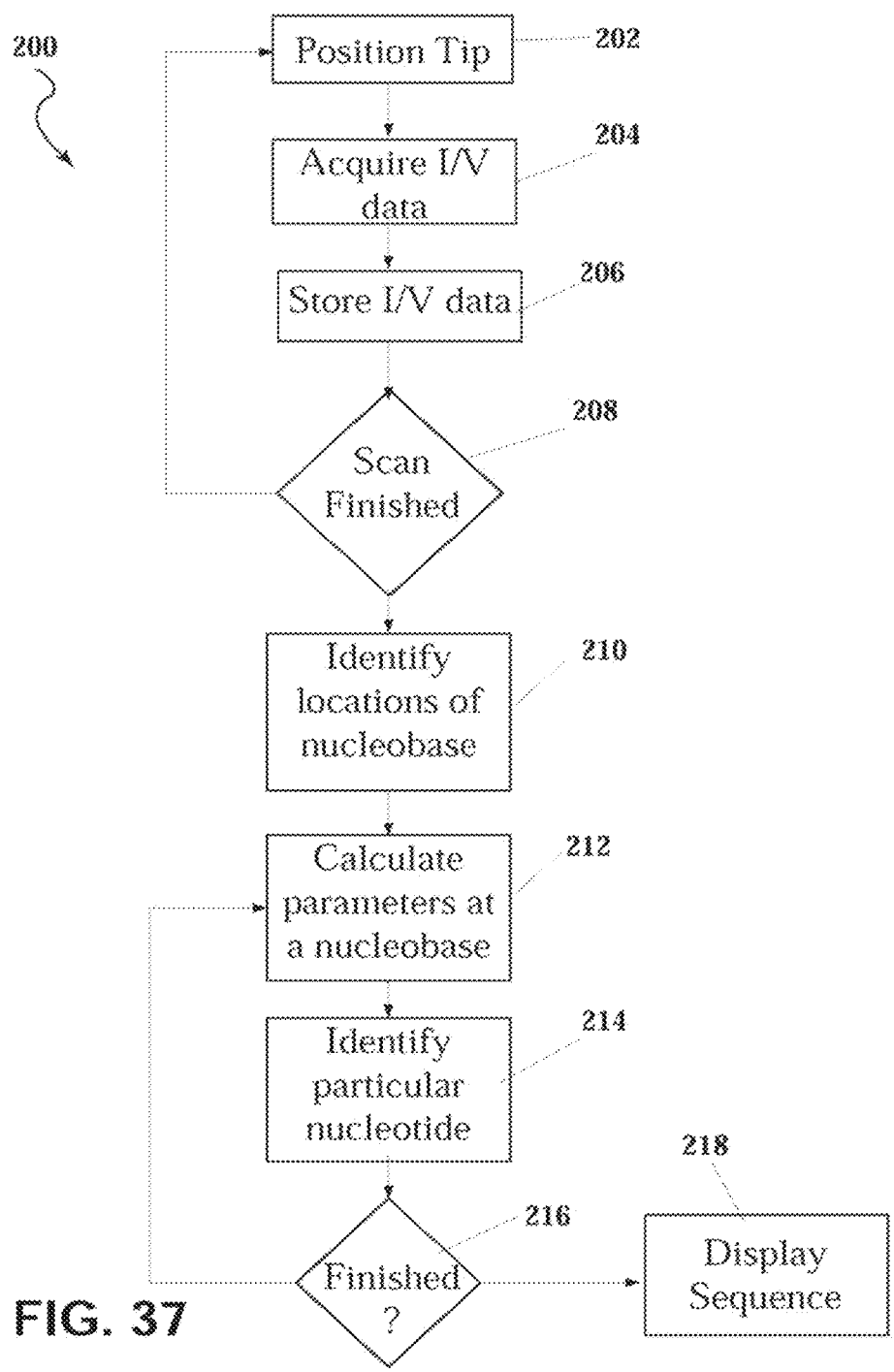
FIG. 37: Schematic diagram showing method of base calling by automatic method.

FIG. 37 illustrates a process 200 that may be executed on a sequencing device such as sequencer 100 shown in FIG. 36 to provide sequencing of one or more strands of DNA or RNA. As shown in FIG. 37, process 100 starts by positioning read head 106 in step 202. As shown in FIG. 36, positioning read head 106 can be accomplished by moving sample 108 with respect to read head 106. Scan positioning can be performed by positioning the tip at a start position, arbitrarily designated as (x,y)=(0,0). Further iterations can step through x,y positions according to a scan pattern. The z position (the distance between read head 106 and sample 108) can be adjusted and fixed by a calibration step using tunneling information for gold prior to execution of process 200. In step 204, I/V data is acquired for each read tip on read head 106 at the current (x,y) position. In step 206, the tunneling data or I/V data may be stored for later analysis. In some embodiments, analysis of the tunneling data or I/V data may be performed concurrently with data acquisition.

In step 208, processor 102 checks to see if the scan is finished. A scan is finished if tunneling data is collected at each x-y position on the substrate. In some embodiments the user may select a subset of x-y positions for analysis. If the scan is not, processor 102 returns to step 202 where read head 106 is positioned at the next x-y location over sample 108. If the scan is finished, then data analysis begins at step 210. In some embodiments, data analysis may be performed by processor 102 on sequencer 100 and sequencer 100 may transmit the acquired tunneling data for further analysis on a separate computer. Therefore, in some embodiments, processor 102 may provide data to an analysis computer (not shown) where the remainder of this process is accomplished.

In step 210, based on the acquired tunneling data or I/V data the x-y location of individual nucleotides can be obtained. This process is illustrated and discussed above, for example, with respect to FIG. 10a, b. In particular, dI/dV data can be analyzed to identify LUMO and HOMO peaks, which may indicate that read head 106 is positioned over a nucleotide in sample 108. If only the low voltage peak is acquired, then read head 106 is positioned over the gold substrate. In a multi-tip array, data from each tip can be separately analyzed to determine the location of individual nucleotides on sample 108.

In step 212, individual parameters are calculated using the tunneling current data, or I/V data, at each x-y location that is identified to be over a nucleotide. Parameters, as discussed throughout, may include dI/dV, $I/V^2$, HOMO, LUMO, Energy Bandgap $V_{trans,\ e-}$, $V_{trans,\ h+}$, $\phi_{0,e-}$, $\phi_{0,h+}$, $\Delta\phi$ and $m_{eff\ e-}/m_{eff\ h}$. (As discussed above, and illustrated in FIGS. 36 and 37). A collection of three or more parameter values for a nucleotide comprise an electronic signature for an unknown nucleotide.

In step 214, the unknown nucleotide is identified based on a comparison of the the nucleotide's signature obtained in step 212 with a database of parameter values for known nucleotides collected in the same environment. For the comparison, values of the parameters selected for determining the signature of the unknown nucleobase (for example HOMO, LUMO, Bandgap, $V_{trans,e-}$, and $V_{trans,\ h+}$) are compared against values for the same parameters (in this case HOMO, LUMO, Bandgap, $V_{trans,e-}$, and $V_{trans,\ h+}$) from known nucleobases (as described above in Example 2). For various embodiments, values for parameters of known nucleobases are provided in Tables VIII-X. In some embodiments, these values for known nucleobases (modified and unmodified) are referred to as a "reference library" of values and may be stored as electronic data in a database.

Identified parameters from individual modified or unmodified oligos (as determined on training sets from well-characterized, known sequences, such as homopolynucleotides containing or lacking modifications) are used to construct a machine learning model (for example a Naïve-Bayes model, which classifies previously defined groups based on Bayesian probability that the new data point belongs in a specific group). In this model, parameters are assumed (naively) that they are independent from each other and compared to the reference. Then, the overall score or probability that the parameter fingerprint is in each group is computed and provided as output. The highest score or probability that the parameter fingerprint is from a certain group is defined. Then, unknown parameter fingerprints, are compared against the model to identify the probability of the parameter fingerprint belonging to each individual group from the training set in the model. The group with the highest probability is assigned to the original spectra and used for sequence alignment. This methodology allows identification of both sequence and structure simultaneously. In some embodiments, the parameter fingerprint can be added to the model as the nucleobases are identified.

Other machine learning processes for data classifications (supervised machine learning) that can be used include: Analytical learning, Artificial neural network, Backpropagation, Boosting (meta-algorithm), Bayesian statistics, Case-based reasoning, Decision tree learning, Inductive logic programming, Gaussian process regression, Group method of data handling, Kernel estimators, Learning Automata, Minimum message length (decision trees, decision graphs, etc.), Multilinear subspace learning, Naive bayes classifier, Nearest Neighbor Algorithm, Probably approximately correct learning (PAC) learning, Ripple down rules, a knowledge acquisition methodology, Symbolic machine learning algorithms, Sub-symbolic machine learning algorithms, Support vector machines, Random Forests, Ensembles of Classifiers, Ordinal classification, Data Pre-processing, Handling imbalanced datasets, Statistical relational learning, Proaftn, and multi-criteria classification algorithm.

As discussed above, values for parameters derived from the tunneling current data were identified, for example, HOMO, LUMO, Band Gap, Transition voltage (positive and negative), ratio of electron/hole effective masses, $\varphi_0$ for electron and hole and $\Delta\varphi_0$. These values were identified for both unmodified homo oligomers or modified (either with NMIA or DMS) homo oligomers in various environments. These identified parameters, referred to as "training sets" were obtained from well-characterized, known sequences, such as homopolynucleotides containing or lacking modifications. The parameter values from the training sets were then used to construct a machine learning model as a reference. Various machine learning models may be used, for example a Naïve-Bayes model, which classifies previously defined groups based on Bayesian probability that the new data point belongs in a specific group. In this model, parameters are assumed (naively) to be independent from each other and compared to the reference. Then, an overall score or probability that the new data point belongs in each group is computed and provided as output. The highest score/probability from a certain group is defined as a called group.

Next, tunneling current data is collected for unknown nucleobases. This tunneling current data was processed to determine values for the various parameters: HOMO, LUMO, Energy Bandgap $V_{trans,\ e-}$, $V_{trans,\ h+}$, $\varphi_{0,e-}$, $\varphi_{0,h+}$, $\Delta\varphi$ and $m_{eff\ e-}/m_{eff\ h+}$. These values were then compared against values obtained from the training sets in order to identify the probability that the unknown nucleobase belongs to an individual group from the training set. The called group (the group with highest probability of matching the unknown nucleobase's group) is assigned to that nucleobase and used for sequence alignment. This methodology allows identification of both sequence and structure simultaneously. Other machine learning processes for data classifications (supervised machine learning) that can be used include: Analytical learning, Artificial neural network, Backpropagation, Boosting (meta-algorithm), Bayesian statistics, Case-based reasoning, Decision tree learning, Inductive logic programming, Gaussian process regression, Group method of data handling, Kernel estimators, Learning Automata, Minimum message length (decision trees, decision graphs, etc.), Multilinear subspace learning, Naive bayes classifier, Nearest Neighbor Algorithm, probably approximately correct (PAC) learning, Ripple down rules, a knowledge acquisition methodology, Symbolic machine learning algorithms, Sub-symbolic machine learning algorithms, Support vector machines, Random Forests, Ensembles of Classifiers, Ordinal classification, Data Pre-processing, Handling imbalanced datasets, Statistical relational learning, Proaftn, and multi-criteria classification algorithm.

In step 216, if the data analysis is not complete (e.g., if all of the data at each identified nuecleobasis site is not analyzed) the process returns to step 212. However, if all of the data has been analyzed, the process displays the determined sequence in step 218.

TABLE VII

A "reference library" for biophysical parameters used in determining electronic fingerprints for DNA nucleotides (A, T, G, C) for base calling. The values were determined on coated (poly lysine, as described above) or uncoated Au(111) substrates in the pH environments listed in the Table.

| Biophysical parameters for determining electronic fingerprints | A | G | C | T |
|---|---|---|---|---|
| Poly-Lysine coated Au(111) Acidic | | | | |
| HOMO (eV) | −1.39 ± 0.30 | −1.36 ± 0.19 | −1.81 ± 0.34 | −1.38 ± 0.19 |
| LUMO (eV) | 1.42 ± 0.24 | 1.48 ± 0.24 | 2.39 ± 0.40 | 2.68 ± 0.30 |
| Bandgap (eV) | 2.81 ± 0.41 | 2.84 ± 0.27 | 4.20 ± 0.49 | 4.06 ± 0.32 |
| $V_{trans+}$ (V) | 1.14 ± 0.20 | 1.13 ± 0.13 | 1.34 ± 0.31 | 1.43 ± 0.37 |
| $V_{trans-}$ (V) | −0.51 ± 0.32 | −0.48 ± 0.29 | −0.80 ± 0.26 | −0.44 ± 0.19 |
| $\varphi_{e-}$ (eV) | 1.45 ± 0.57 | 1.33 ± 0.30 | 2.62 ± 0.89 | 2.75 ± 0.69 |
| $\varphi_{h+}$ (eV) | 1.03 ± 0.61 | 0.79 ± 0.50 | 1.57 ± 0.63 | 0.85 ± 0.40 |
| $m_{e-}/m_{h+}$ | 0.29 ± 0.23 | 0.32 ± 0.25 | 0.64 ± 0.31 | 0.33 ± 0.17 |
| $\Delta\varphi$ (eV) | 2.48 ± 0.98 | 2.12 ± 0.65 | 4.19 ± 1.17 | 3.61 ± 0.73 |
| Au(111) Acidic | | | | |
| HOMO (eV) | −1.13 ± 0.13 | −1.14 ± 0.11 | −1.20 ± 0.18 | −1.74 ± 0.29 |
| LUMO (eV) | 1.61 ± 0.20 | 2.01 ± 0.28 | 2.31 ± 0.88 | 3.08 ± 0.46 |
| Bandgap (eV) | 2.74 ± 0.20 | 3.15 ± 0.32 | 3.52 ± 0.99 | 4.82 ± 0.48 |
| $V_{trans+}$ (V) | 1.28 ± 0.20 | 1.49 ± 0.24 | 1.57 ± 0.42 | 1.62 ± 0.40 |
| $V_{trans-}$ (V) | −0.55 ± 0.33 | −0.53 ± 0.27 | −0.55 ± 0.23 | −0.91 ± 0.49 |
| $\varphi_{e-}$ (eV) | 1.72 ± 0.51 | 2.98 ± 0.77 | 3.36 ± 1.70 | 4.49 ± 1.97 |
| $\varphi_{h+}$ (eV) | 0.68 ± 0.30 | 0.74 ± 0.36 | 0.84 ± 0.38 | 1.95 ± 1.42 |
| $m_{e-}/m_{h+}$ | 0.56 ± 0.51 | 0.60 ± 0.70 | 0.57 ± 0.52 | 0.78 ± 0.37 |
| $\Delta\varphi$ (eV) | 2.40 ± 0.59 | 3.73 ± 0.99 | 4.20 ± 1.94 | 6.44 ± 2.60 |
| Au(111) Neutral | | | | |
| HOMO (eV) | −1.50 ± 0.24 | −1.53 ± 0.13 | −1.50 ± 0.19 | −1.39 ± 0.22 |
| LUMO (eV) | 1.72 ± 0.28 | 1.90 ± 0.25 | 1.61 ± 0.29 | 2.31 ± 0.20 |
| Bandgap (eV) | 3.22 ± 0.20 | 3.44 ± 0.24 | 3.11 ± 0.24 | 3.70 ± 0.25 |
| $V_{trans+}$ (V) | 1.37 ± 0.28 | 1.56 ± 0.37 | 1.14 ± 0.24 | 1.37 ± 0.18 |
| $V_{trans-}$ (V) | −0.58 ± 0.43 | −0.47 ± 0.29 | −0.47 ± 0.28 | −0.50 ± 0.39 |
| $\varphi_{e-}$ (eV) | 2.11 ± 0.57 | 2.78 ± 0.92 | 1.71 ± 0.60 | 2.01 ± 0.56 |
| $\varphi_{h+}$ (eV) | 1.22 ± 1.02 | 0.93 ± 0.32 | 0.91 ± 0.48 | 0.59 ± 0.24 |

TABLE VII-continued

A "reference library" for biophysical parameters used in determining electronic fingerprints for DNA nucleotides (A, T, G, C) for base calling. The values were determined on coated (poly lysine, as described above) or uncoated Au(111) substrates in the pH environments listed in the Table.

| Biophysical parameters for determining electronic fingerprints | A | G | C | T |
|---|---|---|---|---|
| $m_{e-}/m_{h+}$ | 0.36 ± 0.34 | 0.29 ± 0.27 | 0.37 ± 0.39 | 0.45 ± 0.41 |
| $\Delta\phi$ (eV) | 3.33 ± 1.08 | 3.71 ± 0.93 | 2.63 ± 0.61 | 2.60 ± 0.49 |
| Au(111) Basic | | | | |
| HOMO (eV) | −1.28 ± 0.17 | −1.60 ± 0.34 | −1.39 ± 0.20 | −1.48 ± 0.38 |
| LUMO (eV) | 1.72 ± 0.19 | 1.33 ± 0.17 | 1.46 ± 0.15 | 1.56 ± 0.23 |
| Bandgap (eV) | 3.00 ± 0.22 | 2.94 ± 0.42 | 2.85 ± 0.22 | 3.05 ± 0.44 |
| $V_{trans+}$ (V) | 1.36 ± 0.28 | 1.06 ± 0.09 | 1.16 ± 0.15 | 1.33 ± 0.33 |
| $V_{trans-}$ (V) | −0.43 ± 0.35 | −0.72 ± 0.19 | −0.49 ± 0.35 | −0.57 ± 0.36 |
| $\phi_{e-}$ (eV) | 1.83 ± 0.45 | 1.40 ± 0.22 | 1.28 ± 0.49 | 1.77 ± 0.74 |
| $\phi_{h+}$ (eV) | 0.76 ± 0.36 | 1.41 ± 0.42 | 0.79 ± 0.29 | 1.01 ± 0.88 |
| $m_{e-}/m_{h+}$ | 0.29 ± 0.36 | 0.48 ± 0.18 | 0.28 ± 0.24 | 0.47 ± 0.67 |
| $\Delta\phi$ (eV) | 2.59 ± 0.58 | 2.81 ± 0.52 | 2.07 ± 0.56 | 2.78 ± 1.41 |

TABLE VIII

A "reference library" for biophysical parameters used as electronic fingerprints for modified (methylated) DNA nucleotides (A, T, G, C) for base calling

| Biophysical parameters/ fingerprints | A | G | C | T |
|---|---|---|---|---|
| Poly-Lysine coated Au(111) Acidic treated with DMS | | | | |
| HOMO (eV) | −2.04 ± 0.28 | −2.24 ± 0.42 | −2.78 ± 0.39 | N/A |
| LUMO (eV) | 2.06 ± 0.37 | 2.30 ± 0.64 | 2.62 ± 0.59 | N/A |
| Bandgap (eV) | 4.10 ± 0.25 | 4.53 ± 0.85 | 5.40 ± 0.36 | N/A |
| $V_{trans+}$ (V) | 1.47 ± 0.37 | 1.50 ± 0.46 | 1.62 ± 0.37 | N/A |
| $V_{trans-}$ (V) | −0.91 ± 0.27 | −1.33 ± 0.55 | −1.89 ± 0.29 | N/A |
| $\phi_{e-}$ (eV) | 1.60 ± 0.36 | 3.29 ± 1.36 | 3.07 ± 0.80 | N/A |
| $\phi_{h+}$ (eV) | 1.28 ± 0.41 | 3.25 ± 1.69 | 3.40 ± 1.13 | N/A |
| $m_{e-}/m_{h+}$ | 1.21 ± 0.98 | 1.13 ± 0.72 | 1.18 ± 1.46 | N/A |
| $\Delta\phi$ (eV) | 2.87 ± 0.74 | 6.54 ± 2.98 | 6.46 ± 1.89 | N/A |

TABLE IX

A "reference library" for biophysical parameters used as electronic fingerprints for RNA nucleotides (A, U, G, C) for base calling

| Biophysical parameters/ fingerprints | A | G | C | U |
|---|---|---|---|---|
| Poly-Lysine coated Au(111) Acidic | | | | |
| HOMO (eV) | −1.44 ± 0.20 | −1.40 ± 0.31 | −1.40 ± 0.24 | −1.51 ± 0.25 |
| LUMO (eV) | 1.47 ± 0.21 | 1.47 ± 0.19 | 2.20 ± 0.22 | 2.04 ± 0.25 |
| Bandgap (eV) | 2.90 ± 0.27 | 2.86 ± 0.31 | 3.60 ± 0.25 | 3.54 ± 0.31 |
| $V_{trans+}$ (V) | 1.26 ± 0.26 | 1.13 ± 0.17 | 1.59 ± 0.28 | 1.53 ± 0.34 |
| $V_{trans-}$ (V) | −0.63 ± 0.23 | −0.59 ± 0.15 | −0.59 ± 0.33 | −0.90 ± 0.36 |
| $\phi_{e-}$ (eV) | 2.06 ± 0.72 | 1.97 ± 0.44 | 3.17 ± 0.63 | 3.71 ± 1.36 |
| $\phi_{h+}$ (eV) | 1.25 ± 0.59 | 1.07 ± 0.44 | 1.23 ± 0.68 | 1.98 ± 1.09 |
| $m_{e-}/m_{h+}$ | 0.43 ± 0.17 | 0.54 ± 0.19 | 0.39 ± 0.25 | 0.68 ± 0.29 |
| $\Delta\phi$ (eV) | 3.30 ± 0.93 | 3.04 ± 0.72 | 4.40 ± 1.00 | 5.68 ± 1.61 |
| Poly-Lysine coated Au(111) Neutral | | | | |
| HOMO (eV) | −1.45 ± 0.36 | −1.37 ± 0.24 | −1.53 ± 0.35 | −1.18 ± 0.21 |
| LUMO (eV) | 1.48 ± 0.27 | 1.48 ± 0.41 | 1.52 ± 0.16 | 2.49 ± 0.56 |
| Bandgap (eV) | 2.92 ± 0.40 | 2.85 ± 0.45 | 3.05 ± 0.37 | 3.67 ± 0.63 |
| $V_{trans+}$ (V) | 1.31 ± 0.34 | 1.39 ± 0.28 | 1.21 ± 0.23 | 1.93 ± 0.37 |
| $V_{trans-}$ (V) | −0.89 ± 0.20 | −0.70 ± 0.32 | −0.86 ± 0.44 | −0.62 ± 0.22 |
| $\phi_{e-}$ (eV) | 2.57 ± 1.03 | 2.67 ± 1.12 | 2.14 ± 0.65 | 4.50 ± 1.06 |
| $\phi_{h+}$ (eV) | 1.85 ± 0.67 | 1.44 ± 0.93 | 2.09 ± 1.30 | 1.08 ± 0.36 |
| $m_{e-}/m_{h+}$ | 0.66 ± 0.18 | 0.50 ± 0.29 | 0.55 ± 0.31 | 0.47 ± 0.32 |
| $\Delta\phi$ (eV) | 4.42 ± 0.91 | 4.12 ± 1.69 | 4.23 ± 1.70 | 5.58 ± 1.06 |
| Poly-Lysine coated Au(111) Basic | | | | |
| HOMO (eV) | −1.42 ± 0.28 | −1.31 ± 0.34 | −1.56 ± 0.21 | −1.50 ± 0.35 |
| LUMO (eV) | 1.45 ± 0.23 | 1.52 ± 0.27 | 1.66 ± 0.25 | 1.62 ± 0.37 |
| Bandgap (eV) | 2.87 ± 0.36 | 2.83 ± 0.37 | 3.21 ± 0.34 | 3.11 ± 0.45 |
| $V_{trans+}$ (V) | 1.45 ± 0.36 | 1.67 ± 0.42 | 1.41 ± 0.26 | 1.53 ± 0.31 |
| $V_{trans-}$ (V) | −0.63 ± 0.30 | −0.96 ± 0.33 | −0.94 ± 0.38 | −1.14 ± 0.48 |

TABLE IX-continued

A "reference library" for biophysical parameters used as electronic fingerprints for RNA nucleotides (A, U, G, C) for base calling

| Biophysical parameters/ fingerprints | A | G | C | U |
|---|---|---|---|---|
| $\phi_{e-}$ (eV) | 2.48 ± 0.73 | 4.01 ± 0.96 | 3.15 ± 0.77 | 3.68 ± 0.96 |
| $\phi_{h+}$ (eV) | 1.39 ± 0.57 | 1.94 ± 0.90 | 1.95 ± 0.96 | 2.61 ± 1.40 |
| $m_{e-}/m_{h+}$ | 0.40 ± 0.26 | 0.78 ± 0.36 | 0.80 ± 0.38 | 0.90 ± 0.53 |
| $\Delta\phi$ (eV) | 3.87 ± 1.06 | 5.95 ± 1.23 | 5.09 ± 1.47 | 6.29 ± 1.77 |

TABLE X

A "reference library" for biophysical parameters used as electronic fingerprints for modified RNA modifications (A, U, G, C) for base calling

| Biophysical parameters/ fingerprints | A | G | C | U |
|---|---|---|---|---|
| Poly-Lysine coated Au(111) NMIA | | | | |
| HOMO (eV) | −1.92 ± 0.25 | −1.82 ± 0.37 | −1.59 ± 0.28 | −1.39 ± 0.20 |
| LUMO (eV) | 1.95 ± 0.38 | 1.92 ± 0.49 | 1.46 ± 0.30 | 1.51 ± 0.29 |
| Bandgap (eV) | 3.88 ± 0.42 | 3.74 ± 0.60 | 3.05 ± 0.47 | 2.90 ± 0.34 |
| Vtrans$_+$ (V) | 1.55 ± 0.49 | 1.09 ± 0.17 | 1.17 ± 0.35 | 1.10 ± 0.13 |
| Vtrans$_-$ (V) | −1.07 ± 0.55 | −1.03 ± 0.51 | −0.55 ± 0.17 | −0.34 ± 0.18 |
| $\phi_{e-}$ (eV) | 3.10 ± 1.40 | 1.85 ± 0.90 | 1.82 ± 1.04 | 1.72 ± 0.34 |
| $\phi_{h+}$ (eV) | 2.46 ± 1.65 | 1.41 ± 0.61 | 0.94 ± 0.40 | 0.60 ± 0.34 |
| $m_{e-}/m_{h+}$ | 0.62 ± 0.31 | 1.35 ± 1.37 | 0.44 ± 0.16 | 0.29 ± 0.15 |
| $\Delta\phi$ (eV) | 5.56 ± 2.40 | 3.26 ± 0.79 | 2.76 ± 1.08 | 2.33 ± 0.54 |
| Poly-Lysine coated Au(111) DMS | | | | |
| HOMO (eV) | −1.64 ± 0.32 | −1.81 ± 0.29 | −1.62 ± 0.32 | −1.62 ± 0.34 |
| LUMO (eV) | 1.79 ± 0.39 | 1.87 ± 0.41 | 1.66 ± 0.32 | 1.54 ± 0.31 |
| Bandgap (eV) | 3.43 ± 0.54 | 3.68 ± 0.54 | 3.28 ± 0.53 | 3.16 ± 0.48 |
| Vtrans$_+$ (V) | 1.41 ± 0.44 | 1.40 ± 0.42 | 1.43 ± 0.36 | 1.13 ± 0.20 |
| Vtrans$_-$ (V) | −0.72 ± 0.33 | −0.87 ± 0.36 | −0.73 ± 0.33 | −0.61 ± 0.33 |
| $\phi_{e-}$ (eV) | 3.25 ± 1.53 | 2.93 ± 1.46 | 3.11 ± 1.39 | 1.74 ± 0.62 |
| $\phi_{h+}$ (eV) | 1.39 ± 0.81 | 1.70 ± 0.87 | 1.38 ± 0.89 | 1.05 ± 0.70 |
| $m_{e-}/m_{h+}$ | 0.69 ± 0.49 | 0.72 ± 0.43 | 0.67 ± 0.45 | 0.82 ± 2.40 |
| $\Delta\phi$ (eV) | 4.64 ± 1.76 | 4.64 ± 1.68 | 4.49 ± 1.94 | 2.79 ± 1.00 |

Example 5—Detection of Modified Nucleobases

Figure 8A:
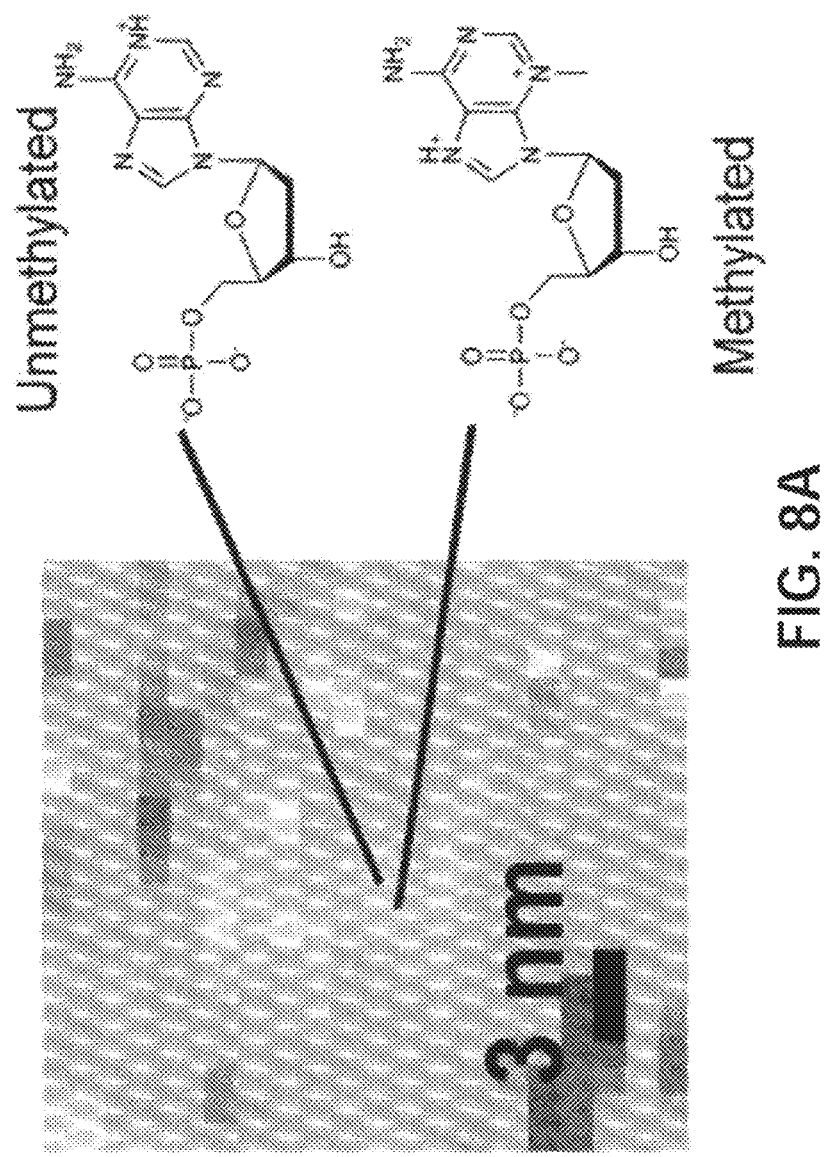
FIGS. 8A-E: Identification of single nucleotide modifications using STM-STS. (a) STM image of adenine oligomer treated with dimethyl sulfate (DMS), deposited on poly-L-lysine coated Au(111) substrate, under acidic conditions. Facile identification of methylated and unmethylated adenine on adjoining nucleotides (as shown) highlights the potential for detecting single nucleotide modifications, using this new sequencing technique. (b) Reaction products of adenine methylation with DMS, (c) Reaction scheme of guanine with DMS to produce 7-methyl guanine and its hydrolyzed product with an opened-ring, (d) Distribution of HOMO/LUMO levels under acidic conditions for unmethylated (solid line) and methylated (dashed line) for adenine, (e) Distribution of HOMO/LUMO levels under acidic conditions for guanine (solid line), methylated guanine (dotted line) and ring-opened methylated guanine (dashed line).
Figure 8B:
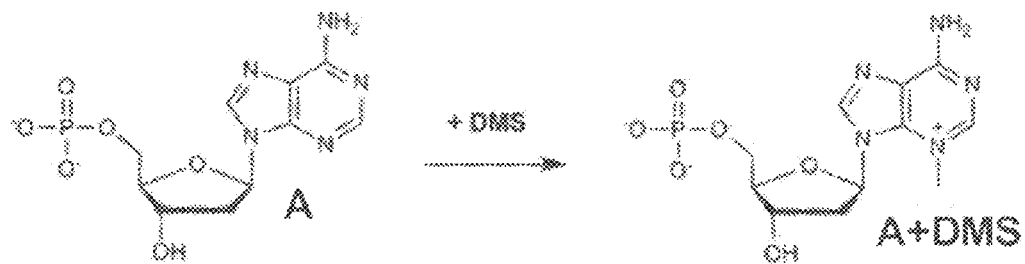
Figure 8C:
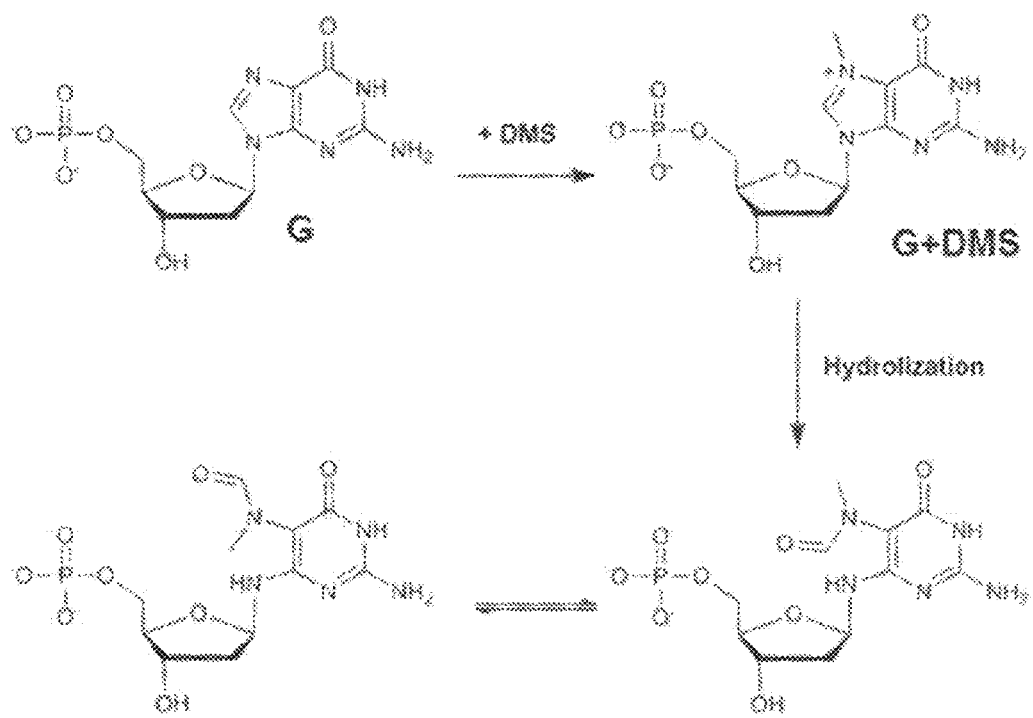
Figure 8D:
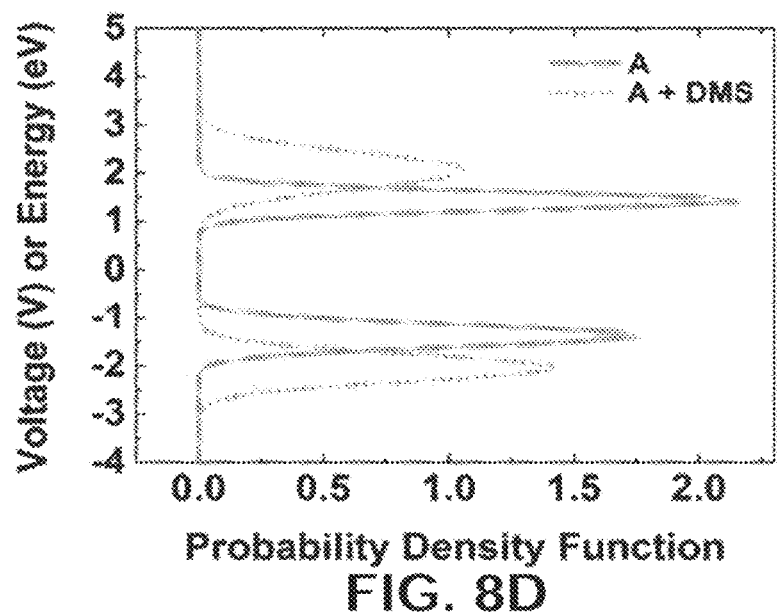
Figure 8E:
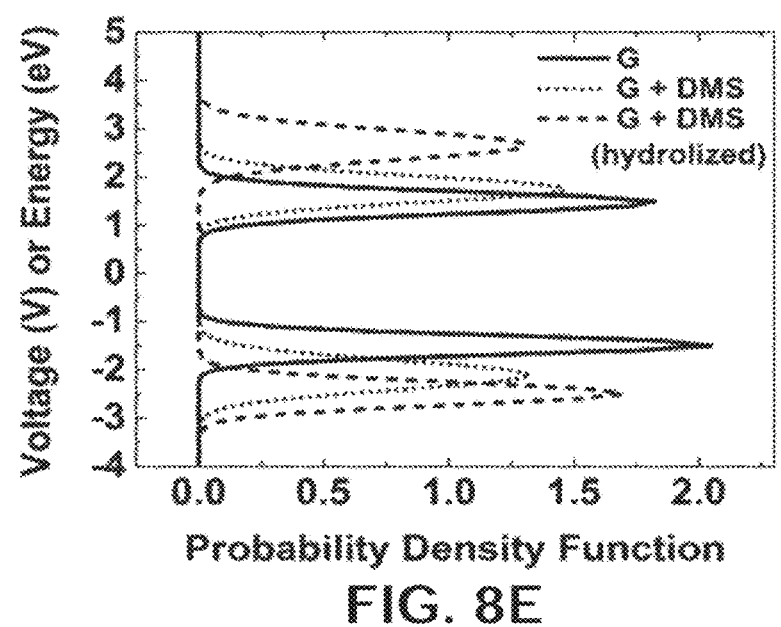
Figure 9A:
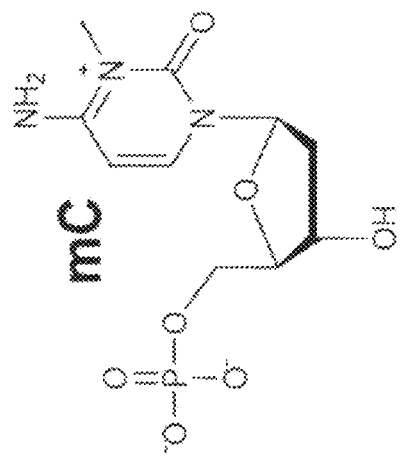
FIGS. 9A-D: Identification of single nucleotide modifications using QM-Seq. (a) Reaction products of cytosine methylation with DMS. (b) Boxplot (25-75% quartiles) of HOMO and LUMO positions under acidic conditions for unmethylated (blue) cytosine and methylated cytosine (purple). Whiskers show the 5%-95% percentiles, central line is the median. (c-d) Tunneling spectra (I-V, dotted curve) and (dI/dV, solid curve) of unmethylated cytosine (c) and methylated cytosine (d). Both have the same vertical axis (Voltage). Superimposed blue and purple lines are visual aid to show the difference on the peak position with respect to each distribution.
Figure 9A:
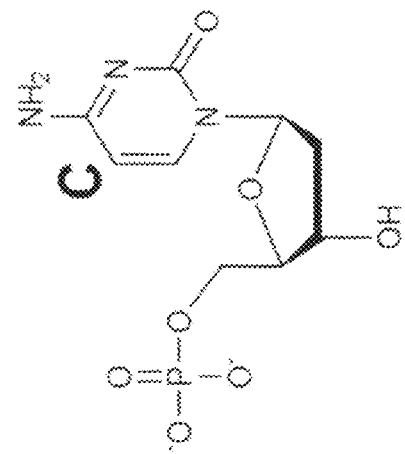
Figures 9B, 9C, 9D:
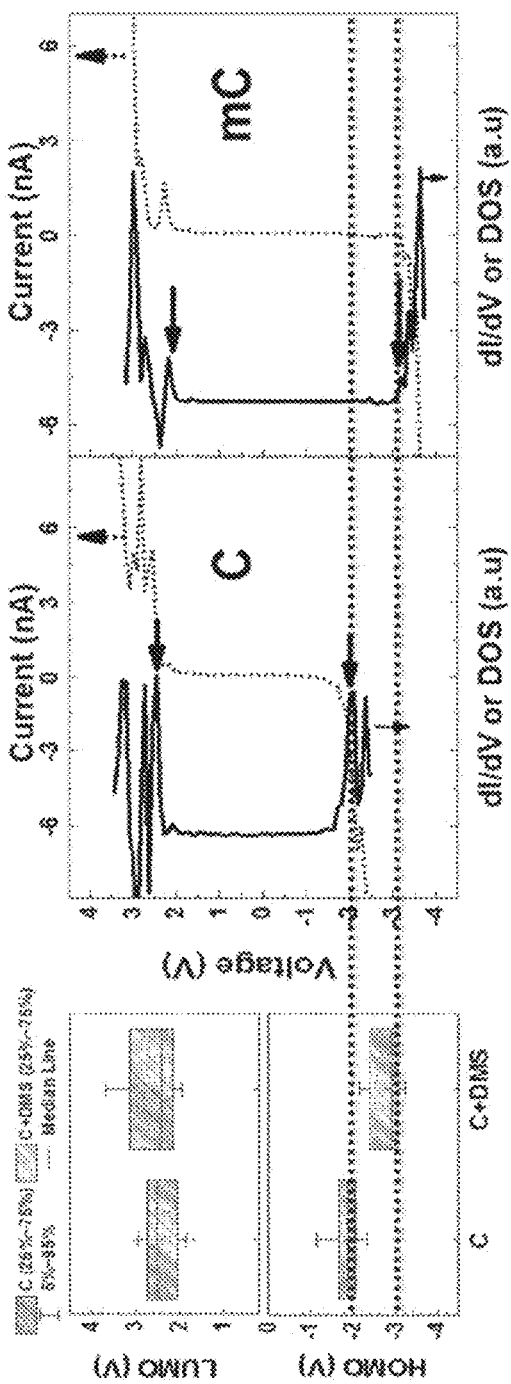
Figure 11A:
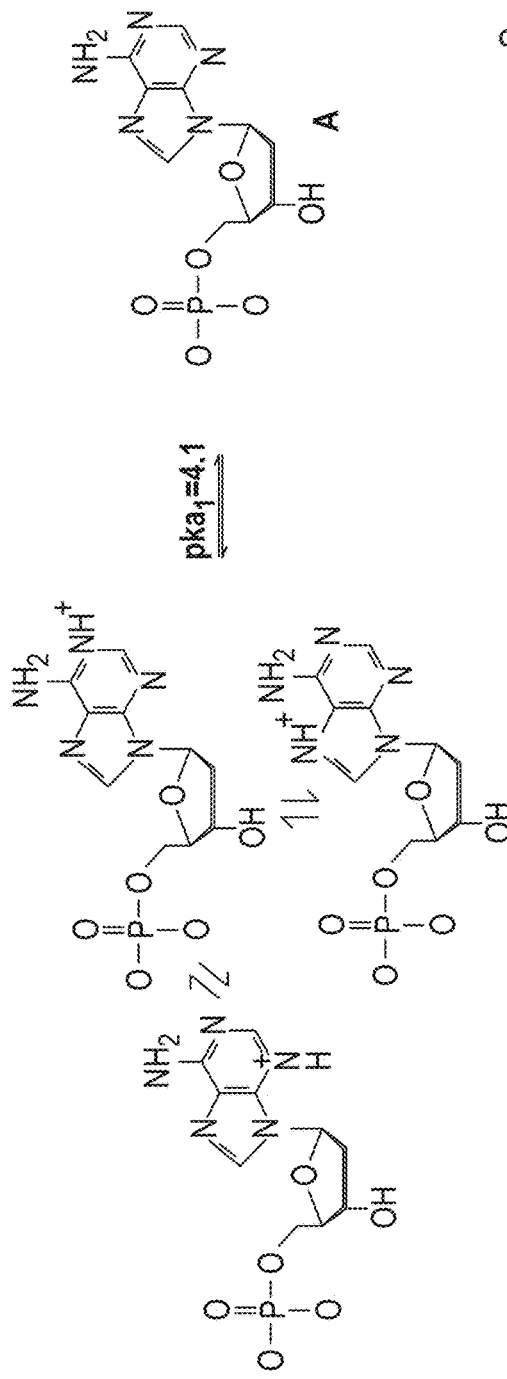
FIGS. 11A-D: Chemical structure of nucleotides under different pH conditions with their respective pKa. From top to bottom, (a) Adenine (A), (b) Guanine (G), (c) Cytosine (C), and (d) Thymine (T). Thymine has a single pKa at 9.9 under acidic conditions and can undergo enolization and protonation.
Figure 11B:
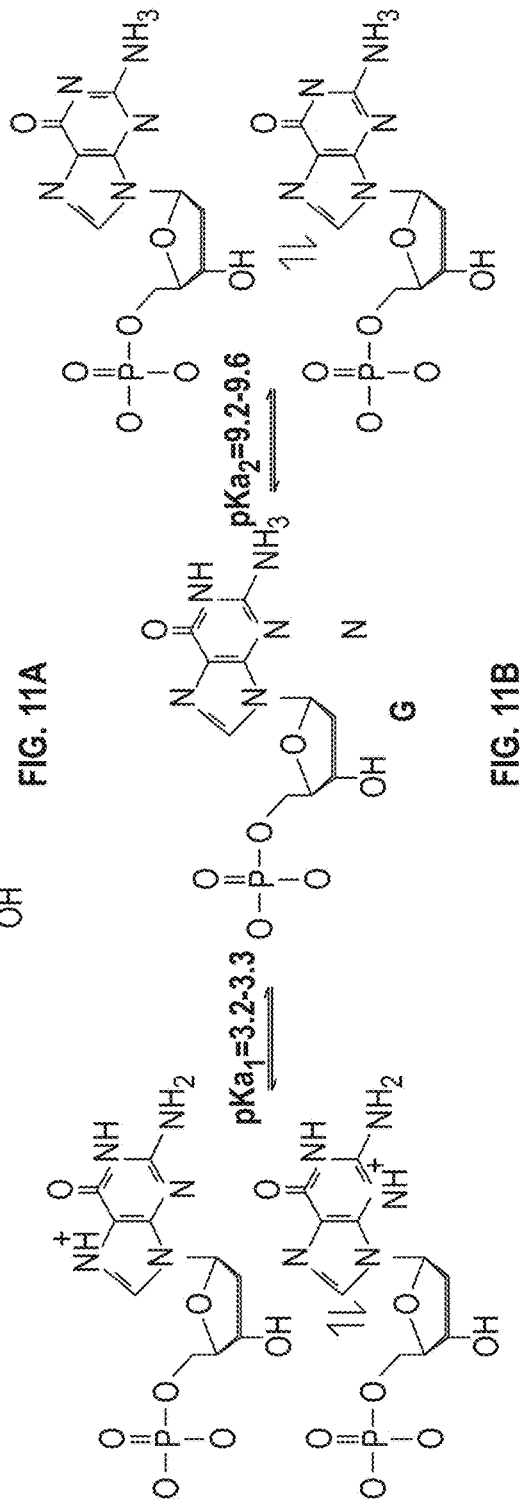
Figure 11C:
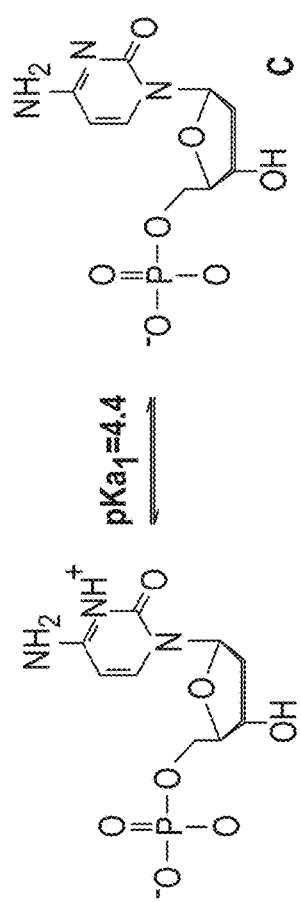
Figure 11D:
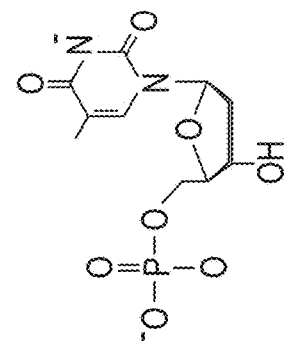
Figure 11D:
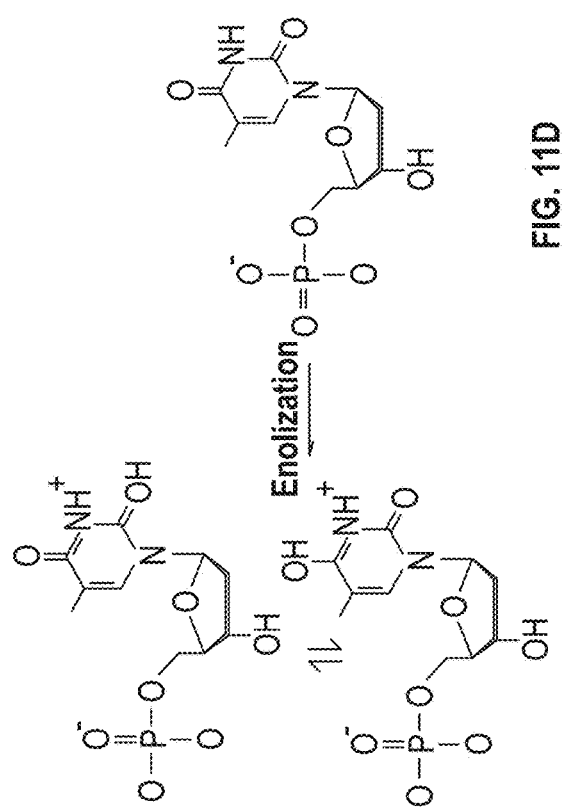

For these experiments, DNA oligomers were methylated using dimethyl sulfate (DMS) (FIGS. 8, 9, 18). Methylation is a particularly important modification for epigenetic gene silencing, and can potentially be used for detection of early onset of diseases like cancer. DNA methylation results in a change of the biochemical structure of the methylated nucleotide compared to the non-methylated nucleotide (FIG. 8B, C, 24A). Dimethyl sulfate is known to react with DNA to methylate guanine and adenine on single stranded regions while cytosine is known to react to a limited extent. In vivo, DNA may contain methylated cytosine bases, specifically, 5-methylcytosine. Other potential methylated bases include, 5-Hydroxymethylcytosine, 7-Methylguanosine, N6-Methyladenosine.

Methylation may change the probability of charge tunneling, STS measurements were conducted to investigate resultant changes in the spectrum. As observed (FIG. 8, 24, Table VI), a chemical modification of the purine or pyrimidine rings affects the conjugation and reduces the tunneling probability of both electron and hole.

TABLE VI

Summary of LUMO, HOMO, band gap energy levels for methylated and unmethylated A, C and G on modified gold surface. Values correspond to mean ± standard deviation.

| | Voltage (V)/Energy (eV) | Methylated | Unmethylated |
|---|---|---|---|
| A | LUMO (V) | 2.19 ± 0.52 | 1.43 ± 0.18 |
| | HOMO (V) | −2.01 ± 0.28 | −1.37 ± 0.22 |
| | Band Gap (eV) | 4.15 ± 0.42 | 2.79 ± 0.32 |
| C | LUMO (V) | 2.62 ± 0.59 | 2.17 ± 0.28 |
| | HOMO (V) | −2.78 ± 0.39 | −1.86 ± 0.39 |
| | Band Gap (eV) | 5.40 ± 0.36 | 4.03 ± 0.37 |
| G | LUMO (V) | 2.32 ± 0.58 | 1.48 ± 0.22 |
| | HOMO (V) | −2.15 ± 0.48 | −1.49 ± 0.19 |
| | Band Gap (eV) | 4.47 ± 0.78 | 2.96 ± 0.25 |

Methylation of DNA

DNA methylation was performed using dimethyl sulfate (DMS) (SPEX CertiPrep, USA) after diluting to 800 μM in methanol. 10 μL of DNA oligomer (20 μM) was mixed with 10 μL of 800 μM DMS (equivalent to 2.6 excess with respect to DNA oligomers) and incubated for 24 hours at room temperature. Methylated DNA was precipitated using standard ethanol precipitation. Solution was diluted to 90 μL with sterile double distilled water, followed by addition of 10 μL of Sodium Acetate (3M, pH 5.5) and 200 μL of chilled absolute ethanol. The solution was mixed and incubated for at least 20 min at −20° C. Afterwards, it was centrifuged at 13,000 rpm for 15 min and the supernatant was removed. The DNA pellet obtained was washed twice with 500 µL and 1000 µL of 70% ethanol followed by centrifugation. Cleaned DNA was then re-suspended in sterile water and its concentration was determined using Nanodrop. The obtained methylated DNA was diluted to half using 0.1M $Na_2SO_4$ for measurements in STM.

Methylation of Guanine and Adenine nucleotides (FIG. 8B, C) resulted in an increase of both LUMO and HOMO energy levels, thereby also increasing the respective HOMO/LUMO energy gap (FIG. 8D, E). The observed change in electronic energy levels may be due to the methylation of purines resulting in a loss of conjugation, as shown in isomers in FIG. 8B, C. The loss of conjugation may result in a larger barrier for tunneling of both electrons and holes (FIG. 8D, E, Table VI). Methylation was also studied in pyrimidines (FIG. 9A, B, Table VI), and the corresponding electronic shifts were observed. Following these investigations, single strands of DNA were methylated. Results from these studies demonstrated that methylated and unmethylated nucleotides may be distinguished at single nucleobase resolution (FIG. 8A). These results point towards the applicability of this technique for detecting single DNA molecules as well as single nucleotide modifications within them.

Figure 39:
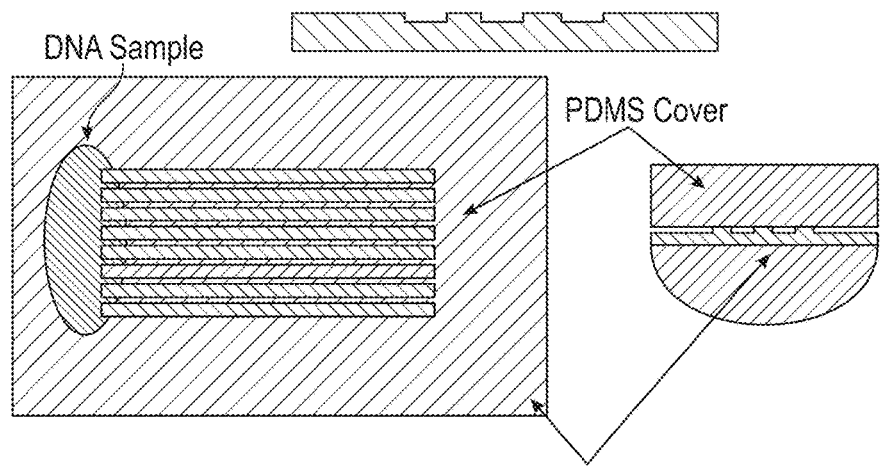
FIG. 39: Schematic showing DNA sample loading in nanofluidic channels for multiplexed sequencing and increasing duty-cycle.

Example 6—Nanofluidic Sample Loading, Sample Alignment, and Increasing Duty-Cycle Nucleic acid sample is loaded into nanofluidic channels (FIG. 38) with 10 nm to 100 µm periodicity for multiplexed QM-Seq using multi-tip arrays. Using a designed silicon template for the nanofluidic channels (FIG. 39), gold deposition, flame annealing (to form single crystal Au(111) surface), and template stripping is used to obtain atomically flat Au (111) nanofluidic channels (FIG. 39). See, e.g., Nagpal et al., 2009, Science 325: 594. Following template stripping with epoxy or other polymer curing, the gold surface is treated with ozone plasma for 2 minutes to impart negative charge, and then treated with 10-100 ppm positively-charged polyelectrolyte (such as poly-Lysine) to uniformly coat the surface. The resulting nanofluidic channels coated with polystyrene are covered with a flat PDMS stamp treated with oxygen plasma for two minutes (to make the surface hydrophilic). The nucleic acid sample is fed into the channels, loading them with linearized nucleic acid. Nucleic acid is loaded into the channels, for example, near the middle and some along the edges, thereby increasing the duty-cycle (fraction of area with nucleic acid) and reducing the need to scan large areas that lack nucleic acid. Since atomic force micrograph (AFM) or scanning tunneling microscopy (STM) can only access the middle part of the channel due to spatial constraints (see FIG. 38), the scanned regions using multiplexed tips may be fully-loaded with DNA sample (using the channel depth, DNA concentration, and tip geometry as adjustable parameters), thereby increasing the duty-cycle.

Example 7—Massively Parallel Sequencing

Massively parallel sequencing using the disclosed method may be achieved in various ways. In one embodiment, a 1 megapixel (or one megatip) 2 cm×2 cm chip is used in a process similar to CCD or camera chip. For example, voltage can be simultaneously applied to a plurality of tips, the current is collected and stored, and all current values from the plurality of tips may be read simultaneously (similar to a CCD). After the current is read, another bias voltage can be applied, and so on, to recreate the entire current-voltage curve over a massive 2 cm×2 cm substrate. Thus several thousand genomes can be placed and read simultaneously. Piezos may be used to move a sample a few angstroms, to allow for sequencing the next nucleobases— and the process repeated to analyze additional nucleobases. Therefore, in a single 2 micrometer scan movement (or piezo scan), the disclosed method, set up as a massively parallel sequencer, can sequence all possible nucleobases on a relatively large sample biochip, patterned using a simple microfluidic device. In various embodiments the polynucleotides may be extruded onto a substrate having various sizes for example less than about 1.0 cm, FIG. 27A is a picture of centimeter scale optically created tip patterns, using a simple optical lithography, followed by anisotropic KOH etching. The multi-tip sequencer will be made using a megapixel tip array fabricated using modified template stripping process (Nagpal et. al., Science, 325, 594, 2009). By using optical lithography of circular or square holes in otherwise protected silicon (100) surface, we utilized self-limiting anisotropic potassium hydroxide etching (KOH etching) process to make patterned inverted pyramid divets on a smooth silicon wafer. The inverted pyramids tips are periodic, and the periodicity, packing, and patterning is easily changed using the optical lithography of exposed silicon wafer. These inverted pyramids are then coated with gold, silver, or copper metal, followed by back-filling with epoxy or thick electro-deposited metal-layer backing to allow mechanically stable film. Since these noble metals have no adhesion to the silicon template, these patterned megapixel tips arrays are peeled of, and this megapixel tip array will be used for making the patterned quantum sequencing reader, using a reader array and CCD-type megapixel reads. The microfluidic device dimensions is matched with the periodicity of the megapixel tip reader, to enable massively parallel data acquisition and detection of nucleotide sequence, modification and structure FIG. 27B is an SEM image showing high fidelity and periodically patterned STM tips made from gold. Using a large area (cm×cm) scale STM chip on an ultraflat substrate, a 2 µm×2 µm surface may be scanned, and create an entire sequence over cm scale, by massively parallel scanning and simple readout from a chip, similar to the ones shown in the figure.

Example 8—Multi-Tip Design and Massively Parallel Data Acquisition

Two designs for multi-tip readers and massively parallel data acquisition are shown in FIG. 40, using MIS (A) and MIM (B) readers. The charge is stored by each "pixel" or reader head unit, and transferred to adjoining tips for sequential reads in a CCD-type setup. See, e.g., G. C. Hoist, CCD Arrays, cameras and displays, Second Edition, SPIE Optical Engineering Press (1998). For each applied voltage (the voltage is scanned to construct I-V plots, extract QM-Seq fingerprints and base-calling), the reader stores the charge, passes it over, and the timing and sequence is controlled by a microprocessor and selection setup (timed voltage scans on top metal contact or each "pixel"). Each data packet is then read, the current is amplified using an operational amplifier (OPAMP), and converted to a digital signal using an A/D converter. The acquired data is then stored on a computer, and the next voltage is scanned and the process repeated.

The periodicity of the nanofluidic channels and multi-tip readers is matched. The periodicity may be from 10 nm to 100 μm, and in some embodiments, the multi-tip arrays are fabricated in a square array. Height variations in tips are minimized (<~5 nm) for easy alignment, and the tips are packed tightly. For example, with a 50-100 nm periodicity, a 1000×1000 tip array will be packed in a 50×50 μm² or 100×100 μm² space. Using standard flat silicon wafers, achieving ~5 nm height variation in such small space is readily achievable, particularly given an atomically smooth surface.

All references disclosed herein, whether patent or non-patent, are hereby incorporated by reference as if each was included at its citation, in its entirety.

Although the present disclosure has been described with a certain degree of particularity, it is understood the disclosure has been made by way of example, and changes in detail or structure may be made without departing from the spirit of the disclosure as defined in the appended claims.

composed of a hydrophobic polymer, and wherein the substrate comprises a polycationic surface;

a bias voltage coupled to the processor and providing a voltage between the read head and the substrate;

a current sensor coupled between the bias voltage and the read head, the current sensor providing a current to the processor, wherein the processor executes instructions to acquire electronic signature data at a set of positions across the sample and store the electronic signature data according to position, and wherein individual nucleobases can be identified based on the electronic signature data.

2. The sequencer of claim 1, wherein the read head comprises at least 100, at least 500, at least 1000, at least 5000, at least 10,000, at least 50,000, at least 100,000, at least 200,000, at least 500,000, at least 1,000,000, or at least 2,000,000 quantum tunneling tips.

We claim:

1. A sequencer, comprising:
a processor;
a read head having a plurality of quantum tunneling tips;
a substrate capable of supporting at least one polynucleotide that comprises one or more nucleobases, wherein the substrate comprises channels into which a sample may be flowed to deposit at least one polynucleotide onto the substrate, and wherein each channel comprises a bottom surface and two walls, wherein the bottom surface is the conductive substrate and the walls are 3. The sequencer of claim 1, wherein each quantum tunneling tip comprises a metal-insulator-semiconductor (MIS) structure or a metal-insulator-metal (MIM) structure.

4. The sequencer of claim 1, wherein the plurality of quantum tunneling tips are arranged so that currents from individual tips can be independently read.

5. The sequencer of claim 1, wherein the substrate is a conductive substrate.

6. The sequencer of claim 5, wherein the conductive substrate is an ultrasmooth Au(111) substrate.

7. The sequencer of claim 1, wherein two adjacent quantum tunneling tips are between 10 nm and 100 μm, or between 10 nm and 10 μm, or between 10 nm and 1 μm, or between 10 nm and 100 nm apart.

8. The sequencer of claim 1, wherein the processor executes instructions to
   (a) position the read head relative to the substrate at a starting position;
   (b) scan the voltage and measure the current to acquire electronic signature data;
   (c) store the electronic signature data relative to a position between the read head and the substrate;
   (d) reposition the read head relative to the substrate according to a scan pattern; and
   (e) repeat steps (b) through (e) until the scan pattern is complete.

9. The sequencer of claim 8, wherein the processor further executes instructions to identify locations of the nucleobases based on the electronic signature data;
   calculate parameter fingerprints at the identified locations from the electronic signature data; and
   identify the nucleobases based on the parameter fingerprints.

10. The sequencer of claim 1, wherein the electronic signature data is provided to a separate external computing system that executes instructions to
    identify locations of the nucleobases based on the electronic signature data;
    calculate parameter fingerprints at the identified locations from the electronic signature data; and
    identify the nucleobases based on the parameter fingerprints.

11. A method of identifying a first unknown nucleobase comprising:
    determining an electronic signature for the first unknown nucleobase using the sequencer of claim 1 to collect tunneling current data;
    comparing the electronic signature of the first unknown nucleobase to an electronic fingerprint for one or more known nucleobases;
    matching the first unknown nucleobase's electronic signature to an electronic fingerprint of a known nucleobase; and thereby identifying the first unknown nucleobase.

12. The method of claim 11, wherein the electronic signature of the first unknown nucleobase and the electronic fingerprint of the known nucleobases comprise at least three, at least four, at least five, at least six, at least seven, at least eight, or at least nine values selected from the values of LUMO, HOMO, Bandgap, $V_{trans+}$ (V), $V_{trans-}$ (V), $\Phi_{e-}$ (eV), $\Phi_{h+}$ (eV), $m_{e-}/m_{h+}$ and $\Delta\Phi$ (eV).

13. The method of claim 11, further comprising identifying a second unknown nucleobase, wherein the first and second unknown nucleobases are comprises on the same polynucleotide molecule.

14. The method of claim 11, wherein the electronic signature of the first unknown nucleobase is determined in one or more pH environments selected from acidic, neutral, and basic, and compared to the electronic fingerprint of the one or more known bases collected in the same pH environment.

15. The method of claim 11, wherein the polynucleotide is deposited on the substrate by a process comprising a translational motion.

16. The method of claim 15, wherein the method comprises melting at least one double-stranded polynucleotide to form single-stranded polynucleotides prior to depositing the polynucleotides on the substrate.

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Artificial sequence
<220> FEATURE:
<223> OTHER INFORMATION: Sequence primer

<400> SEQUENCE: 1
cgagctcgta aacttggtct ga                                        22

<210> SEQ ID NO 2
<211> LENGTH: 20
<212> TYPE: DNA
<213> ORGANISM: Artificial sequence
<220> FEATURE:
<223> OTHER INFORMATION: Sequence primer

<400> SEQUENCE: 2
gtgaagacga aagggcctcg                                           20

<210> SEQ ID NO 3
<211> LENGTH: 85
<212> TYPE: DNA
<213> ORGANISM: Artificial sequence
<220> FEATURE:
<223> OTHER INFORMATION: Beta-lactamase gene ampR

<400> SEQUENCE: 3
ataagggcga cacggaaatg ttgaatactc atactcttcc tttttcaata ttattgaagc    60
atttatcagg gttattgtct catga                                         85